United States Patent
Chelliah et al.

(10) Patent No.: US 9,708,270 B2
(45) Date of Patent: Jul. 18, 2017

(54) SUBSTITUTED SPIROPIPERIDINYL COMPOUNDS USEFUL AS GPR120 AGONISTS

(71) Applicant: Merck Sharp & Dohme Corp., Rahway, NJ (US)

(72) Inventors: Mariappan Chelliah, Edison, NJ (US); Hong Dong Chu, Livingston, NJ (US); Jason M. Cox, East Windsor, NJ (US); John S. Debenham, Scotch Plains, NJ (US); Keith Eagen, Long Valley, NJ (US); Ping Lan, Plainsboro, NJ (US); Clare London, Chatham, NJ (US); Michael A. Plotkin, Frenchtown, NJ (US); Unmesh Shah, Neshanic Station, NJ (US); Christopher Joseph Sinz, Middletown, NJ (US); Zhongxiang Sun, Princeton, NJ (US); Henry M. Vaccaro, South Plainfield, NJ (US); Srikanth Venkatraman, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/434,524

(22) PCT Filed: Oct. 11, 2013

(86) PCT No.: PCT/US2013/064472
§ 371 (c)(1),
(2) Date: Apr. 9, 2015

(87) PCT Pub. No.: WO2014/059232
PCT Pub. Date: Apr. 17, 2014

(65) Prior Publication Data
US 2015/0274672 A1    Oct. 1, 2015

Related U.S. Application Data

(60) Provisional application No. 61/712,334, filed on Oct. 11, 2012, provisional application No. 61/731,625, filed on Nov. 30, 2012.

(51) Int. Cl.
| | | |
|---|---|---|
| *C07D 401/12* | (2006.01) | |
| *C07D 491/107* | (2006.01) | |
| *C07D 221/20* | (2006.01) | |
| *C07D 201/04* | (2006.01) | |
| *C07D 401/04* | (2006.01) | |
| *C07D 405/10* | (2006.01) | |

(52) U.S. Cl.
CPC ......... *C07D 221/20* (2013.01); *C07D 401/04* (2013.01); *C07D 401/12* (2013.01); *C07D 405/10* (2013.01); *C07D 491/107* (2013.01)

(58) Field of Classification Search
CPC  C07D 221/20; C07D 401/04; C07D 491/107; C07D 405/10
USPC ............................................. 546/16; 514/274
See application file for complete search history.

(56) References Cited

U.S. PATENT DOCUMENTS

| | | | |
|---|---|---|---|
| 2003/0055244 A1 | 3/2003 | Scarborough et al. | |
| 2010/0292212 A1 | 11/2010 | Ackermann et al. | |
| 2011/0166124 A1 | 7/2011 | McCormick et al. | |
| 2011/0257213 A1 | 10/2011 | Gao et al. | |
| 2015/0218187 A1* | 8/2015 | Koul ................... | C07D 413/14 |
| | | | 514/210.18 |

FOREIGN PATENT DOCUMENTS

| | | | |
|---|---|---|---|
| WO | WO2010048207 A2 | 4/2010 | |
| WO | WO2010080537 A1 | 4/2010 | |
| WO | WO2010129729 A1 | 11/2010 | |
| WO | 2012009217 | * | 1/2012 |
| WO | WO2012009217 A1 | 1/2012 | |
| WO | WO2010096093 A1 | 6/2013 | |
| WO | WO2013096093 | * | 6/2013 |
| WO | WO2014054053 | * | 10/2015 |

OTHER PUBLICATIONS

Pandey et al 2001, Spirocyclic Non-peptide IIb-IIIa Antagonists. Part 2: Design of Potent Antagonists containing the 3-azaspiro[5.5]undec-9-yl Template.*
International Search Report and Written Opinion for PCT/US2013/064472; mailed on Mar. 27, 2014; 9 pages.

* cited by examiner

Primary Examiner — Rita Desai
(74) Attorney, Agent, or Firm — Baerbel R. Brown; Catherine D. Fitch

(57) ABSTRACT

The present invention relates to a compound represented by formula (I): and pharmaceutically acceptable salts thereof are disclosed as useful for treating or preventing diabetes, hyperlipidemia, obesity, inflammation related disorders, and related diseases and conditions. The compounds are useful as agonists of the G-protein coupled receptor GPR120. Pharmaceutical compositions and methods of treatment are also included.

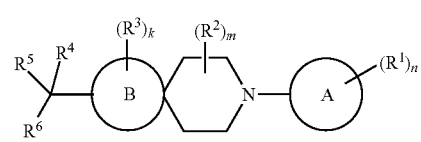

10 Claims, No Drawings

SUBSTITUTED SPIROPIPERIDINYL COMPOUNDS USEFUL AS GPR120 AGONISTS

BACKGROUND OF THE INVENTION

The present invention relates to substituted spiropiperidinyl derivatives that are useful in the pharmaceutical field. The compounds act as GPR120 receptor function regulating agents (modulators), which are useful as drugs for treating and/or preventing diabetes, obesity, hyperlipidemia, and inflammation related disorders.

GPR120, a G protein-coupled receptor, causes intracellular signaling through binding with unsaturated long chain fatty acids, such as alpha-linoleic acid, to induce various biological reactions. Actions of GPR120 and its ligand have been reported to promote secretion of glucagon-like-peptide-1 ("GLP-1") functions to reduce blood glucose level in gastrointestinal cell lines. see Nature Medicine, 2005, 11(1), 90-94. GLP-1, which is a peptide hormone, has been found to induce insulin secretion depending on a blood glucose level. GLP-1 is also suggested to be efficacious for delaying the apoptosis of beta cells in type II diabetes mellitus.

GPR120 is expressed in adipocytes. GPR120 has been found to be increasingly expressed by adipose differentiation induction. In addition, actions of GPR120 and one of its putative ligand have been reported to suppress lipolysis in adipose-differentiated cells. A high blood lipid level is known to be one of the causes of insulin resistance. Suppression of lipolysis by a GPR120 agonist is thus expected to decrease the level of free fatty acid in blood to normalize a blood lipid level, resulting in improvement in insulin resistance.

GPR120 is also expressed in the pituitary gland, and a GPR120 ligand is reported to suppress adrenocorticotropic hormone secretion. Adrenocorticotropic hormone promotes glucocorticoid secretion downstream thereof to induce action such as promotion of glyconeogenesis in the liver, inhibitory action against glucose uptake in muscle and peripheral tissue, lipolysis in adipose tissue or release of fatty acid or glycerol. Accordingly, GPR120 is considered to exhibit hypoglycemic action or blood lipid lowering action via suppression action against adrenocorticotropic hormone secretion even in the central nervous system.

Recently, GPR120 has been shown to play a role in obesity in both mice and humans. GPR120 knockout mice fed a high fat diet developed obesity, glucose intolerance and fatty liver with decreased adipocyte differentiation and lipogenesis and enhanced hepatic lipogenesis. In the study, insulin resistance in such mice was associated with reduced insulin signaling and enhanced inflammation in adipose tissue. In human, GPR120 expression in adipose tissue is significantly higher in obese individuals than in lean controls. See Ichimura, et al., Nature, 2012, 483, 350-54; and Cintra, et al., Plos One, 2012, 7(1), 1-15.

GPR120 has also been shown to play a role in inflammation. Wild-type mice treated with omega-3 fatty acids inhibited macrophage-induced tissue inflammation and enhanced systemic insulin sensitivity. However, this effect was not observed in GPR120 knockout mice. See Oh, et al., Cell, 2010, 142, 687; and Talukar, et al., Trends in Pharmacological Sciences, 2011, 32(9), 543-550.

In light of the above description, a compound having GPR120 agonist activity is considered to be useful as an agent for treating and/or preventing diabetes mellitus, obesity, hyperlipidemia, and inflammation related disorders.

SUMMARY OF THE INVENTION

The present invention relates to compounds represented by formula I:

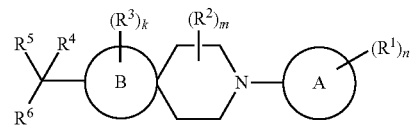

I as well as pharmaceutically acceptable salts thereof, and pharmaceutical compositions comprising a compound of formula I.

The present invention further relates to methods of treating diabetes, obesity, hyperlipidemia, inflammation related disorders, and related diseases and conditions, comprising administering a compound of formula I to a patient in need thereof.

DETAILED DESCRIPTION OF THE INVENTION

The present invention relates to compounds represented by formula I:

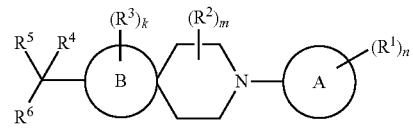

I or a pharmaceutically acceptable salt thereof, wherein:
ring A is phenyl, pyridinyl, or pyrimidinyl;
ring B is a $(C_{5-6})$cycloalkyl, cyclohexenyl, or a 5- or 6-membered heterocycloalkyl containing 1 O ring atom, wherein ring B forms a spiro ring system with the adjoining piperidinyl ring;
each $R^1$ is
(1) halo,
(2) $(C_{1-6})$alkyl,
(3) halo$(C_{1-6})$alkyl,
(4) $(C_{1-6})$alkoxy,
(5) halo$(C_{1-6})$alkoxy,
(6) hydroxy$(C_{1-3})$alkyl,
(7) $(C_{1-2})$alkoxy-$(C_{1-6})$alkoxy,
(8) $(C_{1-6})$alkyl-S(O)$_q$—,
(9) halo$(C_{1-6})$alkyl-S(O)$_q$—,
(10) $(C_{3-7})$cycloalkyl-S(O)$_q$—,
(11) nitro,
(12) $(C_{3-7})$cycloalkyl,
(13) $(C_{3-7})$cycloalkyl-O—,
(14) cyano,
(15) hydroxy,
(16) $(C_{1-6})$alkylC(O)—,
(17) amino,
(18) $(C_{1-6})$alkylN(H)—,
(19) $((C_{1-6})$alkyl$)_2$N—,
(20) phenyl;
(21) phenoxy,

(22) 4- to 7-membered heterocycloalkyl ring, containing 1-3 O, N, or S ring atoms, or

(23) 5- or 6-membered heteroaryl ring, containing 1-3 O, N, or S ring atoms,

(24) 5- or 6-membered heteroaryloxy ring, containing 1-3 O, N, or S ring atoms, wherein the phenyl, phenoxy, heteroaryl, heteroaryloxy, heterocycloalkyl groups are optionally substituted by 1-3 $(C_{1-6})$alkyl, halo$(C_{1-6})$alkyl, or halo, or alternatively two $R^1$ groups are linked together with the carbon to which they are both attached to form a 5- or 6-membered monocyclic heterocyclic ring, containing 1-3 O, N, and S ring atoms, wherein the heterocyclic ring is optionally substituted by 1-3 $(C_{1-6})$alkyl, halo$(C_{1-6})$alkyl groups, or halo groups.

each $R^2$ and $R^3$ are independently (1) $(C_{1-6})$alkyl, (2) halo$(C_{1-6})$alkyl, (3) $(C_{1-6})$alkoxy, (4) halo$(C_{1-6})$alkoxy, (5) hydroxyl, or (6) halo;

$R^4$ and $R^5$ are independently (1) hydrogen, (2) $(C_{1-6})$alkyl, (3) halo$(C_{1-6})$alkyl, or (4) halo;

$R^6$ is (1) COOH, (2) tetrazolyl, (3) —$(C_{1-3})$alkylCOOH, (4) $(C_{1-4})$alkylNH$_2$, or (5) $(C_{1-4})$alkylOH;

q is 0, 1, or 2;

k is 0, 1, 2, or 3;

m is 0, 1, 2, or 3; and n is 0, 1, 2, 3 or 4.

In one embodiment, ring A is phenyl. In one embodiment, ring A is pyridinyl or pyrimidinyl. In one embodiment, ring A is pyridinyl. In one embodiment, ring A is pyrimidinyl.

In one embodiment, ring B is $(C_{5-6})$cycloalkyl, wherein ring B forms a spiro ring system with the adjoining piperidinyl ring. In one class of this embodiment, k is 0. In one class of this embodiment, ring B is a cyclopentyl ring, wherein cyclopentyl ring forms a spiro ring system with the adjoining piperidinyl ring. In one subclass of this class, k is 0. In one class of this embodiment, ring B is a cyclohexyl ring, wherein the cyclohexyl ring forms a spiro ring system with the adjoining piperidinyl ring. In one subclass of this class, k is 0.

In one embodiment, ring B is cyclohexenyl ring, wherein the cyclohexenyl ring forms a spiro ring system with the adjoining piperidinyl ring. In one class of this embodiment, k is 0.

In one embodiment, ring B is 5- or 6-membered heterocycloalkyl containing 1 O ring atom. In one class of this embodiment, k is 0. In one class of this embodiment, ring B is a tetrahydropyranyl ring, wherein the tetrahydropyranyl ring forms a spiro ring system with the adjoining piperidinyl ring. In one subclass of this class, k is 0. In one class of this embodiment, ring B is a tetrahydrofuranyl ring, whereing the tetrahydrofuranyl ring forms a spiro ring system with the adjoining piperidinyl ring. In one subclass of this class, k is 0.

In one embodiment,

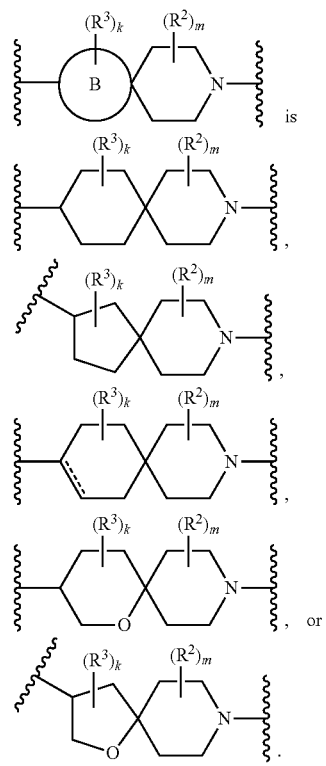

In one class of this embodiment, k and m are 0. In one class of this embodiment,

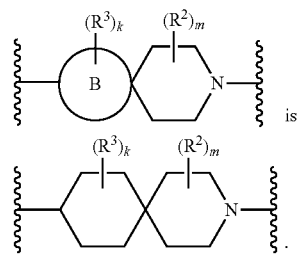

In one subclass of this class, k and m are 0. In one class of this embodiment,

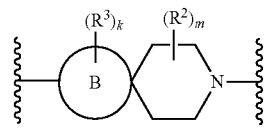

is

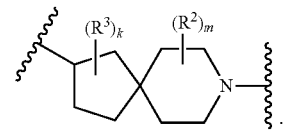

In one subclass of this class, k and m are 0. In one class of this embodiment,

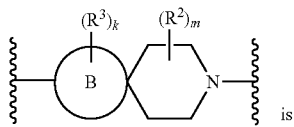

is

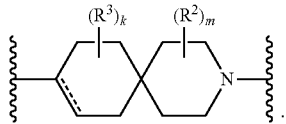

In one subclass of this class, k and m are 0. In one class of this embodiment,

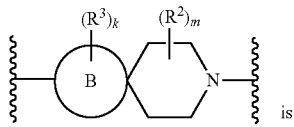

is

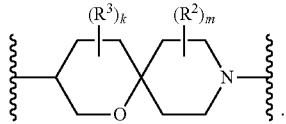

In one subclass of this class, k and n are 0. In one class of this embodiment,

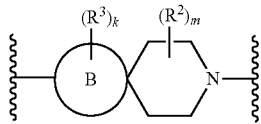

is

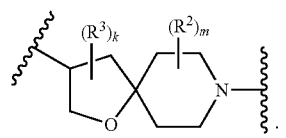

In one subclass of this class, k and m are 0.

In one embodiment, the invention relates to compounds of formula I, or a pharmaceutically acceptable salt, thereof, wherein

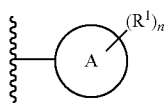

is

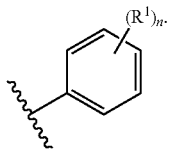

In one embodiment,

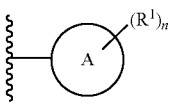

is

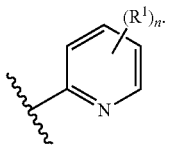

In one embodiment,

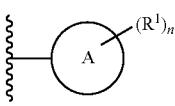

is

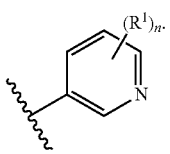

In one embodiment,

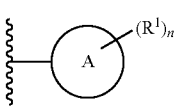

is

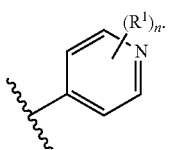

In one embodiment,
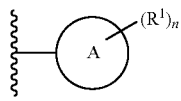
is
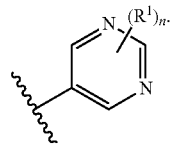
In one embodiment,
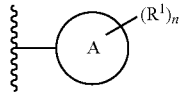
is
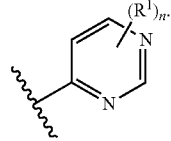
In one embodiment,
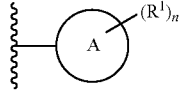
is
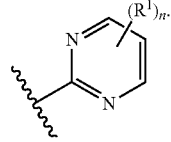
In one embodiment, the invention relates to compounds of formula I, or a pharmaceutically acceptable salt, thereof, wherein
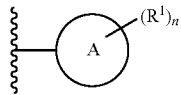
is
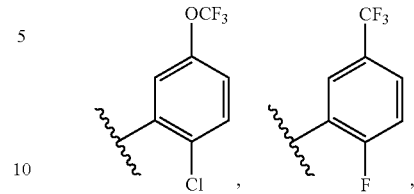
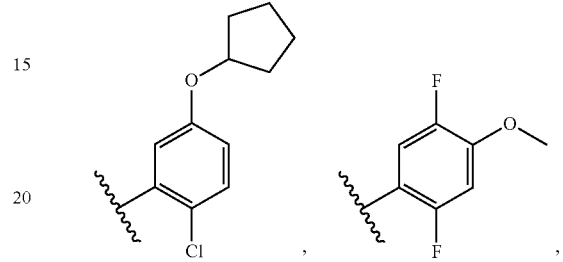
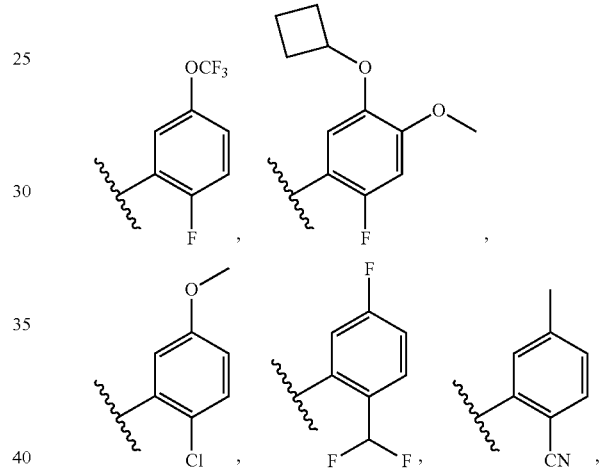
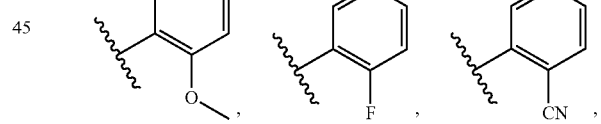
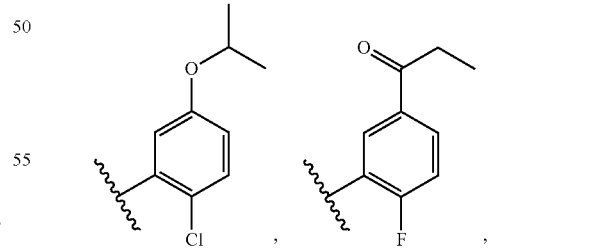

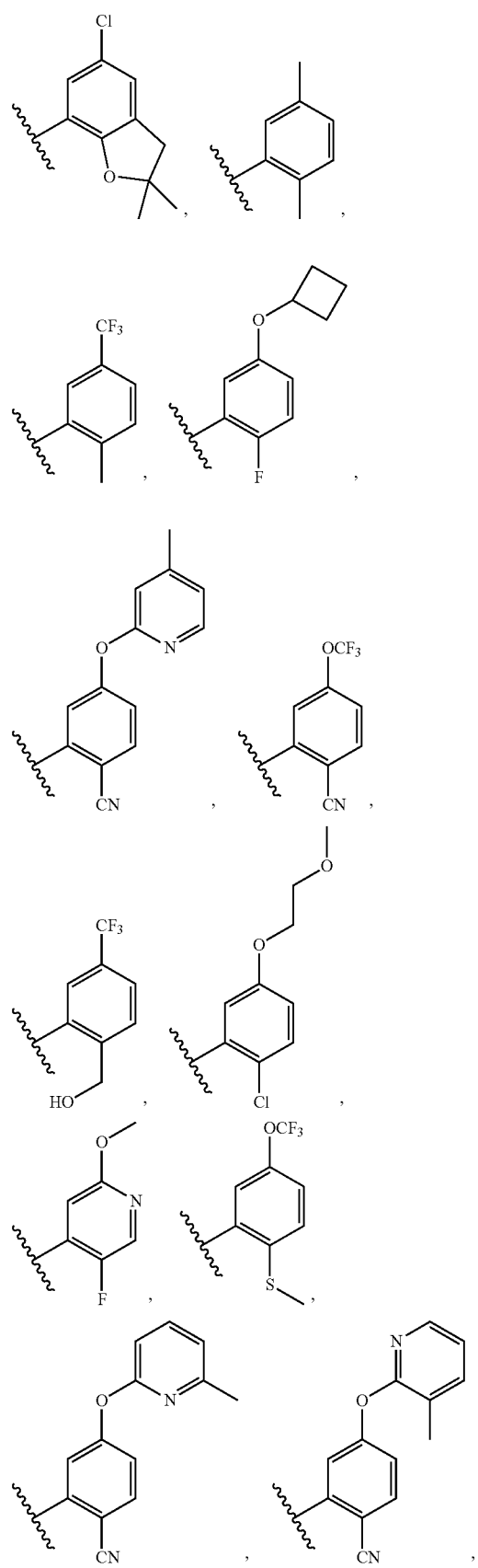
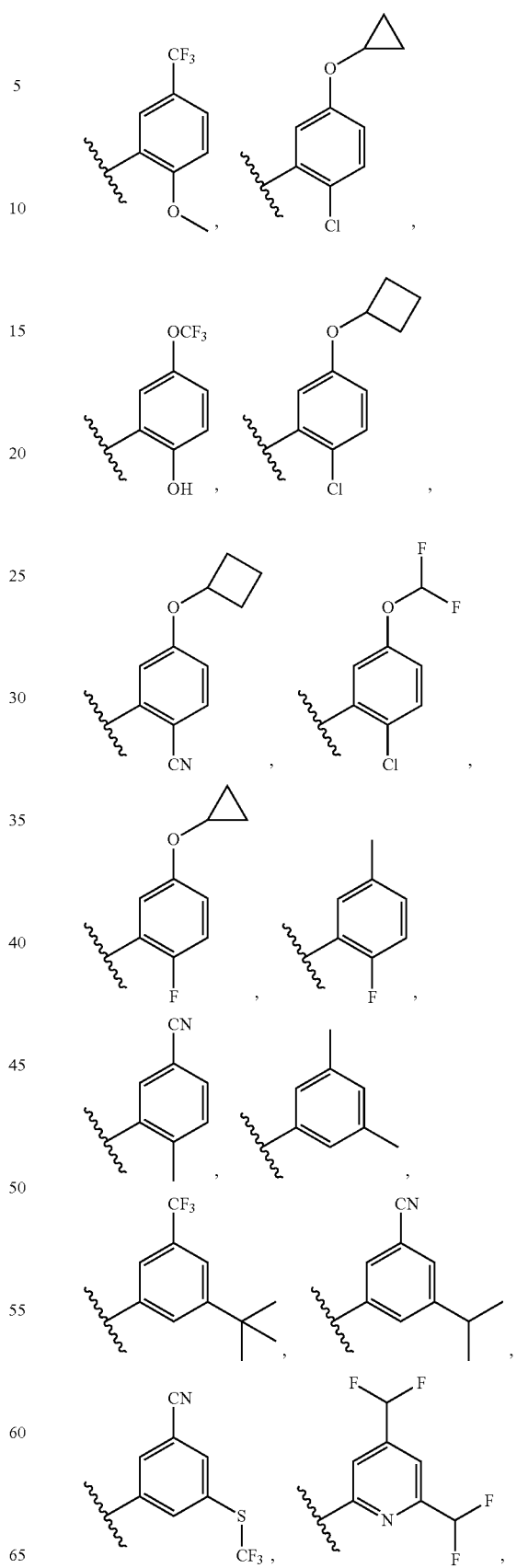

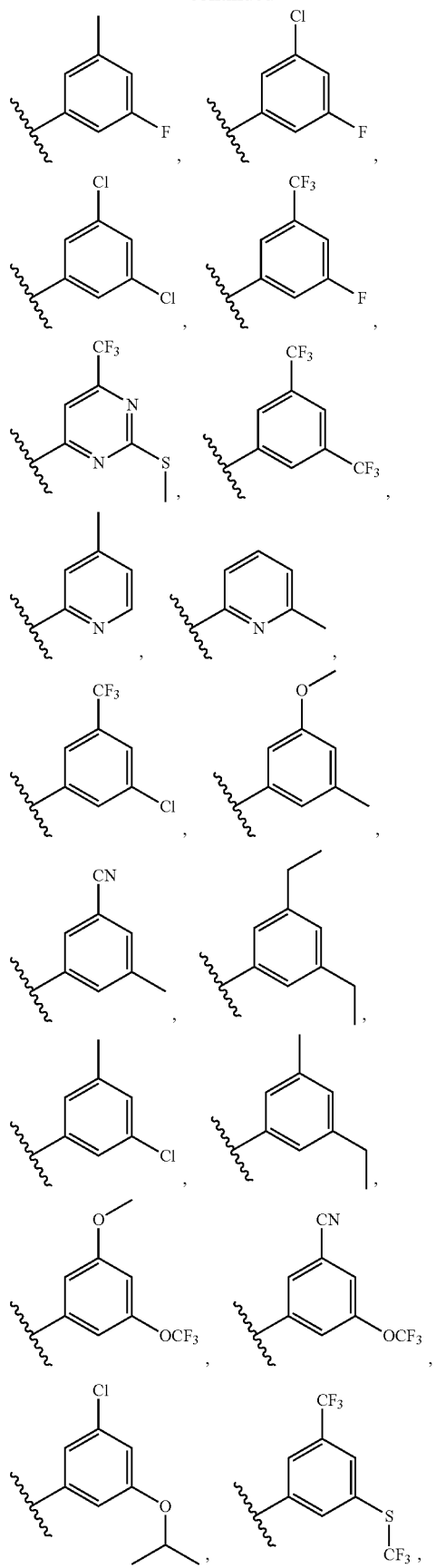
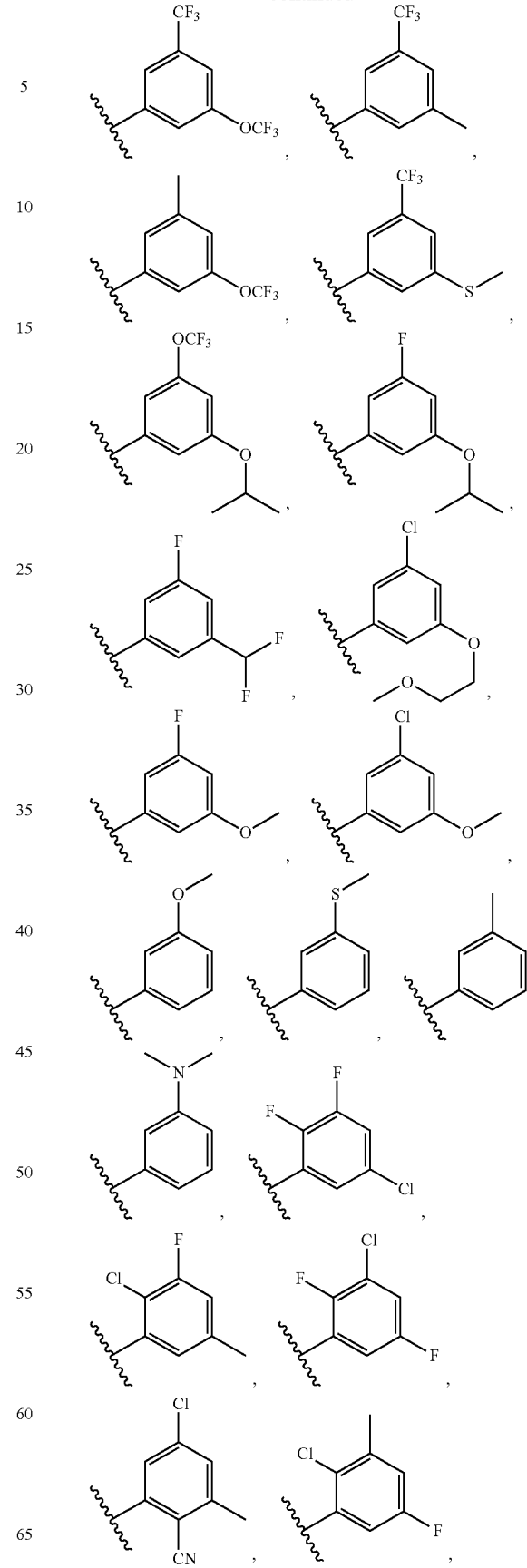

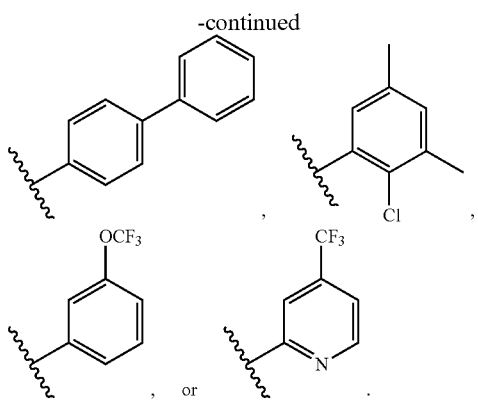

In one embodiment, each R¹ is halo, $(C_{1-6})$alkyl, halo$(C_{1-6})$alkyl, hydroxy$(C_{1-6})$alkyl, $(C_{1-6})$alkoxy, halo$(C_{1-6})$alkoxy, $(C_{1-2})$alkoxy-$(C_{1-6})$alkoxy, $(C_{1-6})$alkyl-S—, halo$(C_{1-6})$alkyl-S—, nitro, $(C_{3-7})$cycloalkyl-O—, cyano, hydroxy, $(C_{1-6})$alkylC(O)—, $((C_{1-6})$alkyl$)_2$N—, phenyl, 5- or 6-membered heteroaryloxy ring, containing 1-3 O, N, and S ring atoms, wherein the phenyl and heteroaryloxy, groups are optionally substituted by 1-3 $(C_{1-6})$alkyl, halo$(C_{1-6})$alkyl, or halo groups; or alternatively two R¹ groups are linked together with the carbon to which they are both attached to form a 5- or 6-membered monocyclic heterocyclic ring, containing 1 to 3 O, N, and S ring atoms, wherein the heterocyclic ring is optionally substituted by 1-3 $(C_{1-6})$ alkyl, halo$(C_{1-6})$alkyl groups, halo. In one class of this embodiment, two R¹ groups are linked together with the carbon to which they are both attached to form

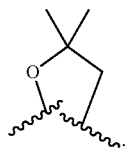 [SMILES: *CC(C)(C)O*]

In one embodiment, each R¹ is chloro, fluoro, methyl, ethyl, isopropyl, t-butyl, trifluoromethyl, difluoromethyl, cyano, methoxy, methyl-S—, difluoromethoxy, trifluoromethoxy, trifluoromethyl-S—, methyl-O-ethoxy-, hydroxymethyl, isoproproxy, cyclobutoxy, cyclopropoxy, cyclopentyloxy, ethylC(O)—, dimethylamine, hydroxy, nitro, 3-methyl-pyridinyl-O—, 6-methyl-pyridinyl-O—, 5-methyl-pyridinyl-O—, or phenyl, or two R¹ groups are linked together with the carbon to which they are both attached to form

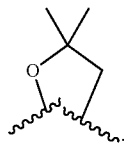

In one class of this embodiment, ring A is phenyl. In one class of this embodiment, ring A is pyridinyl. In one class of this embodiment, ring A is pyrimidinyl.

In one embodiment, each R² and R³ are independently methyl, trifluoromethyl, trifluoromethoxy, fluoro, or hydroxyl.

In one embodiment, R⁶ is COOH. In one class of this embodiment, R⁴ is hydrogen, and R⁵ is hydrogen. In one class of this embodiment, R⁴ is hydrogen, and R⁵ is methyl. In one embodiment, R⁶ is tetrazolyl. In one class of this embodiment, R⁴ is hydrogen, and R⁵ is hydrogen. In one class of this embodiment, R⁴ is hydrogen, and R⁵ is methyl. In one embodiment, R⁶ is —$(C_{1-2})$alkylCOOH. In one class of this embodiment, R⁴ is hydrogen, and R⁵ is hydrogen. In one class of this embodiment, R⁴ is hydrogen, and R⁵ is methyl. In one embodiment, R⁶ is CH₂OH. In one class of this embodiment, R⁴ is hydrogen, and R⁵ is hydrogen. In one class of this embodiment, R⁴ is hydrogen, and R⁵ is methyl. In one embodiment, R⁶ is CH₂NH₂. In one class of this embodiment, R⁴ is hydrogen, and R⁵ is hydrogen. In one class of this embodiment, R⁴ is hydrogen, and R⁵ is methyl.

In one embodiment, R⁴ is hydrogen. In one class of this embodiment, R⁵ is hydrogen, methyl, fluoro or trifluoromethyl.

In one embodiment, q is 0. In one embodiment, q is 1. In one embodiment, q is 2.

In one embodiment, k is 0. In one embodiment, k is 1. In one embodiment, k is 2. In another embodiment, k is 3.

In one embodiment, m is 0. In one embodiment, m is 1. In one embodiment, m is 2. In another embodiment, m is 3.

In one embodiment, n is 1, 2, or 3. In one embodiment, n is 0. In one embodiment, n is 1. In one embodiment, n is 2. In one embodiment, n is 3. In another embodiment, n is 4.

In one embodiment, ring A is phenyl, and ring B is $(C_{5-6})$cycloalkyl, wherein ring B forms a spiro ring system with the adjoining piperidinyl ring. In one class of this embodiment, R⁶ is COOH. In one embodiment, ring A is phenyl, and ring B is a cyclopentyl ring, wherein cyclopentyl ring forms a spiro ring system with the adjoining piperidinyl ring. In one class of this embodiment, R⁶ is COOH. In one embodiment, ring A is phenyl, and ring B is a cyclohexyl ring, wherein the cyclohexyl ring forms a spiro ring system with the adjoining piperidinyl ring. In one class of this embodiment, R⁶ is COOH. In one embodiment, ring A is phenyl, and, ring B is cyclohexenyl ring, wherein the cyclohexenyl ring forms a spiro ring system with the adjoining piperidinyl ring. In one class of this embodiment, R⁶ is COOH. In one embodiment, ring A is phenyl, and ring B is a tetrahydropyranyl ring, wherein the tetrahydropyranyl ring forms a spiro ring system with the adjoining piperidinyl ring. In one class of this embodiment, R⁶ is COOH. In one embodiment, ring A is phenyl, and, ring B is a tetrahydrofuranyl ring, whereing the tetrahydrofuranyl ring forms a spiro ring system with the adjoining piperidinyl ring. In one class of this embodiment, R⁶ is COOH.

In one embodiment, ring A is pyridinyl, and ring B is $(C_{5-6})$cycloalkyl, wherein ring B forms a spiro ring system with the adjoining piperidinyl ring. In one class of this embodiment, R⁶ is COOH. In one embodiment, ring A is pyridinyl, and ring B is a cyclopentyl ring, wherein cyclopentyl ring forms a spiro ring system with the adjoining piperidinyl ring. In one class of this embodiment, R⁶ is COOH. In one embodiment, ring A is pyridinyl, and ring B is a cyclohexyl ring, wherein the cyclohexyl ring forms a spiro ring system with the adjoining piperidinyl ring. In one class of this embodiment, R⁶ is COOH. In one embodiment, ring A is pyridinyl, and, ring B is cyclohexenyl ring, wherein the cyclohexenyl ring forms a Spiro ring system with the adjoining piperidinyl ring. In one class of this embodiment, R⁶ is COOH. In one embodiment, ring A is pyridinyl, and ring B is a tetrahydropyranyl ring, wherein the tetrahydropyranyl ring forms a spiro ring system with the adjoining piperidinyl ring. In one class of this embodiment, R⁶ is COOH. In one embodiment, ring A is pyridinyl, and, ring B is a tetrahydrofuranyl ring, whereing the tetrahydrofuranyl ring forms a spiro ring system with the adjoining piperidinyl ring. In one class of this embodiment, $R^6$ is COOH.

In one embodiment, ring A is pyrimidinyl, and ring B is $(C_{5-6})$cycloalkyl, wherein ring B forms a spiro ring system with the adjoining piperidinyl ring. In one class of this embodiment, $R^6$ is COOH. In one embodiment, ring A is pyrimidinyl, and ring B is a cyclopentyl ring, wherein cyclopentyl ring forms a spiro ring system with the adjoining piperidinyl ring. In one class of this embodiment, $R^6$ is COOH. In one embodiment, ring A is pyrimidinyl, and ring B is a cyclohexyl ring, wherein the cyclohexyl ring forms a spiro ring system with the adjoining piperidinyl ring. In one class of this embodiment, $R^6$ is COOH. In one embodiment, ring A is pyrimidinyl, and ring B is cyclohexenyl ring, wherein the cyclohexenyl ring forms a spiro ring system with the adjoining piperidinyl ring. In one class of this embodiment, $R^6$ is COOH. In one embodiment, ring A is pyrimidinyl, and ring B is a tetrahydropyranyl ring, wherein the tetrahydropyranyl ring forms a spiro ring system with the adjoining piperidinyl ring. In one class of this embodiment, $R^6$ is COOH. In one embodiment, ring A is pyrimidinyl, and ring B is a tetrahydrofuranyl ring, whereing the tetrahydrofuranyl ring forms a spiro ring system with the adjoining piperidinyl ring. In one class of this embodiment, $R^6$ is COOH.

In one embodiment, the invention relates to compounds of formula I-A:

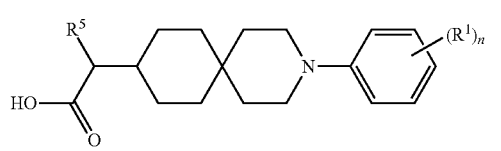

I-A or a pharmaceutically acceptable salt thereof, wherein $R^1$, $R^5$, or n are as previously defined.

In one embodiment, the invention relates to compounds of formula I-B:

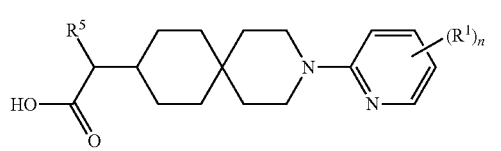

I-B or a pharmaceutically acceptable salt thereof, wherein $R^1$, $R^5$, or n are as previously defined.

In one embodiment, the invention relates to compounds of formula I-C:

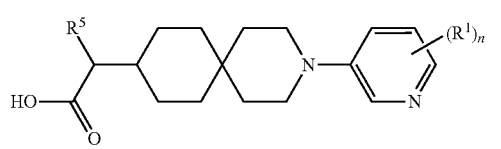

I-C or a pharmaceutically acceptable salt thereof, wherein $R^1$, $R^5$, or n are as previously defined.

In one embodiment, the invention relates to compounds of formula I-D:

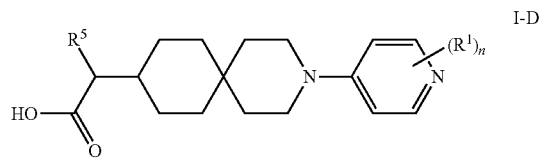

I-D or a pharmaceutically acceptable salt thereof, wherein $R^1$, $R^5$, or n are as previously defined.

In one embodiment, the invention relates to compounds of formula I-E:

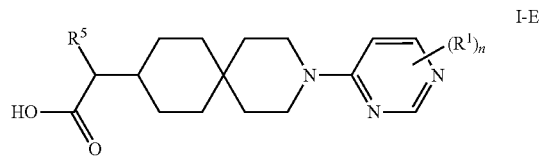

I-E or a pharmaceutically acceptable salt thereof, wherein $R^1$, $R^5$, or n are as previously defined.

In one embodiment, the invention relates to compounds of formula I-F:

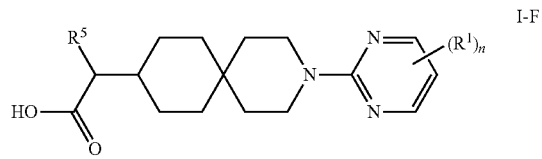

I-F or a pharmaceutically acceptable salt thereof, wherein $R^1$, $R^5$, or n are as previously defined.

In one embodiment, the invention relates to compounds of formula I-G:

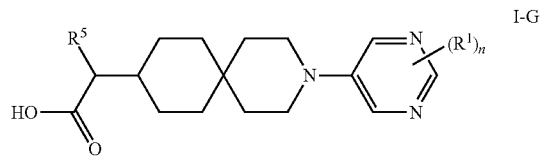

I-G or a pharmaceutically acceptable salt thereof, wherein $R^1$, $R^5$, or n are as previously defined.

The present invention also relates to a GPR120 function regulating agent containing a compound represented by the formula I or a pharmaceutically acceptable salt thereof as an active ingredient. Particularly, the present invention relates to a GPR120 agonist containing a compound represented by the formula I or a pharmaceutically acceptable salt thereof as an active ingredient.

The present invention also relates to an agent for treating and/or preventing diabetes, obesity, hyperlipidemia, or an inflammation related disorder, containing a compound represented by the formula I or the pharmaceutically acceptable salt thereof, as an active ingredient.

Furthermore, the present invention relates to a pharmaceutical composition containing the compound represented by the formula I and the pharmaceutically acceptable carrier.

The present invention also relates a compound represented by the formula I for use as a medicament.

The present invention relates to the use of a compound represented by formula I or a pharmaceutically acceptable salt thereof, in the manufacture of a medicament for use in treating a condition selected from the group consisting of diabetes, hyperlipidemia, obesity, and inflammation related disorders.

The present invention relates to the treatment of a condition selected from the group consisting of diabetes, hyperlipidemia, obesity, and inflammation related disorders comprising administering to an individual a pharmaceutical composition comprising the compound represented by formula I.

A compound according to an embodiment of the present invention or the pharmaceutically acceptable salt thereof has a strong GPR120 function regulating action, particularly an agonist action, and is useful for treating and/or preventing diabetes, obesity, hyperlipidemia, or an inflammation related disorder.

The invention is described herein in detail using the terms defined below unless otherwise specified.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" refers to an alkyl group linked to oxygen.

"Halogen" (Halo) includes fluorine, chlorine, bromine and iodine.

"Cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Cycloalkoxy" and "cycloalkyo-O" are used interchangeably and refer to a cycloalkyl group, as defined above, linked to oxygen.

"Haloalkyl" include mono-substituted as well as multiple halo substituted alkyl groups, up to perhalo substituted alkyl. For example, trifluoromethyl is included.

"Haloalkoxy" and "haloalkyl-O" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Heterocyclyl" "heterocycle" or "heterocyclic" refers to nonaromatic cyclic ring structures in which one or more atoms in the ring, the heteroatom(s), is an element other than carbon. Heteroatoms are typically O, S or N atoms. Examples of heterocyclyl groups include: piperidine, piperazine, morpholine, pyrrolidine, tetrahydrofuran, azetidine, oxirane, or aziridine, and the like.

"Heteroaryl" refers to aromatic or partially aromatic cyclic ring structures in which one or more atoms in the ring, the heteroatoms(s), is an element other than carbon. Heteroatoms are typically O, S, or N atoms. Examples of heteroaromatic groups include: pyridine, pyrimidinyl, pyrrole, pyridazine, isoxazole, indole, or imidazole.

"Alkyl-S(O)$_q$" refers to an alkyl group linked to a sulfur atom. The sulfur atom is attached 0-2 oxygen atom(s) depending on the definition of the variable q. When q is 0, the group is a thio-alkoxy (alkyl-S—). When q is 1, the group is an alkyl-sulfoxide (alkyl-S(O)—). When q is 2, the group is an alkyl sulfone (alkyl-S(O)$_2$—).

"Haloalkyl-S(O)$_q$" refers to a "alkyl-S(O)$_q$" as defined above whereby one or more hydrogen atoms on the alkyl group is replaced by a halogen group.

"Cycloalkyl-S(O)$_q$" refers to a cycloalkyl group linked to a sulfur atom. The sulfur atom is attached to 0-2 oxygen atoms(s) depending on the definition of the variable q. When q is 0, the group is a thio-cycloalkoxy (Cycloalkyl-S—). When q is 1, the group is a cycloalkyl-sulfoxide (cycloalkyl-S(O)—). When q is 2, the group is a cycloalkyl-sulfone (cycloalkyl-S(O)$_2$).

"AlkylC(O)" refers to an alkyl group linked to a carbonyl group.

"Alkoxy-alkoxy" refers to an alkoxy linked to another alkoxy. A nonlimiting example is 2-methoxyethoxy.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods.

These include chiral chromatography, derivatization with a chiral auxiliary followed by separation by chromatography or crystallization, and fractional crystallization of diastereomeric salts.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of Formula I and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Compounds of the present invention are potent agonists of the GPR120 receptor. These compounds and pharmaceutically acceptable salts thereof are modulators of the receptor known as GPR120, and are therefore useful in the treatment of diseases that are modulated by GPR120 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(7) hypercholesterolemia;
(8) hypertriglyceridemia (elevated levels of triglyceride-rich-lipoproteins);
(9) mixed or diabetic dyslipidemia;
(10) low HDL cholesterol;
(11) high LDL cholesterol;
(12) Hyperapobetalipoproteinemia;
(13) atherosclerosis;
(14) inflammation related disorders;
(15) type 1 diabetes; and
(16) insulin resistance.

Because the compounds are agonists of the GPR120 receptor, the compounds will be useful for lowering glucose, lipids, and insulin resistance and increasing insulin sensitivity in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for increasing insulin sensitivity. The compounds are useful for treating or preventing gestational diabetes.

Additionally, by keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds of this invention are useful in treating inflammation related disorders such as obesity, diabetes, cancer, and cardiovascular disease.

The compounds, compositions, and medicaments as described herein are further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia. One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat) or a monoamine neurotransmitter uptake inhibitor (e.g., sibutramine or phentermine). The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors (e.g., sitagliptin, alogliptin, MK-3102, linagliptin, vildagliptin);

(b) insulin sensitizers selected from the group consisting of (i) PPAR agonists and (ii) biguanides;

(c) insulin and insulin mimetics (e.g., insulin degludec, insulin glargine, insulin lispro);

(d) sulfonylureas and other insulin secretagogues;

(e) α-glucosidase inhibitors;

(f) glucagon receptor antagonists;

(g) GLP-1, GLP-1 mimetics, and GLP-1 receptor agonists (e.g., dulaglutide, exenatide, semaglutide, albiglutide, liraglutide, lixisenatide, taspoglutide);

(h) GIP,GIP mimetics, and GIP receptor agonists;

(i) PACAP, PACAP mimetics, and PACAP receptor 3 agonists;

(j) cholesterol lowering agents selected from the group consisting of
(i) HMG-CoA reductase inhibitors, (ii) sequestrants, (iii) nicotinyl alcohol, nicotinic acid and salts thereof, (iv) PPARα agonists, (v) PPAR α/γ dual agonists (e.g., aleglitazar), (vi) inhibitors of cholesterol absorption, (vii) acyl CoA:cholesterol acyltransferase inhibitors, and (viii) anti-oxidants;

(k) PPARδ agonists;

(l) SGLT inhibitors (e.g., empagliflozin, dapagliflozin, canagliflozin, BI-10773, tofogliflozin, ipragliflozin, LX-4211, PF-4971729, remogloflozin, TS-071);

(m) antiobesity compounds;

(n) ileal bile acid transporter inhibitors;

(o) anti-inflammatory agents excluding glucocorticoids;

(p) protein tyrosine phosphatase-1B (PTP-1B) inhibitors; and (q) antihypertensives including those acting on the angiotensin or renin systems, such as angiotensin converting enzyme inhibitors, angiotensin II receptor antagonists or renin inhibitors, (e.g., lisinopril, losartan); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of formula I or the other drugs may have utility, where the combination of the drugs together are safer or more effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, omarigliptin, linagliptin, vildagliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., MK-3577, MK-0893, LY-2409021 and KT6-971);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;

(21) other agonists of the G-protein-coupled receptors: (i) GPR-109, (ii) GPR-119 (e.g., MBX2982 and PSN821), and (iii) GPR-40 (e.g., TAK875);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab); and
(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), MK-3102, SYR-472, teneligliptin, KRP104, TS021, AMG222, SK0403, LC15-0444, vildagliptin, saxagliptin, alogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other GPR-40 agonists that can be used in combination with compounds of the formulas described herein include, but are not limited to:
(1) 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol1-oxide
(2) 5-(4-((3-(2,6-dimethyl-4-(3-(methylsulfonyl)propoxy)phenyl)phenyl)methoxy)phenyl)isothiazole-3-ol1-oxide;
(3) 5-(4-((3-(2-methyl-6-(3-hydroxypropoxy)pyridine-3-yl)-2-methylphenyl)methoxy)phenyl) isothiazole-3-ol1-oxide; and
(4) 5-[4-[[3-[4-(3-aminopropoxy)-2,6-dimethylphenyl]phenyl]methoxy]phenyl]isothiazole-3-ol1-oxide, and
pharmaceutically acceptable salts thereof.

Other dipeptidyl peptidase-IV (DPP-4) inhibitors that can be used in combination with compounds of the formulas described herein include, but are not limited to:
(1) (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;
(2) (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;
(3) (2R,3S,5R)-2-(2,5-difluorophenyl)tetrahydro)-5-(4,6-dihydropyrrolo[3,4-c]pyrazol-5(1H)-yl)tetrahydro-2H-pyran-3-amine;
(4) (3R)-4-[(3R)-3-amino-4-(2,4,5-trifluorophenyl)butanoyl]-hexahydro-3-methyl-2H-1,4-diazepin-2-one;
(5) 4-[(3R)-3-amino-4-(2,5-difluorophenyl)butanoyl]hexahydro-1-methyl-2H-1,4-diazepin-2-one hydrochloride; and
(6) (3R)-4-[(3R)-3-amino-4-(2,4,5-trifluorophenyl)butanoyl]-hexahydro-3-(2,2,2-trifluoroethyl)-21,4-diazepin-2-one; and
pharmaceutically acceptable salts thereof.

Antiobesity compounds that can be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging anti-obesity drugs," *Expert Opin. Emerging Drugs*, 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmaceutical therapies for obesity," *Exp. Opin. Pharmacother.*, 10: 921-925 (2009).

Glucagon receptor antagonists that can be used in combination with the compounds of formula I include, but are not limited to:
(1) N-[4-((1S)-1-{3-(3,5-dichlorophenyl)-5-[6-(trifluoromethoxy)-2-naphthyl]-1H-pyrazol-1-yl}ethyl)benzoyl]-β-alanine;
(2) N-[4-((1R)-1-{3-(3,5-dichlorophenyl)-5-[6-(trifluoromethoxy)-2-naphthyl]-1H-pyrazol-1-yl}ethyl)benzoyl]-β-alanine;
(3) N-(4-{1-[3-(2,5-dichlorophenyl)-5-(6-methoxy-2-naphthyl)-1H-pyrazol-1-yl]ethyl}benzoyl)-β-alanine;
(4) N-(4-{(1S)-1-[3-(3,5-dichlorophenyl)-5-(6-methoxy-2-naphthyl)-1H-pyrazol-1-yl]ethyl}benzoyl)-β-alanine;
(5) N-(4-{(1S)-1-[(R)-(4-chlorophenyl)(7-fluoro-5-methyl-1H-indol-3-yl)methyl]butyl}benzoyl)-β-alanine; and
(6) N-(4-{(1S)-1-[(4-chlorophenyl)(6-chloro-8-methylquinolin-4-yl)methyl]butyl}benzoyl)-β-alanine; and
pharmaceutically acceptable salts thereof.

In another aspect of the invention, a pharmaceutical composition is disclosed which comprises one or more of the following agents:
(a) a compound of structural formula I;
(b) one or more compounds selected from the group consisting of:
 (1) dipeptidyl peptidase-IV (DPP-4) inhibitors;
 (2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;
 (3) sulfonylurea and non-sulfonylurea insulin secretagogues, (e.g., tolbutamide, glyburide, glipizide, glimepiride, mitiglinide, and meglitinides, such as nateglinide and repaglinide);
 (4) α-glucosidase inhibitors (e.g., acarbose, voglibose and miglitol);
 (5) glucagon receptor antagonists;
 (6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii)

inhibitors of cholesterol absorption, (e.g., ezetimibe), and (iv) acyl CoA:cholesterol acyltransferase inhibitors (e.g., avasimibe);

(7) HDL-raising drugs, such as niacin or a salt thereof and extended-release versions thereof; MK-524A, which is a combination of niacin extended-release and the DP-1 antagonist MK-524; and nicotinic acid receptor agonists;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);

(11) glucokinase activators (GKAs) (e.g., AZD6370);

(12) inhibitors of 11β-hydroxysteroid dehydrogenase type 1 (e.g., such as those disclosed in U.S. Pat. No. 6,730, 690; WO 03/104207; and WO 04/058741);

(13) inhibitors of cholesteryl ester transfer protein (CETP), (e.g., torcetrapib and MK-0859);

(14) inhibitors of fructose 1,6-bisphosphatase (e.g., such as those disclosed in U.S. Pat. Nos. 6,054,587; 6,110, 903; 6,284,748; 6,399,782; and 6,489,476);

(15) inhibitors of acetyl CoA carboxylase-1 or 2 (ACC1 or ACC2);

(16) AMP-activated Protein Kinase (AMPK) activators;

(17) agonists of the G-protein-coupled receptors: (i) GPR-109, (ii) GPR-119 (e.g., MBX2982, and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl] isothiazole-3-ol1-oxide, 5-(4-((3-(2,6-dimethyl-4-(3-(methylsulfonyl)propoxy)phenyl)phenyl)methoxy)phenyl)isothiazole-3-ol1-oxide, 5-(4-((3-(2-methyl-6-(3-hydroxypropoxyl)pyridine-3-yl)-2-methylphenyl)methoxy)phenyl)isothiazole-3-ol1-oxide, and 5-[4-[[3-[4-(3-aminopropoxy)-2,6-dimethylphenyl]phenyl] methoxy]phenyl]isothiazole-3-ol 1-oxide);

(18) SSTR3 antagonists (e.g., such as those disclosed in WO 2009/011836);

(19) neuromedin U receptor agonists (e.g., such as those disclosed in WO2009/042053, including, but not limited to, neuromedin S (NMS));

(20) inhibitors of stearoyl-coenzyme A delta-9 desaturase (SCD);

(21) GPR-105 antagonists (e.g., such as those disclosed in WO 2009/000087);

(22) inhibitors of glucose uptake, such as sodium-glucose transporter (SGLT) inhibitors and its various isoforms, such as SGLT-1; SGLT-2 (e.g., ASP1941, TS071, BI10773, tofogliflozin, LX4211, canagliflozin, dapagliflozin and remogliflozin; and SGLT-3);

(23) inhibitors of acyl coenzyme A:diacylglycerol acyltransferase 1 and 2 (DGAT-1 and DGAT-2);

(24) inhibitors of fatty acid synthase;

(25) inhibitors of acyl coenzyme A:monoacylglycerol acyltransferase 1 and 2 (MGAT-1 and MGAT-2);

(26) agonists of the TGR5 receptor (also known as GPBAR1, BG37, GPCR19, GPR131, and M-BAR);

(28) bromocriptine mesylate and rapid-release formulations thereof, and

(29) IL-1b antibodies (e.g., XOMA052, and canakinumab); and (c) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Assays

The usefulness of the compound encompassed by formula (I) for a medicament is shown in tests described below.

The usefulness of the compound according to an embodiment of the present invention was assessed for a medicament by described methods of the following in vitro tests:

FLIPR Assay

All compounds were tested under the FLIPR assay unless otherwise indicated.

Test 1: Cloning of Genes

Primers were synthesized in the domains on the opposite sides of the base sequences of the ORFs of the known GPCR and GPR120 in GenBank Accession NOs. NM 181745 (human) and NM 181748 (mouse), and the genes were cloned by RT-PCR. The base sequences of the primers used are described below. The restriction enzymes, BamHI and EcoRI, recognition sites were introduced for subcloning, respectively.

```
hGPR120_F01:
                                (SEQ ID NO: 1)
AGGATCCGCCGCCATGTCCCCTGAATGCGCGCGGGCAG hGPR120_R01:
                                (SEQ ID NO: 2)
CGAATTCTTAGCCAGAAATAATCGACAAGTCATTTC mGPR120_F01:
                                (SEQ ID NO: 3)
AGGATCCGCCGCCATGTCCCCTGAGTGTGCACAGACGAC mGPR120_R01:
                                (SEQ ID NO: 4)
CGAATTCTTAGCTGGAAATAACAGACAAGTCATTTC
```

As samples for PCR, human small intestine Marathon-ready cDNA (CLONTECH, current corporate name: TaKaRa) and cDMA obtained by reverse transcription of mouse BAT-derived RNA were used for human and mouse GPR120 receptor genes, respectively.

Using KOD Plus (TOYOBO) for PCR, 30 cycles of 94° C. for 2 minutes, 94° C. for 15 seconds, 55° C. for 30 seconds and 68° C. for 1 minute were carried out to effect reaction, followed by addition of 0.5 units of ExTaq (Ta-KaRa) and incubation at 72° C. for 10 minutes to carry out A-addition reaction to terminals. For mouse PCR, 35 cycles were carried out on the condition of a final DMSO concentration of 2%.

Cloning of amplified PCR products was carried out using pCR2.1-TOPO TA cloning kit (Invitrogen). For verification of base sequences, electrophoresis was carried out using BigDye Terminator Cycle Sequencing Ready Reaction Kit Ver. 3.0 and 377 DNA Sequencer (Applied Biosystems) to determine the base sequences. The human GPR120 gene was 16 amino acids shorter than the sequence registered as GenBank Accession NO. NM 181745.

The GPR120 receptor genes cloned into pCR2.1-TOPO vectors, into which the restriction enzymes, BamHI and EcoRI, recognition sites were introduced, were excised from the vectors by the enzymes and subcloned into the BamHI and EcoRI recognition sites of eukaryotic expression vector EF1/V5-His B (Invitrogen).

Test 2: Production of Expression Cells

Using Lipofectamine 2000 (Invitrogen), cDNA of GPR120 receptor was transfected into CHO/NFAT-BLA cells, and drug-resistant cells were isolated to obtain GPR120 stable expression strains. The GPR120-expressed CHO cells were cultured in DMEM/F12 medium containing 10% fetal bovine serum, 100 units/ml penicillin, 0.1 mg/ml streptomycin sulfate, 250 µg/ml Zeocin, 500 µg/mL Geneticin and 15 mM HEPES.

Test 3: Measurement of Intracellular Calcium Concentration

On the day before the measurement day, CHO cells expressing human GPR120 were plated at 10000 cells per well in a 384-well black plate (#3702, Corning) and incubated overnight in a $CO_2$ incubator. On the day of the measurement, 4 µM Fluo-4 AM (fluorescence calcium indicator reagent) was incubated to be introduced into the human GPR120 expression CHO cells in the presence of 0.08% Pluronic F-127 in a $CO_2$ incubator for 90 minutes. To the cells was added the test compound diluted with HBSS solution containing 20 mM HEPES and 2.5 mM probenecid. Variations in the intracellular calcium concentration were measured by Fluorescence Imaging Plate Reader (FLIPR; Molecular Devices) to examine the agonist action, and $EC_{50}$ values were calculated. The following compound (U.S. Pat. No. 8,367,708) was used to determine 100% activation:

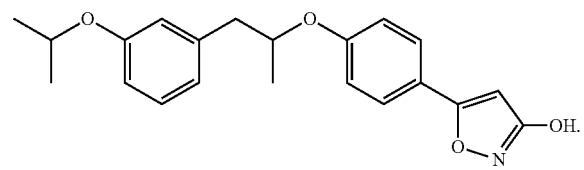 [SMILES: CC(C)Oc1cccc(CC(C)Oc2ccc(-c3cc(O)no3)cc2)c1]

The $EC_{50}$ values for the exemplified compounds are provided in the following examples and in the following tables.

IP1 Assay

IP1 assay results were obtained adapting the GPR120 assay described in C. Bergsdorf, et al., *Assay Drug Dev. Technol.*, 2008, 6(1), 39-53.

General Schemes

The compounds of the invention can be prepared using the synthetic schemes described herein as well as any of several alternate methods which will be apparent to a chemist skilled in the art.

The following abbreviations may be used in the synthetic schemes or Examples: aq. is aqueous; BOC is t-butyloxycarbony; $Boc_2O$ is di(t-butyloxy)carbonyl; C is Celsius; Calc'd is calculated; Cbz is carboxybenzy; DCM is dichloromethane; DEA is N,N-diisopropylethylamine; DMF is dimethylformamide; DMAP dimethylaminopyridine; DMEDA is N,N'-dimethylethane-1,2-diamine; DMSO is dimethylsulfoxide; EtOAc is ethyl acetate; EtOH is ethanol; ent is enantiomer; g is gram; h is hour; HPLC is high performance liquid chromatography; i-PrOH is isopropyl alcohol; KOH is potassium hydroxide; L is liter; LC is liquid chromatography; LCMS is liquid chromatography-mass spectrometry; M is molar; min is minute; mg is milligram; mL is milliliter; mmol is millimole; MTBE is methyl t-butyl ether; MVK is methylvinylketone; NMP is N-methyl-2-pyrrolidone; $Pd_2(dba)_3$ is tris(dibenzylideneacetone)dipalladium (0); rt is room temperature; SPhos is dicyclohexylphosphino-2',6'-dimethoxybiphenyl; TEA is triethylamine; TFA is trifluoroacetic acid; THF is tetrahydrofuran; UV is ultra violet; and t-BuOK is potassium t-butoxide.

Reaction Schemes below illustrate the methods employed in the synthesis of the compounds of the present invention of Formula I. All substituents are as defined above unless indicated otherwise. The synthesis of the novel compounds of the present invention may be accomplished by one or more of the synthetic schemes described herein.

SCHEME 1

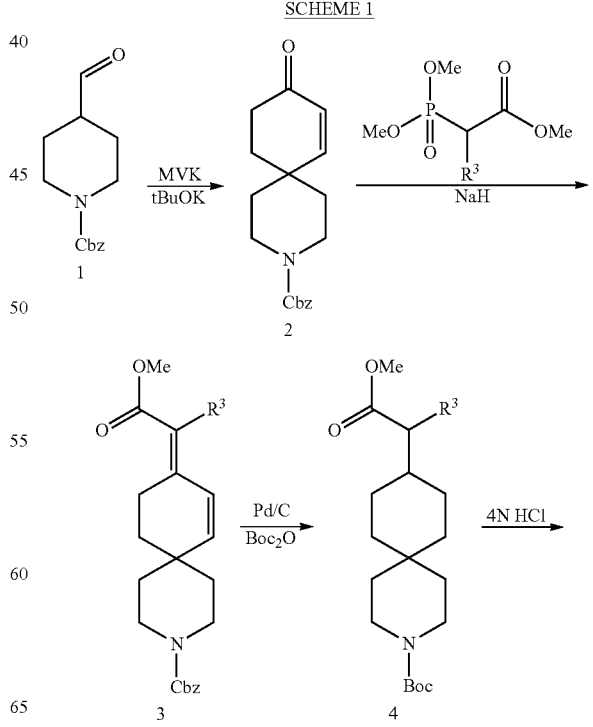

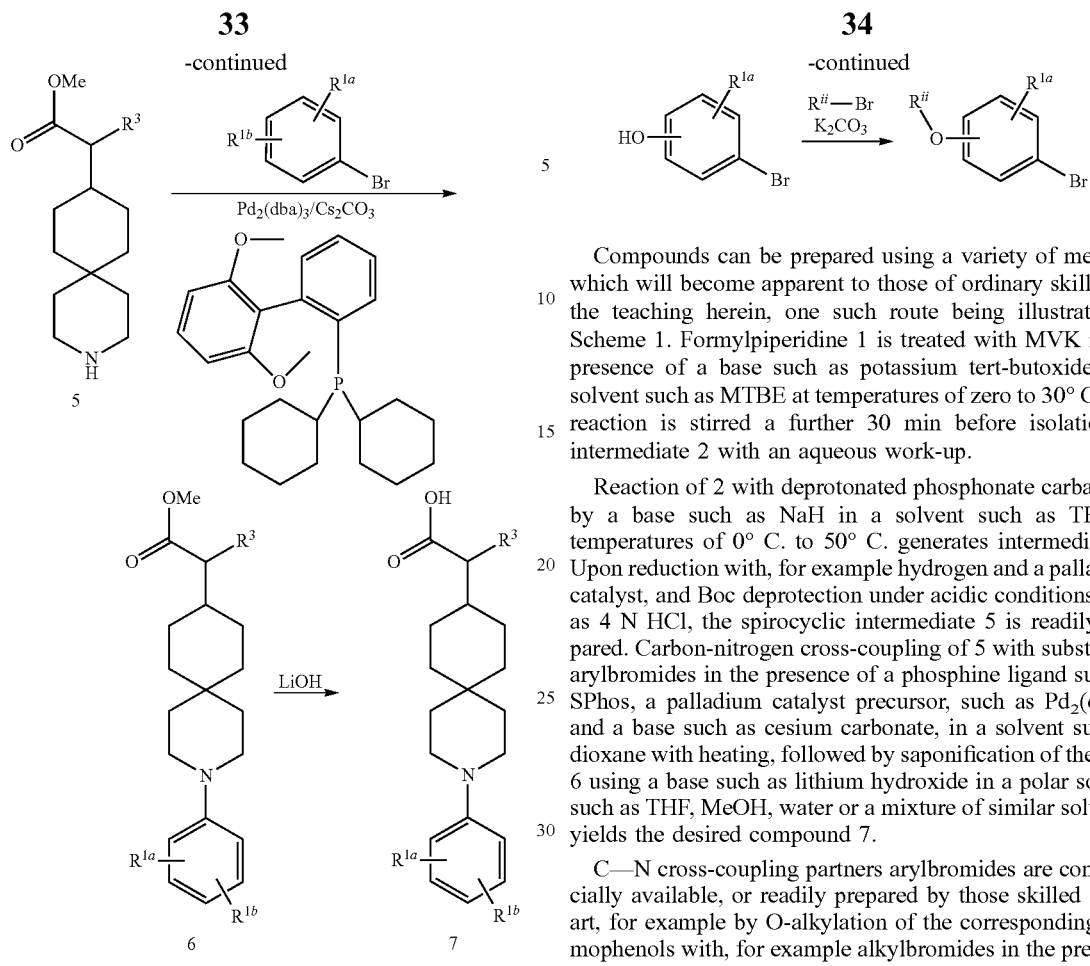

Compounds can be prepared using a variety of methods which will become apparent to those of ordinary skill from the teaching herein, one such route being illustrated in Scheme 1. Formylpiperidine 1 is treated with MVK in the presence of a base such as potassium tert-butoxide in a solvent such as MTBE at temperatures of zero to 30° C. The reaction is stirred a further 30 min before isolation of intermediate 2 with an aqueous work-up.

Reaction of 2 with deprotonated phosphonate carbanions by a base such as NaH in a solvent such as THF at temperatures of 0° C. to 50° C. generates intermediate 3. Upon reduction with, for example hydrogen and a palladium catalyst, and Boc deprotection under acidic conditions such as 4 N HCl, the spirocyclic intermediate 5 is readily prepared. Carbon-nitrogen cross-coupling of 5 with substituted arylbromides in the presence of a phosphine ligand such as SPhos, a palladium catalyst precursor, such as $Pd_2(dba)_3$, and a base such as cesium carbonate, in a solvent such as dioxane with heating, followed by saponification of the ester 6 using a base such as lithium hydroxide in a polar solvent such as THF, MeOH, water or a mixture of similar solvents, yields the desired compound 7.

C—N cross-coupling partners arylbromides are commercially available, or readily prepared by those skilled in the art, for example by O-alkylation of the corresponding bromophenols with, for example alkylbromides in the presence of a base such as potassium carbonate.

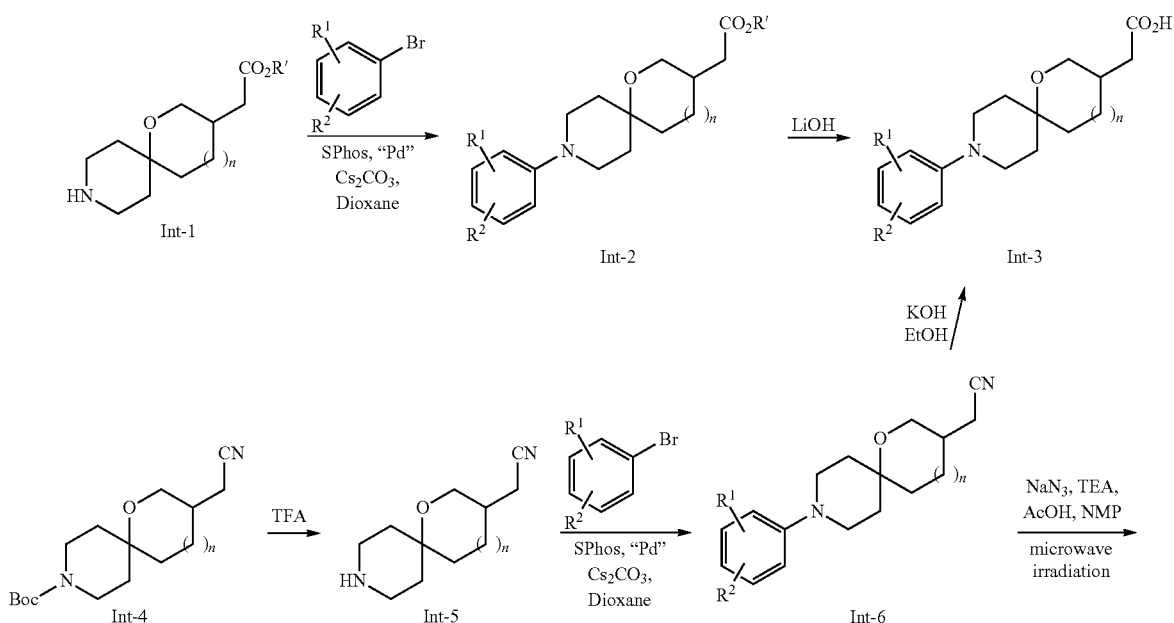

-continued

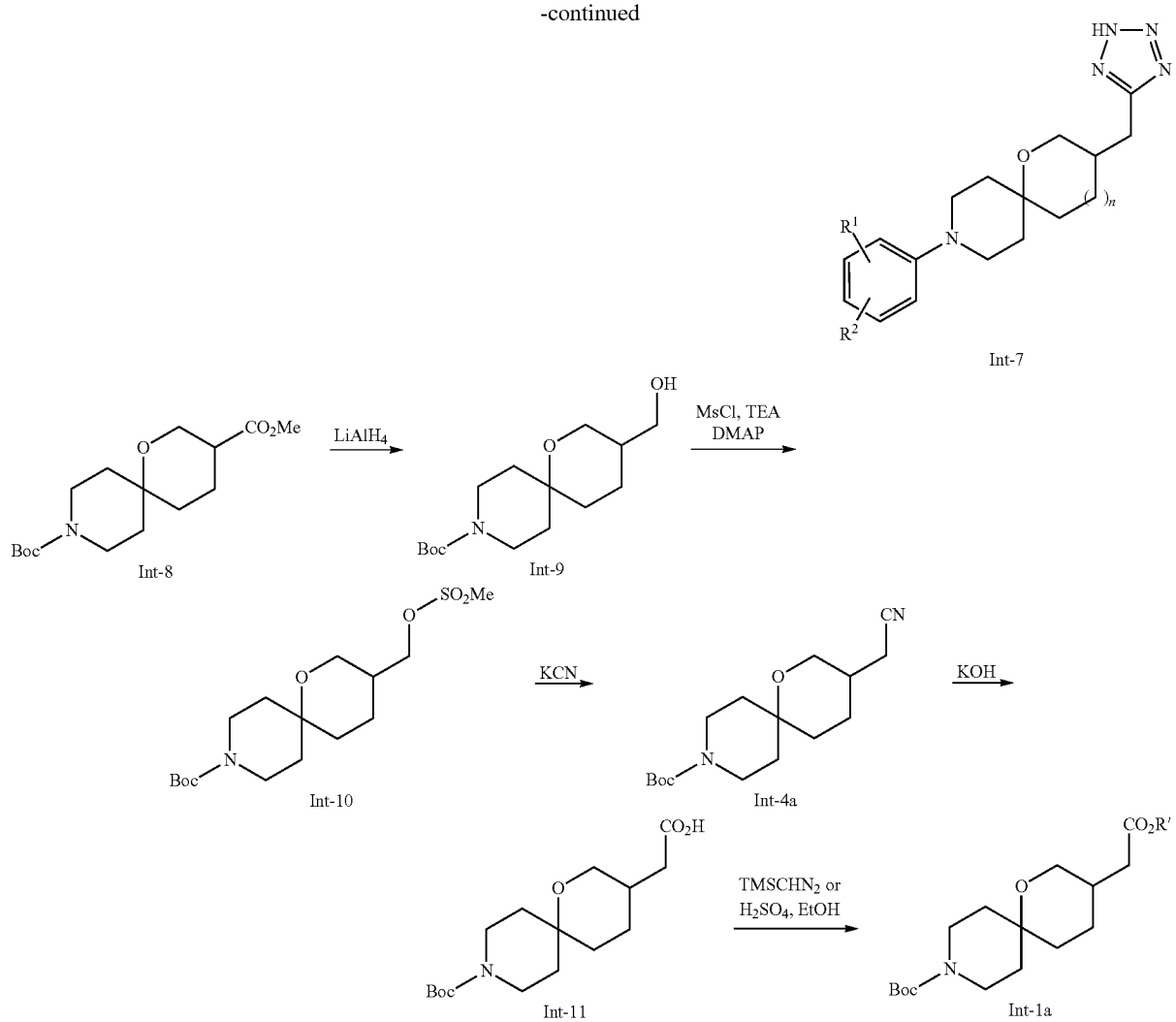

As illustrated in Scheme 2, an oxaspiropipedine Int 1 is reacted with an aryl halide such as an aryl bromide in the presence of a palladium catalyst, a ligand such as Sphos, and a base such as cesium carbonate, in a solvent such as dioxane at elevated temperature to afford the N-arylated oxaspiropiperidine Int-2. Upon saponification, the ester Int-2 is converted to the carboxylic acid product Int-3.

Alternatively compounds Int-3 can be synthesized by reacting cyanomethyl substituted oxaspiropiperidines Int-5, after removal of Boc protection group of compounds Int-4, with an aryl halide such as an aryl bromide in similar C—N cross coupling conditions to provide compounds Int-6, which are then hydrolyzed to form the carboxylic acids. For some instances the intermediates Int-6 can be further modified if desired, for example, by reaction with sodium azide at elevated temperature, such as microwave irridiation, to provide the tetrazole final compounds Int-7.

The depicted oxaspiropiperidines Int-1 can be obtained commercially, are known in the literature (Tetrahedron Lett., 2011, 52, 6457) and may be prepared by a variety of methods by those skilled in the art. One such example for forming Int-1a is shown in Scheme 2, involving reduction of the methylester Int-8 to methylene alcohol Int-9. Mesylation of the alcohol by treatment with MsCl and bases such as triethylamine and DMAP to yield Int-10, followed by cyano replacement with potassium cyanide, can provide Int-4a. Hydrolysis with a base such as potassium hydroxide can readily convert Int-4a to the corresponding carboxylic acid Int-11, which can then be conveniently transformed to the ester Int-1a when being subjected to (trimethylsilyl)diazomethane or sulfuric acid in the presence of an alcohol such as ethanol.

As will be known to those skilled in the art, in all schemes, the products of Formula I and all synthetic intermediates may be purified from unwanted side products, reagents and solvents by recrystallization, trituration, preparative thin layer chomatography, flash chomatography on silica gel as described by W. C. Still et al, J. Org. Chem. 1978, 43, 2923, or reverse-phase HPLC. Compounds purified by HPLC may be isolated as the corresponding salt.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chromatography using a homochiral stationary phase and, in the case of cis/trans isomers and diastereomers, normal-phase and reverse-phase chomatography.

Chemical reactions were monitored by LCMS, and the purity and identity of the reaction products were assayed by LCMS (electrospray ionization) and NMR. ¹H NMR spectra are internally referenced to residual protio solvent signals. Data for 1H NMR are reported with chemical shift (δ ppm), multiplicity (s=singlet, d=doublet, t=triplet, q=quartet, m=multiplet, br s=broad singlet, br m=broad multiplet), coupling constant (Hz), and integration. Unless otherwise noted, all LCMS ions listed are [M+H]. All temperatures are degrees Celsius unless otherwise noted.

In the Examples, some intermediates and final compounds having a chiral carbon were prepared as racemates. The term "rac" refers to a racemic mixture.

Preparative HPLC was performed on either a YMC-Pack Pro C18 column (100×20 mm i.d.) or a Waters XBridge C18 column (100×19 mm i.d.), or a Waters Sunfire C18 column (100×19 mm i.d.).

Flash chomatography on silica gel was performed using pre-packed silica gel columns on Biotage Horizon or Biotage SP-1 instruments equipped with UV detectors.

The following examples are provided so that the invention might be more fully understood. They should not be construed as forming the only genus that is considered as the invention nor limiting the invention in any way.

EXAMPLE 1

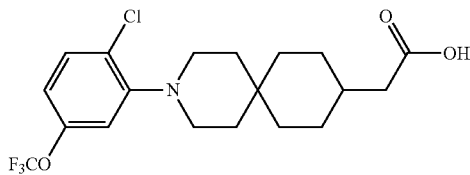 [SMILES: O=C(O)CC1CCC2(CC1)CCN(c1cc(OC(F)(F)F)ccc1Cl)CC2]

Preparation of 2-(3-(2-chloro-5-(trifluoromethoxy)phenyl)-3-azaspiro[5.5]undecan-9-yl)acetic acid Step A. Benzyl 9-oxo-3-azaspiro[5.5]undec-7-ene-3-carboxylate: To a solution of benzyl 4-formylpiperidine-1-carboxylate (660 g, 2.67 mol) dissolved in MTBE (11.4 L) was added the solution of but-3-en-2-one (187.4 g, 2.67 mol) dissolved in MTBE (900 mL) drop-wise for 0.5 h at 10~12° C., then stirred for 5 min. To the reaction mixture was added t-BuOK (39.7 g, 0.35 mol) dissolved in i-PrOH (2.3 L) drop-wise for 1 h below 30° C. and stirred for further 0.5 h. The reaction was quenched with AcOH (21.3 g). The organic layer was washed with $H_2O$ (4 L×2), then brine (4 L×2), dried over anhydrous $Na_2SO_4$, filtered and concentrated in vacuo to dryness. The residue was purified via silica column (Pentane:EtOAc=8:1 to 5:1) to obtain the title compound. LCMS m/z 322.3 [M+Na]+ ¹H NMR (500 MHz, CDCl₃) δ 7.38-7.27 (m, 5 H), 6.78 (d, J=12 Hz, 1 H), 5.95 (d, J=12 Hz, 1 H), 5.13 (s, 2H), 3.67-3.57 (m, 2 H), 3.52-3.44 (m, 2 H), 2.44 (d, J=8.0 Hz, 2 H), 1.95 (d, J=8.0 Hz, 2 H), 1.70-1.51 (m, 4 H).

Step B. Benzyl 9-(2-methoxy-2-oxoethylidene)-3-azaspiro[5.5]undec-7-ene-3-carboxylate: Under nitrogen protection, to a suspension of NaH (156 g, 3.89 mol) in THF (15 L) was added methyl 2-(dimethoxyphosphoryl)acetate (730 g, 4.0 mol) dissolved in THF (5 L) drop-wise at 0~5° C. over 1 h. After addition, the ice-bath was removed, and the mixture was stirred at 25~30° C. for 0.5 h. The suspension was heated to 40~45° C. The title compound from Example 1 Step A (580 g, 1.94 mol) dissolved in THF (3.5 L) was added drop-wise at this temperature for 0.5-1 h. The mixture was stirred at 45~50° C. for 20 h. The resulting mixture was cooled to 10~15° C., then diluted with EtOAc (10 L), quenched with 1 N HCl until pH 3-4, and stirred for 15 min. The mixture was washed with $NaHCO_3$ aq. (5 L×2), then with brine (5 L×2), dried over $Na_2SO_4$, filtered and concentrated in vacuo to dryness. The residue was purified by silica gel chromatography (pentane:EtOAc=0 to 12:1) to obtain the title compound.

Step C. tert-Butyl 9-(2-methoxy-2-oxoethyl)-3-azaspiro[5.5]undecane-3-carboxylate: A mixture of the title compound from Example 1 Step B (140 g, 0.40 mol) dissolved in MeOH (1400 mL), 10% Pd/C (14 g, $H_2O≤1\%$) and $Boc_2O$ (127.5 g, 0.59 mol) were stirred under 50 psi hydrogen at 35~40° C. for 24 h. Then the mixture was filtered through CELITE™ diatomaceous earth, washed with MeOH, and concentrated in vacuo to dryness. The residue was dissolved in DCM (100 mL), then the solution was cooled to 0~5° C., quenched with DMEDA (51 g, 0.57 mol) dropwise, stirred for 15-30 min at 20° C. The solution was washed with 1 N HCl (100 mL×2), then brine (100 mL×2), dried over $Na_2SO_4$, filtered and concentrated in vacuum to give the title compound. LCMS m/z 326 [M+H]+ ¹H NMR (500 MHz, CDCl₃) δ 3.67 (s, 3H), 3.39-3.31 (m, 4 H), 2.22 (d, J=7.0 Hz, 2 H), 1.81-1.72 (m, 1 H), 1.68-1.63 (m, 2 H), 1.60-1.54 (m, 2 H), 1.48-1.43 (m, 2 H), 1.45 (s, 9 H), 1.32-1.26 (m, 2 H), 1.19-1.10 (m, 4 H).

Step D. Methyl 2-(3-azaspiro[5.5]undecan-9-yl)acetate: To a round bottom flask was added the title compound from Example 1 Step C (20 g, 61.4 mmol) in MeOH (120 ml), and then 4 M HCl in dioxane (48 mL) was added. The mixture was stirred at ambient temperature for 3 h. The solvent was removed under reduced pressure to afford an off-white solid as crude product. To the crude product was added saturated $NaHCO_3$ until basic. The water layer was extracted with DCM (2×300 mL), the organic layer was combined and washed with brine and dried over $Na_2SO_4$, filtered and dried down to afford the title compound that was used directly for next step.

Step E. Methyl 2-(3-(2-chloro-5-(trifluoromethoxy)phenyl)-3-azaspiro[5.5]undecan-9-yl)acetate: To a pressure tube was added 2-bromo-1-chloro-4-(trifluoromethoxy)benzene (230 mg, 0.84 mmol), the title compound from Example 1 Step D (100 mg, 0.42 mmol), $Pd_2(dba)_3$ (38 mg, 0.042 mmol), 2-dicyclohexylphosphino-2',6'-dimethoxybiphenyl (51 mg, 0.125 mmol), and Cesium carbonate (408 mg, 1.25 mmol) in Dioxane (3 ml). Degassed by $N_2$ for 5 min, then heated at 100° C. for 1.5 day. The mixture was cooled to ambient temperature. The reaction mixture was filtered through a CELITE™ diatomaceous earth pad and washed with DCM. The filtrate was concentrated, and the afforded residue was purified by column chromatography on silica gel, eluting with EtOAc/Hexane to give the title compound. LCMS m/z 420.2 [M+H]+ ¹H NMR (500 MHz, CDCl₃) δ 7.33 (d, J=8.5 Hz, 1 H), 6.87 (s, 1 H), 6.80 (d, J=8.5 Hz, 1 H), 3.67 (s, 3H), 2.97 (m, 4 H), 2.24 (d, J=7.0 Hz, 2 H), 1.84-1.73 (m, 3 H), 1.72-1.67 (m, 2 H), 1.62-1.52 (m, 4 H), 1.24-1.14 (m, 4 H).

Step F. 2-(3-(2-Chloro-5-(trifluoromethoxy)phenyl)-3-azaspiro[5.5]undecan-9-yl)acetic acid: To the title compound from Example 1 Step E (108 mg, 0.25 mmol) was added THF/MeOH (3 mL/2 ml), then 2 M aqueous solution of LiOH (1.25 mL). The reaction was stirred at room temperature overnight. The solvent was removed and, and the residue was purified by reverse phase HPLC (60%-100% acetonitrile/$H_2O$, 0.05% TFA in each) to afford the title compound. LCMS m/z 406.1 [M+H]+ $^1$H NMR (500 MHz, CDCl$_3$) δ 7.36 (d, J=8.5 Hz, 1 H), 6.98 (s, 1 H), 6.87 (d, J=8.5 Hz, 1 H), 3.12-3.03 (m, 4 H), 2.30 (d, J=7.0 Hz, 2 H), 1.86-1.72 (m, 5 H), 1.68-1.57 (m, 4 H), 1.27-1.16 (m, 4 H). Human GPR120 EC$_{50}$: 790 nM

EXAMPLE 2

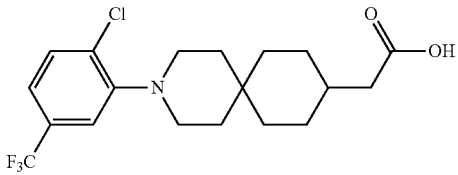 [SMILES: O=C(O)CC1CCC2(CC1)CCN(c1cc(C(F)(F)F)ccc1Cl)CC2]

Preparation of 2-(3-(2-chloro-5-(trifluoromethyl)phenyl)-3-azaspiro[5.5]undecan-9-y)acetic acid Step A. 2-(3-(2-Chloro-5-(trifluoromethyl)phenyl)-3-azaspiro[5.5]undecan-9-yl)acetic acid: To a 2 dram vial were added the title compound from Example 1 Step D (30 mg, 0.125 mmol), SPhos precatalyst (2.58 mg, 3.76 μmol), cesium carbonate (123 mg, 0.376 mmol) and 2-bromo-1-chloro-4-(trifluoromethyl)benzene (10.01 mg, 0.125 mmol). The reaction mixture was then transferred to a glove box and 1,4-dioxane (1 mL) was added. The mixtures were stirred at 100° C. After 18 h, The mixture was allowed to cool to ambient temperature. Tetrahydrofuran (1 mL) and sodium hydroxide (0.5 mL, 0.125 mmol) were added and the resultant mixture was stirred at 50° C. After 4 h, the reaction mixture was allowed to cool to ambient temperature, Aqueous HCl (1 mL, 1 N aqueous, 1 mmol) was added and the solvents removed in the Genevac under reduced pressure. Purification by reversed phase HPLC (30% to 100% acetonitrile in water, each with 0.1% v/v TFA) provided the title compound. LCMS m/z 390.15 [M+H]+ $^1$H NMR (500 MHz, CDCl$_3$) δ 7.48 (d, J=8.0 Hz, 1 H), 7.36 (s, 1 H), 7.25 (d, J=8.0 Hz, 1 H), 3.11 (quintet, J=6.0 Hz, 4 H), 2.31 (d, J=7.0 Hz, 2 H), 1.86-1.73 (m, 5 H), 1.69-1.57 (m, 4 H), 1.28-1.18 (m, 4 H). Human GPR120 EC$_{50}$: 900 nM

EXAMPLES 3 & 4

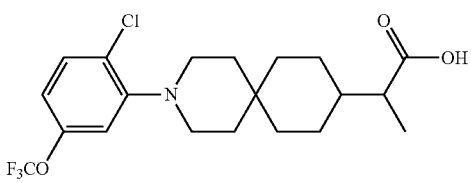

3

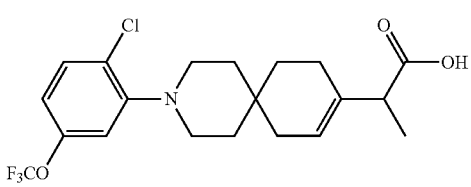

4

Preparation of (rac) 2-(3-(2-chloro-5-(trifluoromethoxy)phenyl)-3-azaspiro[5.5]undecan-9-yl) propanoic acid 3 and (rac) 2-(3-(2-chloro-5-(trifluoromethoxy)phenyl)-3-azaspiro[5.5]undec-8-en-8-yl) propanoic acid 4

Step A. Benzyl-(1-ethoxy-1-oxopropan-2-ylidene)-3-azaspiro[5.5]undec-7-ene-3-carboxylate: A suspension of NaH (120 mg, 3.01 mmol) in THF (10 mL) was cooled to 0° C., added dropwise triethyl 2-phosphonopropionate (716 mg, 3.01 mmol), warmed up to rt and stirred for 30 min. Added dropwise a solution of the title compound from Example 1 Step A (600 mg, 2.004 mmol) in 10 ml of THF, stirred at 60° C. After 2 days, the mixture was concentrated to remove the solvent, the resultant neutralized with 1 N HCl, extracted with EtOAc. The organic solution was separated, dried over Na$_2$SO$_4$, and concentrated to give the crude as oil. Purification by normal phase chromatography on silica gel (0 to 100% EtOAc in hexanes) gave the title compound.

Step B. (rac) Ethyl 2-(3-azaspiro[5.5]undecan-9-yl)propanoate and (rac) ethyl 2-(3-azaspiro[5.5]undec-8-en-9-yl)propanoate: Into a flask was added a solution of the title compound from Example 3 Step A (400 mg, 1.043 mmol) in Ethanol (10 ml) and Pd/C (38.9 mg, 0.365 mmol). The mixture was heated at 80° C. under H$_2$ atmosphere. After overnight, LCMS showed desired product (m/z 254) and partial hydrogenation product (m/z 252) as a mixture. The reaction was stopped, and the mixture was filtered through a CELITE™ diatomaceous earth pad. The filtrate was concentrated to give a crude residue.

Step C. (rac) Ethyl 2-(3-(2-chloro-5-(trifluoromethoxy)phenyl)-3-azaspiro[5.5]undec-7-en-9-yl)propanoate and (rac) ethyl 2-(3-(2-chloro-5-(trifluoromethoxy)phenyl)-3-azaspiro[5.5]undec-7-en-9-yl)propanoate: Into a two-dram vial was added 2-bromo-1-chloro-4-(trifluoromethoxy)benzene (100 mg, 0.363 mmol), the title compounds from Example 3 Step B (100 mg), and SPhos biaryl precatalysis (26.2 mg, 0.036 mmol), cesium carbonate (237 mg, 0.726 mmol) followed by 1,4-dioxane (2 ml). The mixture was degassed by N$_2$ for 5 min, then heated at 100° C. for 24 h. Concentrate to remove solvents. The afforded crude was purified with normal phase silica gel chromatography (0 to 100% EtOAc in 1:1 mixed hexanes/DCM) to give desired product (as a mixture of 2).

Step D. (rac) 2-(3-(2-Chloro-5-(trifluoromethoxy)phenyl)-3-azaspiro[5.5]undecan-9-yl)propanoic acid and 2-(3-(2-chloro-5-(trifluoromethoxy)phenyl)-3-azaspiro[5.5]undec-8-en-9-yl)propanoic acid: LiOH (8.69 mg, 0.363 mmol) was added to the product from Example 3 Step C followed by addition of MeOH, THF and water (0.3 mL each). Stir at 50° C. for overnight. Concentrate to remove solvents. The residue was purified by reverse phase HPLC (10 to 100% acetonitrile in water, each with 0.1% v/v TFA) to give two products with Example 4 as partially hydrogenated product (1st peak), and Example 3 as the hydrogenated product (2nd peak).

EXAMPLE 3

LCMS m/z 418.1 [M+H]+ $^1$H NMR (500 MHz, CDCl$_3$) δ 9.4 (broad s, 1 H), 7.41 (d, J=9.0 Hz, 1 H), 7.10 (s, 1 H), 6.95 (d, J=8.5 Hz, 1 H), 5.59 (s, 1 H), 3.31-3.10 (m, 5 H), 2.18-1.99 (m, 4 H), 1.77-1.67 (m, 4 H), 1.65-1.58 (m, 2 H), 1.29 (d, J=7.0 Hz, 3 H). Human GPR120 EC$_{50}$: 3400 nM

EXAMPLE 4

LCMS m/z 420.1 [M+H]+ $^1$H NMR (500 MHz, CDCl$_3$) δ 10.29 (broad s, 1 H), 7.42 (d, J=9.0 Hz, 1 H), 7.14 (s, 1 H), 6.97 (d, J=8.5 Hz, 1 H), 3.31-3.20 (m, 4 H), 2.35 (quintet, J=6.5 Hz, 1 H), 1.88-1.77 (m, 4 H), 1.70-1.54 (m, 5 H), 1.35-1.14 (m, 7 H). Human GPR120: 37% activation at 8300 nM

EXAMPLE 5

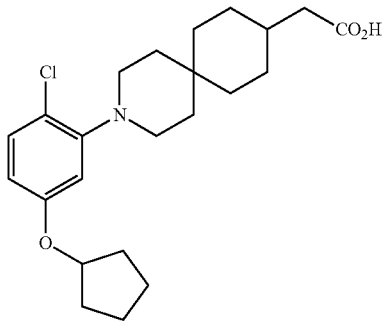 [SMILES: O=C(O)CC1CCC2(CC1)CCN(c1cc(OC3CCCC3)ccc1Cl)CC2]

Preparation of 2-(3-(2-chloro-5-(cyclopentyloxy)phenyl)-3-azaspiro[5.5]undecan-9-yl)acetic acid

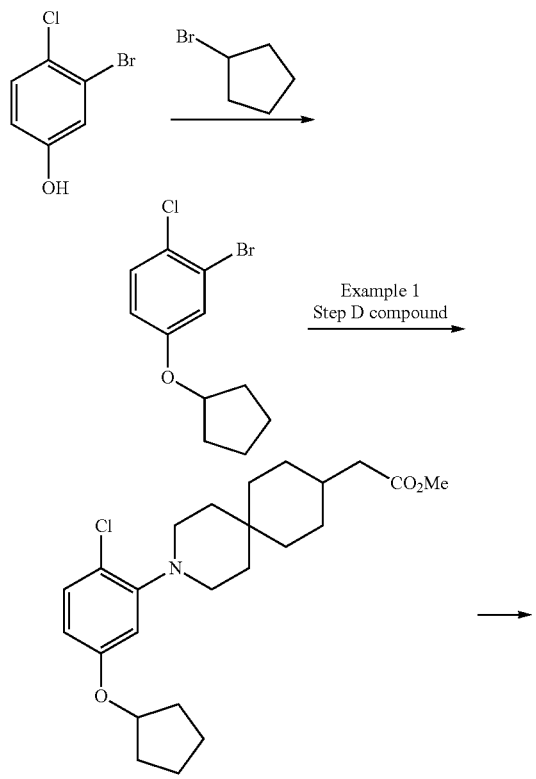

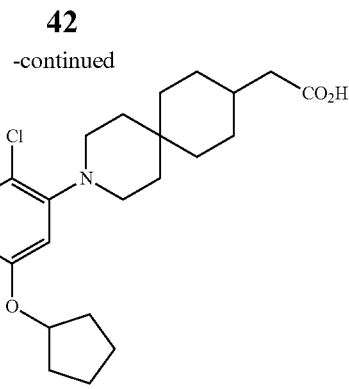

Step A. 2-Bromo-1-chloro-4-(cyclopentyloxy)benzene: To a vial was added 3-bromo-4-chlorophenol (380 mg, 1.832 mmol), bromocyclopentane (0.216 ml, 2.015 mmol), potassium carbonate (506 mg, 3.66 mmol) in DMF (10 ml). Then the mixture was heated at 80° C. for 4 h. The mixture was allowed to cool to ambient temperature, the solvent removed, and the resulted residue was purified by flash chromatography on silica gel (EtOAc/hexanes) to give the title compound.

Step B. Ethyl 2-(3-(2-chloro-5-(cyclopentyloxy)phenyl)-3-azaspiro[5.5]undecan-9-yl)acetate: To a vial was added $Pd_2(dba)_3$ (40.6 mg, 0.044 mmol), 2-bromo-1-chloro-4-(cyclopentyloxy)benzene (the title compound from Example 5 Step A) (135 mg, 0.488 mmol), the title compound from Example 1 Step D (100 mg, 0.444 mmol), 2-dicyclohexylphosphino-2',6'-dimethoxybiphenyl (54.7 mg, 0.133 mmol) and cesium carbonate (434 mg, 1.331 mmol) in dioxane (3 mL). The mixture was degassed by $N_2$ for 2 min, then heated at 100° C. for 24 h. The reaction mixture was allowed to cool to ambient temperature, then filtered through a CELITE™ diatomaceous earth pad to remove any solid, and washed with EtOAc. The combined filtrate solution was concentrated to give the title compound.

Step C. 2-(3-(2-chloro-5-(cyclopentyloxy)phenyl)-3-azaspiro[5.5]undecan-9-yl)acetic acid: To the title compound from Example 5 Step B was added THF/MeOH/$H_2O$ (2 mL/1 mL/0.5 mL) followed by addition of LiOH (53.1 mg, 2.219 mmol). The reaction was heated at 50° C. for 4 h. The solvent was removed and the residue was purified by reverse phase HPLC (acetonitrile/$H_2O$, 0.05% TFA) to give the title compound. LCMS m/z 406.2 [M+H]+ $^1$H NMR (500 MHz, $CD_3OD$) δ 7.31 (d, J=8.5 Hz, 1 H), 6.86 (d, J=3 Hz, 1 H), 6.71 (dd, J=3 Hz, 3Hz, 1 H), 4.83-4.80 (m, 1 H), 3.20 (t, J=8.0 Hz, 4 H), 2.23 (d, J=7.5 Hz, 2 H), 1.98-1.24 (m, 21 H). Human GPR120 $EC_{50}$: 1100 nM The examples in Table 1 were prepared using chemistry previously described.

TABLE 1

| Ex. # | Structure | LCMS [M + H]+ | GPR120 Human $EC_{50}$ (nM) |
|---|---|---|---|
| 6 | 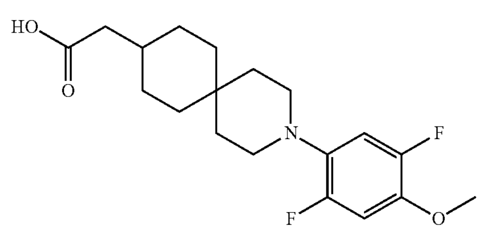 [SMILES: COc1cc(F)c(N2CCC3(CCC(CC(=O)O)CC3)CC2)cc1F] | 354.1 | 2420 |

TABLE 1-continued

| Ex. # | Structure | LCMS [M + H]+ | GPR120 Human EC$_{50}$ (nM) |
|---|---|---|---|
| 7 | 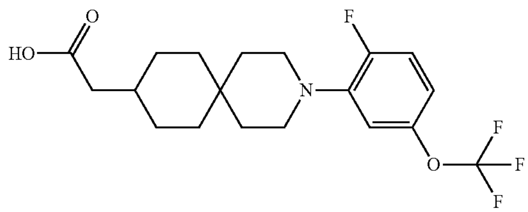 [SMILES: O=C(O)CC1CCC2(CC1)CCN(c1cc(OC(F)(F)F)ccc1F)CC2] | 390.1 | 410 |
| 8 | 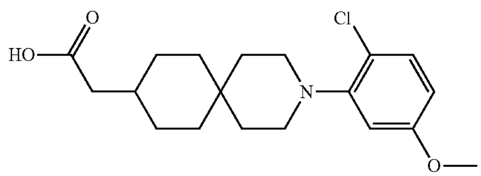 [SMILES: COc1ccc(Cl)c(N2CCC3(CCC(CC(=O)O)CC3)CC2)c1] | 352.1 | 1670 |
| 9 | 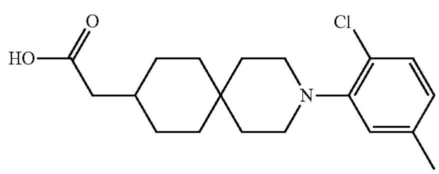 [SMILES: Cc1ccc(Cl)c(N2CCC3(CCC(CC(=O)O)CC3)CC2)c1] | 336.2 | 2175 |
| 10 | 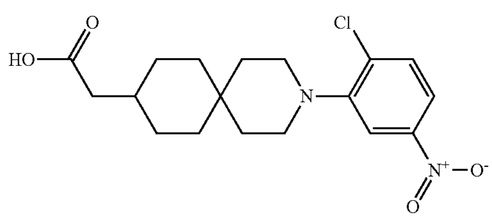 [SMILES: O=C(O)CC1CCC2(CC1)CCN(c1cc([N+](=O)[O-])ccc1Cl)CC2] | 367.1 | 1700 |
| 11 | 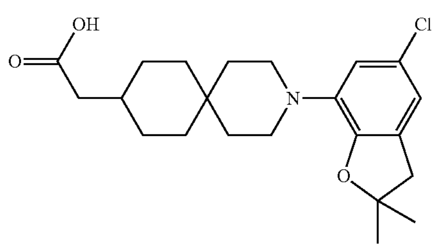 [SMILES: CC1(C)Cc2cc(Cl)cc(N3CCC4(CCC(CC(=O)O)CC4)CC3)c2O1] | 392.2 | 2850 |
| 12 | 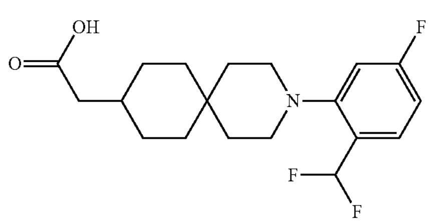 [SMILES: O=C(O)CC1CCC2(CC1)CCN(c1cc(F)ccc1C(F)F)CC2] | 356.2 | 2422 |
| 13 | 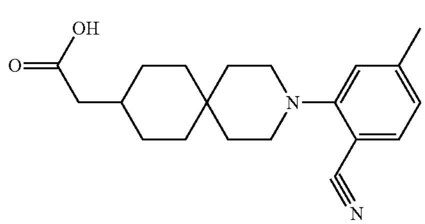 [SMILES: Cc1ccc(C#N)c(N2CCC3(CCC(CC(=O)O)CC3)CC2)c1] | 327.2 | 2142 |

TABLE 1-continued

| Ex. # | Structure | LCMS [M + H]+ | GPR120 Human EC$_{50}$ (nM) |
|---|---|---|---|
| 14 | 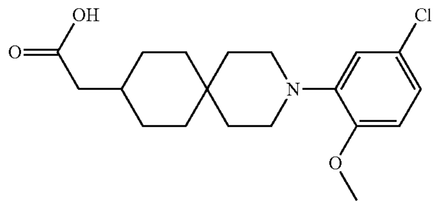 [SMILES: COc1ccc(Cl)cc1N1CCC2(CCC(CC(=O)O)CC2)CC1] | 352.2 | 3101 |
| 15 | 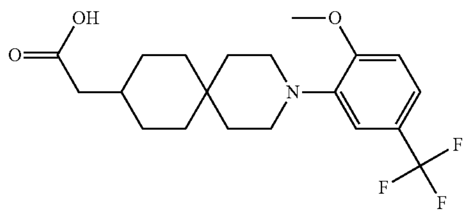 [SMILES: COc1ccc(C(F)(F)F)cc1N1CCC2(CCC(CC(=O)O)CC2)CC1] | 386.2 | 2355 |
| 16 | 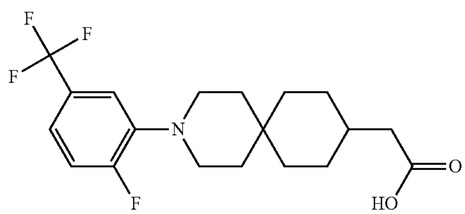 [SMILES: O=C(O)CC1CCC2(CC1)CCN(c1cc(C(F)(F)F)ccc1F)CC2] | 374.2 | 652 |
| 17 | 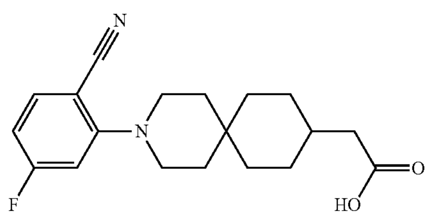 [SMILES: N#Cc1ccc(F)cc1N1CCC2(CCC(CC(=O)O)CC2)CC1] | 331.2 | 2364 |
| 18 | 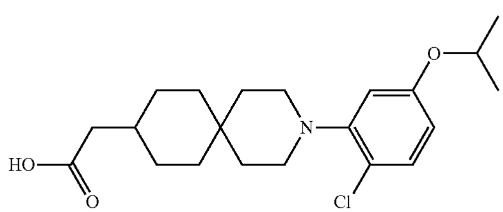 [SMILES: CC(C)Oc1ccc(Cl)c(N2CCC3(CCC(CC(=O)O)CC3)CC2)c1] | 380.2 | 530 |
| 19 | 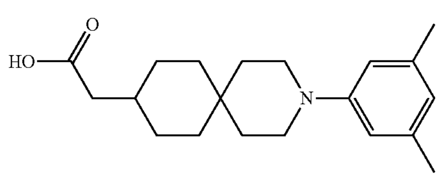 [SMILES: Cc1cc(C)cc(N2CCC3(CCC(CC(=O)O)CC3)CC2)c1] | 316.2 | 948 |
| 20 | 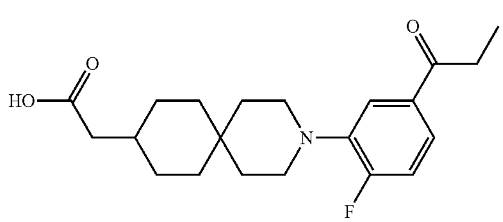 [SMILES: CCC(=O)c1ccc(F)c(N2CCC3(CCC(CC(=O)O)CC3)CC2)c1] | 362.2 | 1658 |

TABLE 1-continued

| Ex. # | Structure | LCMS [M + H]+ | GPR120 Human EC$_{50}$ (nM) |
|---|---|---|---|
| 21 | 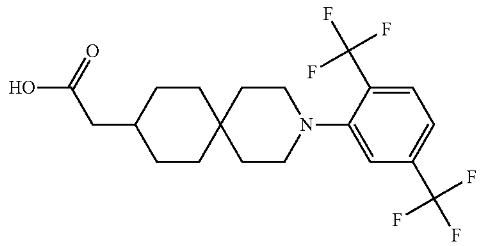 [SMILES: O=C(O)CC1CCC2(CC1)CCN(c1cc(C(F)(F)F)ccc1C(F)(F)F)CC2] | 424.2 | 3273 |
| 22 | 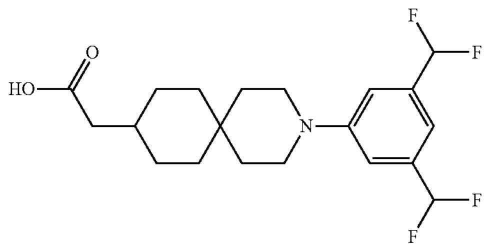 | 388.2 | 3006 |
| 23 | 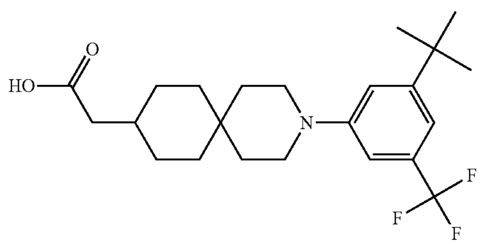 [SMILES: CC(C)(C)c1cc(N2CCC3(CCC(CC(=O)O)CC3)CC2)cc(C(F)(F)F)c1] | 412.2 | 3753 |
| 24 | 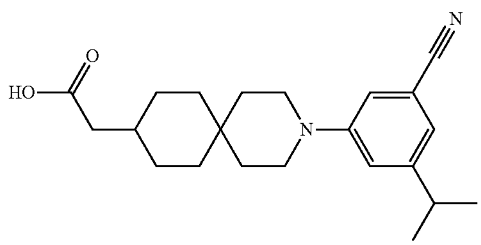 [SMILES: CC(C)c1cc(C#N)cc(N2CCC3(CCC(CC(=O)O)CC3)CC2)c1] | 355.2 | 3459 |
| 25 | 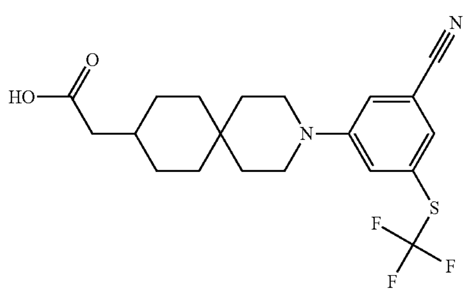 [SMILES: N#Cc1cc(SC(F)(F)F)cc(N2CCC3(CCC(CC(=O)O)CC3)CC2)c1] | 413.2 | 1154 |
| 26 | 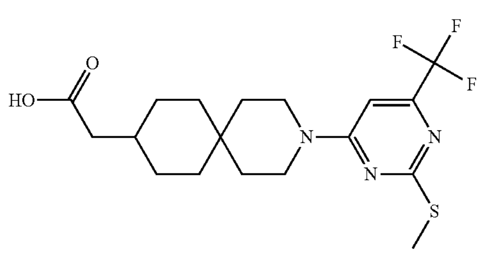 [SMILES: CSc1nc(N2CCC3(CCC(CC(=O)O)CC3)CC2)cc(C(F)(F)F)n1] | 404.2 | 8300 (62% activation) |

TABLE 1-continued
| Ex. # | Structure | LCMS [M + H]+ | GPR120 Human EC$_{50}$ (nM) |
|---|---|---|---|
| 27 | 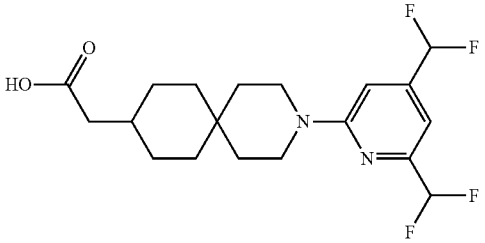 | 389.2 | 2993 |
| 28 | 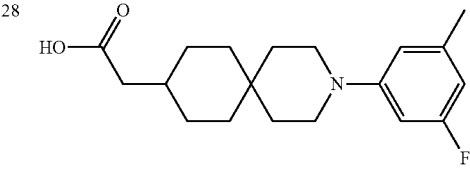 | 320.2 | 3040 |
| 29 | 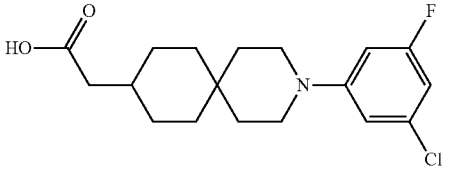 | 340.1 | 1786 |
| 30 | 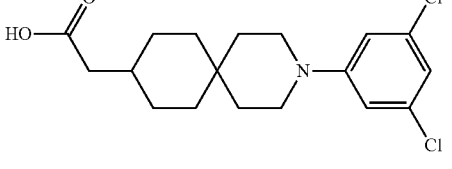 | 356.1 | 878 |
| 31 | 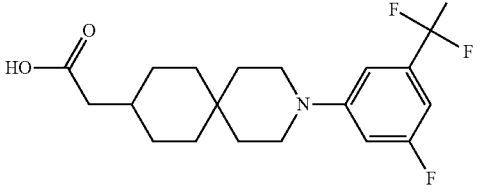 | 374.2 | 1216 |
| 32 | 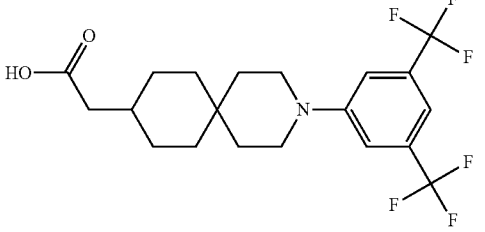 | 424.2 | 2152 |
| 33 | 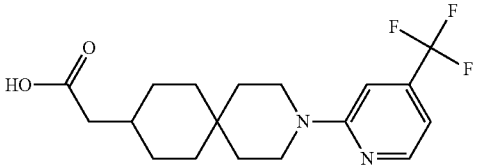 [SMILES: O=C(O)CC1CCC2(CC1)CCN(c1cc(C(F)(F)F)ccn1)CC2] | 357.2 | 3060 |

TABLE 1-continued
| Ex. # | Structure | LCMS [M + H]+ | GPR120 Human EC$_{50}$ (nM) |
|---|---|---|---|
| 34 | 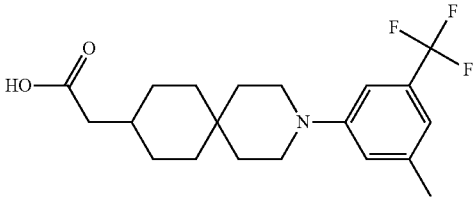 [SMILES: Cc1cc(N2CCC3(CCC(CC(=O)O)CC3)CC2)cc(C(F)(F)F)c1] | 370.2 | 671 |
| 35 | 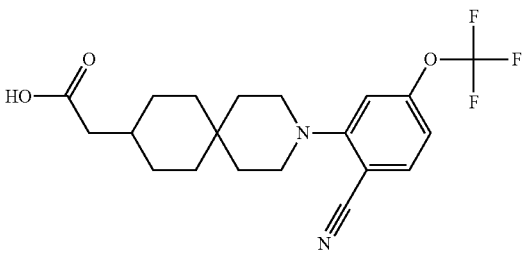 [SMILES: N#Cc1ccc(OC(F)(F)F)cc1N1CCC2(CCC(CC(=O)O)CC2)CC1] | 397.2 | 431 |
| 36 | 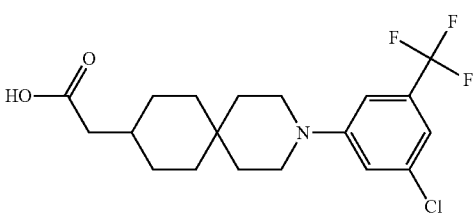 [SMILES: O=C(O)CC1CCC2(CC1)CCN(c1cc(Cl)cc(C(F)(F)F)c1)CC2] | 390.1 | 832 |
| 37 | 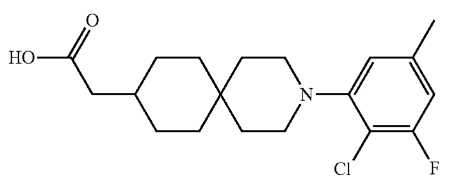 [SMILES: Cc1cc(F)c(Cl)c(N2CCC3(CCC(CC(=O)O)CC3)CC2)c1] | 354.2 | 2171 |
| 38 | 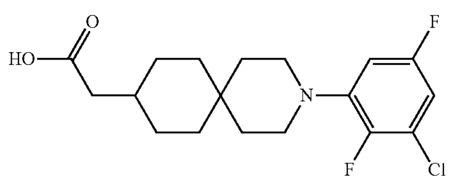 [SMILES: O=C(O)CC1CCC2(CC1)CCN(c1cc(F)cc(Cl)c1F)CC2] | 358.1 | 2148 |
| 39 | 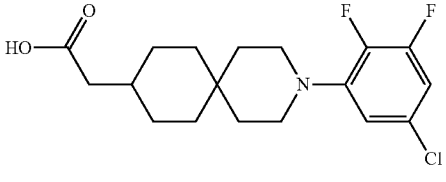 [SMILES: O=C(O)CC1CCC2(CC1)CCN(c1cc(Cl)cc(F)c1F)CC2] | 358.1 | 1799 |
| 40 | 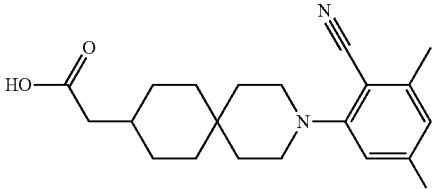 | 361.2 | 2535 |

TABLE 1-continued

| Ex. # | Structure | LCMS [M + H]+ | GPR120 Human EC$_{50}$ (nM) |
| --- | --- | --- | --- |
| 41 | 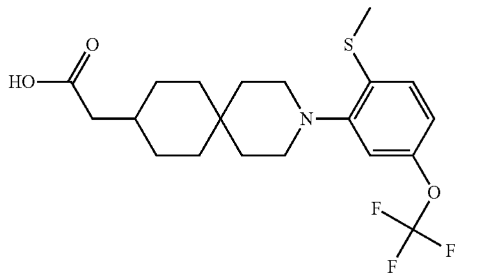 [SMILES: CSc1ccc(OC(F)(F)F)cc1N1CCC2(CCC(CC(=O)O)CC2)CC1] | 418.2 | 1690 |
| 42 | 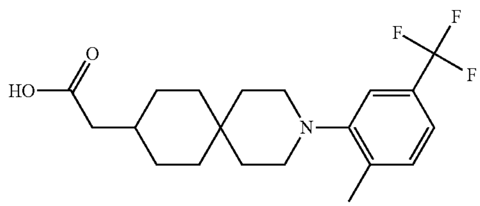 [SMILES: Cc1ccc(C(F)(F)F)cc1N1CCC2(CCC(CC(=O)O)CC2)CC1] | 370.2 | 749 |
| 43 | 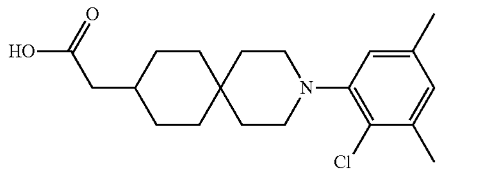 [SMILES: Cc1cc(C)c(Cl)c(N2CCC3(CCC(CC(=O)O)CC3)CC2)c1] | 350.2 | 2518 |
| 44 | 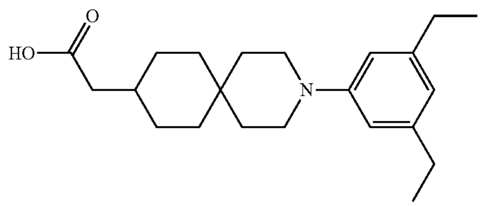 [SMILES: CCc1cc(CC)cc(N2CCC3(CCC(CC(=O)O)CC3)CC2)c1] | 344.3 | 2582 |
| 45 | 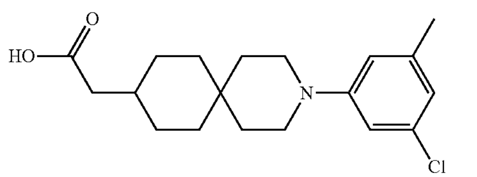 | 336.2 | 1171 |
| 46 | 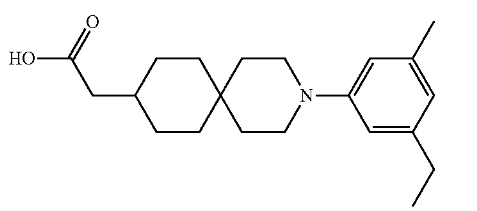 [SMILES: CCc1cc(C)cc(N2CCC3(CCC(CC(=O)O)CC3)CC2)c1] | 330.2 | 1288 |
| 47 | 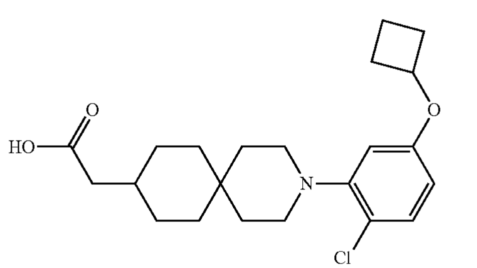 [SMILES: O=C(O)CC1CCC2(CC1)CCN(c1cc(OC3CCC3)ccc1Cl)CC2] | 392.2 | 330 |

TABLE 1-continued

| Ex. # | Structure | LCMS [M + H]+ | GPR120 Human EC$_{50}$ (nM) |
|---|---|---|---|
| 48 | 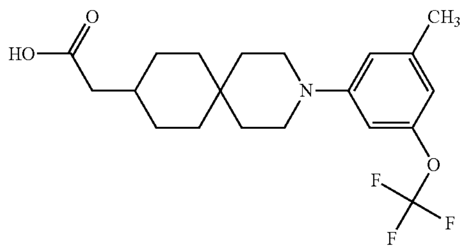 [SMILES: Cc1cc(OC(F)(F)F)cc(N2CCC3(CCC(CC(=O)O)CC3)CC2)c1] | 386.2 | 377 |
| 49 | 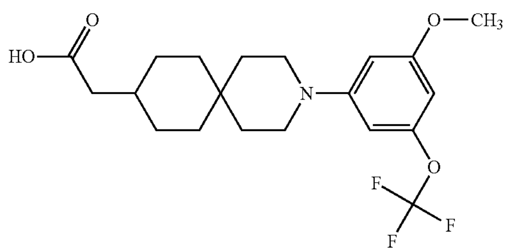 [SMILES: COc1cc(OC(F)(F)F)cc(N2CCC3(CCC(CC(=O)O)CC3)CC2)c1] | 402.2 | 449 |
| 50 | 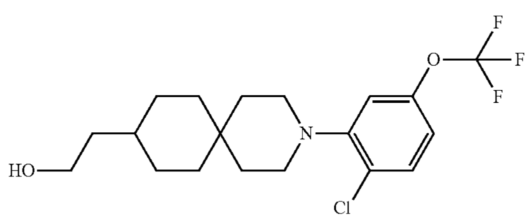 [SMILES: OCCC1CCC2(CC1)CCN(c1cc(OC(F)(F)F)ccc1Cl)CC2] | 393.1 | 472 |
| 51 | 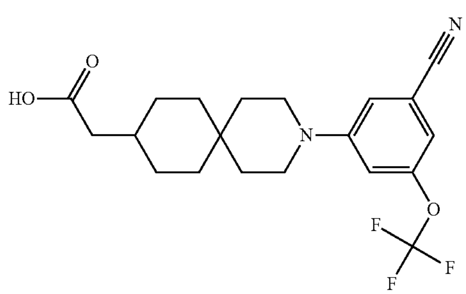 [SMILES: N#Cc1cc(OC(F)(F)F)cc(N2CCC3(CCC(CC(=O)O)CC3)CC2)c1] | 397.2 | 617 |
| 52 | 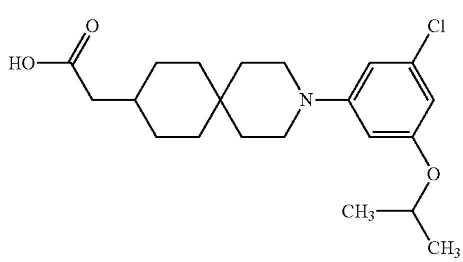 [SMILES: CC(C)Oc1cc(Cl)cc(N2CCC3(CCC(CC(=O)O)CC3)CC2)c1] | 380.2 | 641 |
| 53 | 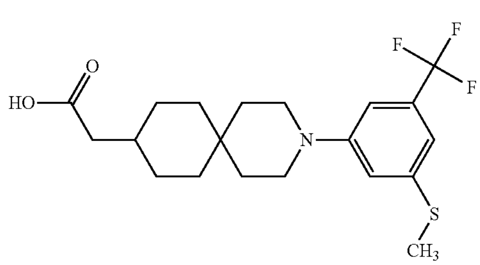 [SMILES: CSc1cc(N2CCC3(CCC(CC(=O)O)CC3)CC2)cc(C(F)(F)F)c1] | 402.2 | 667 |

TABLE 1-continued
| Ex. # | Structure | LCMS [M + H]+ | GPR120 Human EC$_{50}$ (nM) |
|---|---|---|---|
| 54 | 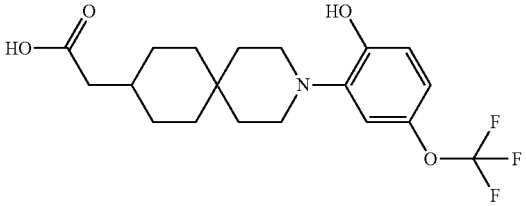 [SMILES: O=C(O)CC1CCC2(CC1)CCN(c1cc(OC(F)(F)F)ccc1O)CC2] | 388.52 | 681 |
| 55 | 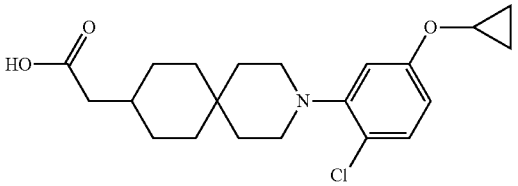 | 378.2 | 869 |
| 56 | 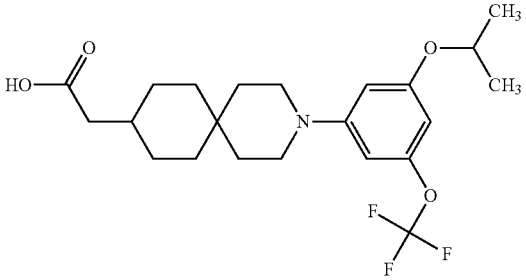 [SMILES: CC(C)Oc1cc(OC(F)(F)F)cc(N2CCC3(CCC(CC(=O)O)CC3)CC2)c1] | 430.2 | 1215 |
| 57 | 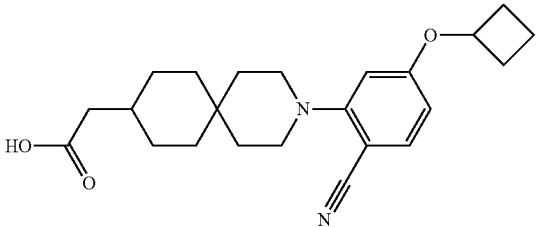 [SMILES: N#Cc1ccc(OC2CCC2)cc1N1CCC2(CCC(CC(=O)O)CC2)CC1] | 383.5 | 1328 |
| 58 | 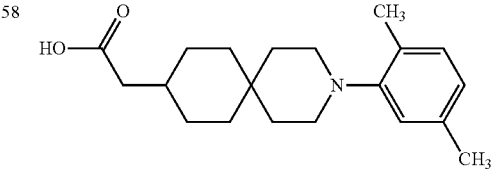 | 316.2 | 1442 |
| 59 | 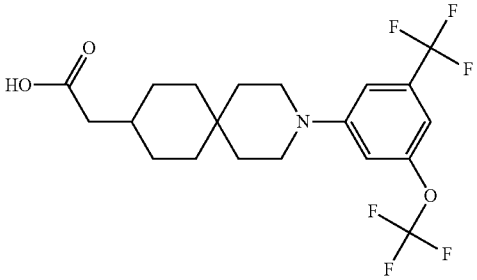 [SMILES: O=C(O)CC1CCC2(CC1)CCN(c1cc(OC(F)(F)F)cc(C(F)(F)F)c1)CC2] | 440.2 | 1488 |

TABLE 1-continued

| Ex. # | Structure | LCMS [M + H]+ | GPR120 Human EC$_{50}$ (nM) |
|---|---|---|---|
| 60 | 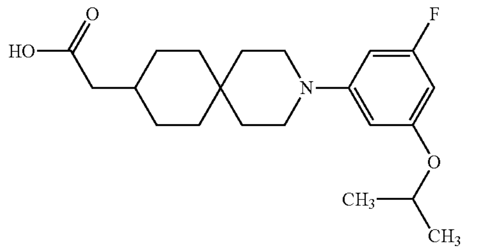 [SMILES: CC(C)Oc1cc(F)cc(N2CCC3(CCC(CC(=O)O)CC3)CC2)c1] | 364.2 | 1551 |
| 61 | 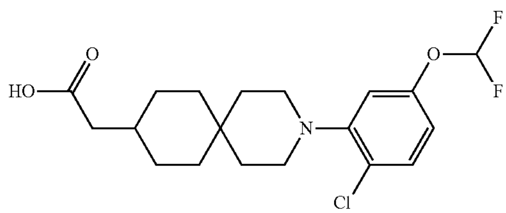 [SMILES: O=C(O)CC1CCC2(CC1)CCN(c1cc(OC(F)F)ccc1Cl)CC2] | 388.1 | 1955 |
| 62 | 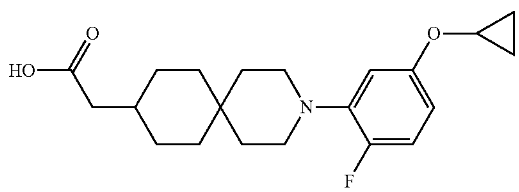 [SMILES: O=C(O)CC1CCC2(CC1)CCN(c1cc(OC3CC3)ccc1F)CC2] | 362.2 | 2149 |
| 63 | 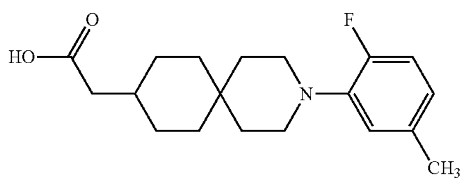 [SMILES: Cc1ccc(F)c(N2CCC3(CCC(CC(=O)O)CC3)CC2)c1] | 320.2 | 2315 |
| 64 | 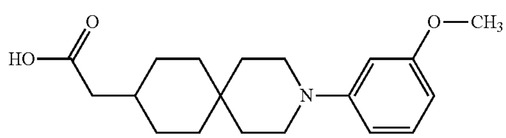 | 318.2 | 2399 |
| 65 | 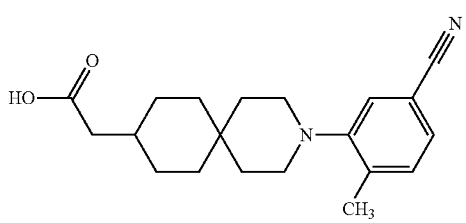 | 327.2 | 2505 |
| 66 | 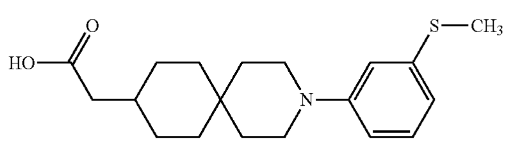 [SMILES: COc1cccc(N2CCC3(CCC(CC(=O)O)CC3)CC2)c1] | 361.2 | 2578 |
| 67 | 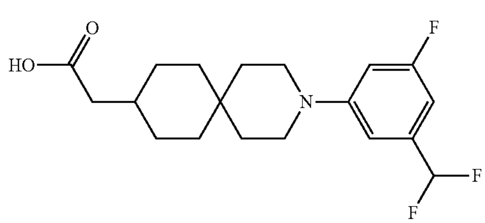 [SMILES: O=C(O)CC1CCC2(CC1)CCN(c1cc(F)cc(C(F)F)c1)CC2] | 332.2 | 2636 |

TABLE 1-continued

| Ex. # | Structure | LCMS [M + H]+ | GPR120 Human EC$_{50}$ (nM) |
|---|---|---|---|
| 68 | 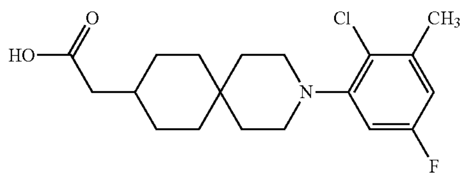 [SMILES: Cc1cc(F)cc(N2CCC3(CCC(CC(=O)O)CC3)CC2)c1Cl] | 354.2 | 2864 |
| 69 | 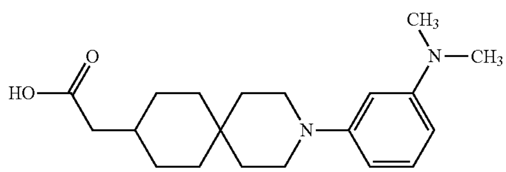 [SMILES: CN(C)c1cccc(N2CCC3(CCC(CC(=O)O)CC3)CC2)c1] | 331.2 | 2935 |
| 70 | 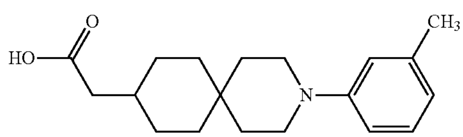 [SMILES: Cc1cccc(N2CCC3(CCC(CC(=O)O)CC3)CC2)c1] | 302.2 | 2953 |
| 71 | 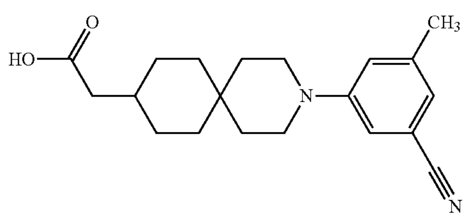 [SMILES: Cc1cc(C#N)cc(N2CCC3(CCC(CC(=O)O)CC3)CC2)c1] | 327.2 | 2955 |
| 72 | 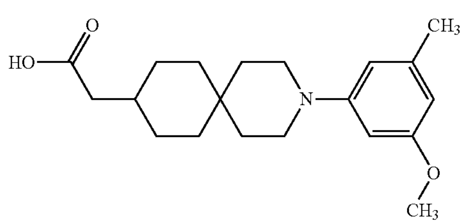 [SMILES: COc1cc(C)cc(N2CCC3(CCC(CC(=O)O)CC3)CC2)c1] | 332.2 | 3062 |
| 73 | 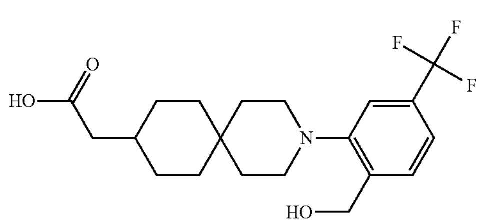 [SMILES: O=C(O)CC1CCC2(CC1)CCN(c1cc(C(F)(F)F)ccc1CO)CC2] | 386.2 | 3172 |
| 74 | 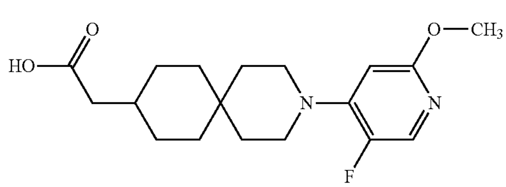 [SMILES: COc1cc(N2CCC3(CCC(CC(=O)O)CC3)CC2)c(F)cn1] | 337.2 | 3420 |

TABLE 1-continued

| Ex. # | Structure | LCMS [M + H]+ | GPR120 Human EC$_{50}$ (nM) |
|---|---|---|---|
| 75 | 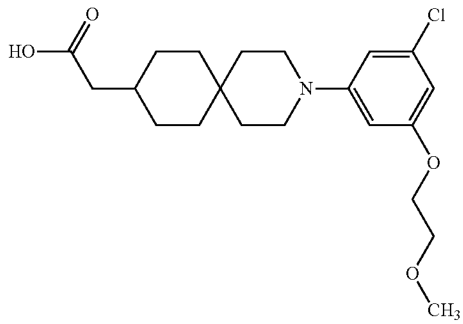 [SMILES: COCCOc1cc(Cl)cc(N2CCC3(CCC(CC(=O)O)CC3)CC2)c1] | 396.2 | 3630 |
| 76 | 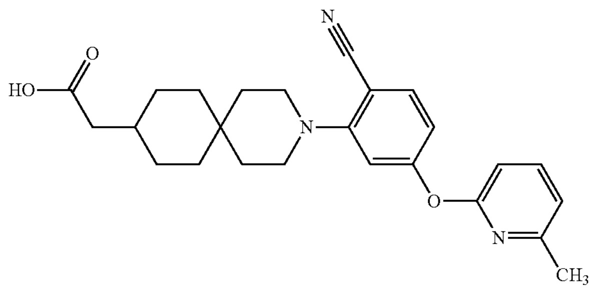 [SMILES: Cc1cccc(Oc2ccc(C#N)c(N3CCC4(CCC(CC(=O)O)CC4)CC3)c2)n1] | 420.85 | 4219 |
| 77 | 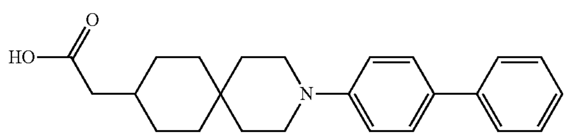 | 364.32 | 4940 |
| 78 | 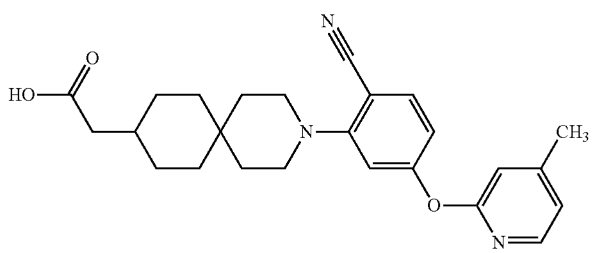 [SMILES: Cc1ccnc(Oc2ccc(C#N)c(N3CCC4(CCC(CC(=O)O)CC4)CC3)c2)c1] | 421.7 | 4969 |
| 79 | 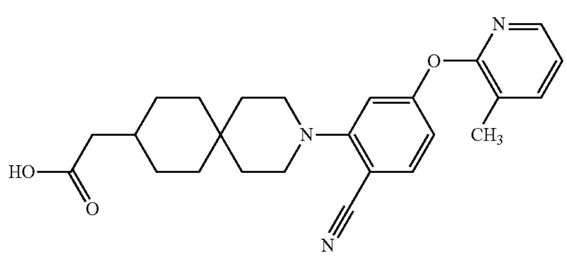 [SMILES: Cc1cccnc1Oc1ccc(C#N)c(N2CCC3(CCC(CC(=O)O)CC3)CC2)c1] | 420.4 | 6570 |
| 80 | 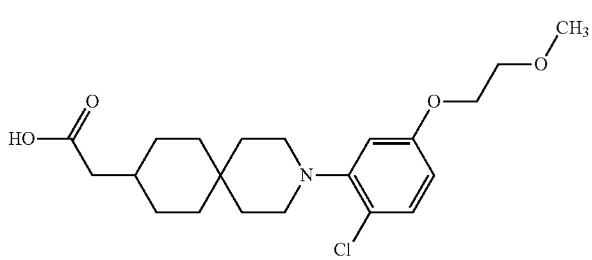 [SMILES: COCCOc1ccc(Cl)c(N2CCC3(CCC(CC(=O)O)CC3)CC2)c1] | 396.2 | 6973 |

TABLE 1-continued
| Ex. # | Structure | LCMS [M + H]+ | GPR120 Human EC$_{50}$ (nM) |
|---|---|---|---|
| 81 | 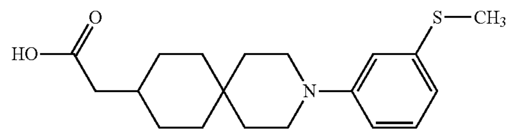 [SMILES: CSc1cccc(N2CCC3(CCC(CC(=O)O)CC3)CC2)c1] | 338.2 | 2578 |
EXAMPLE 82
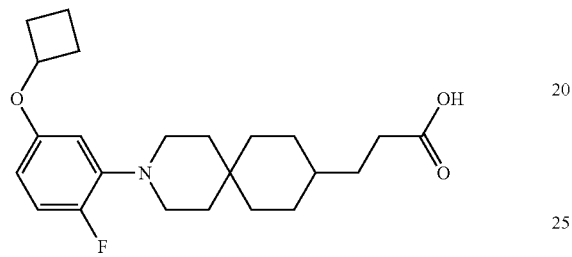
Preparation of 3-(3-(5-Cyclobutoxy-2-fluorophenyl)-3-azaspiro[5.5]undecan-9-yl)propanoic acid
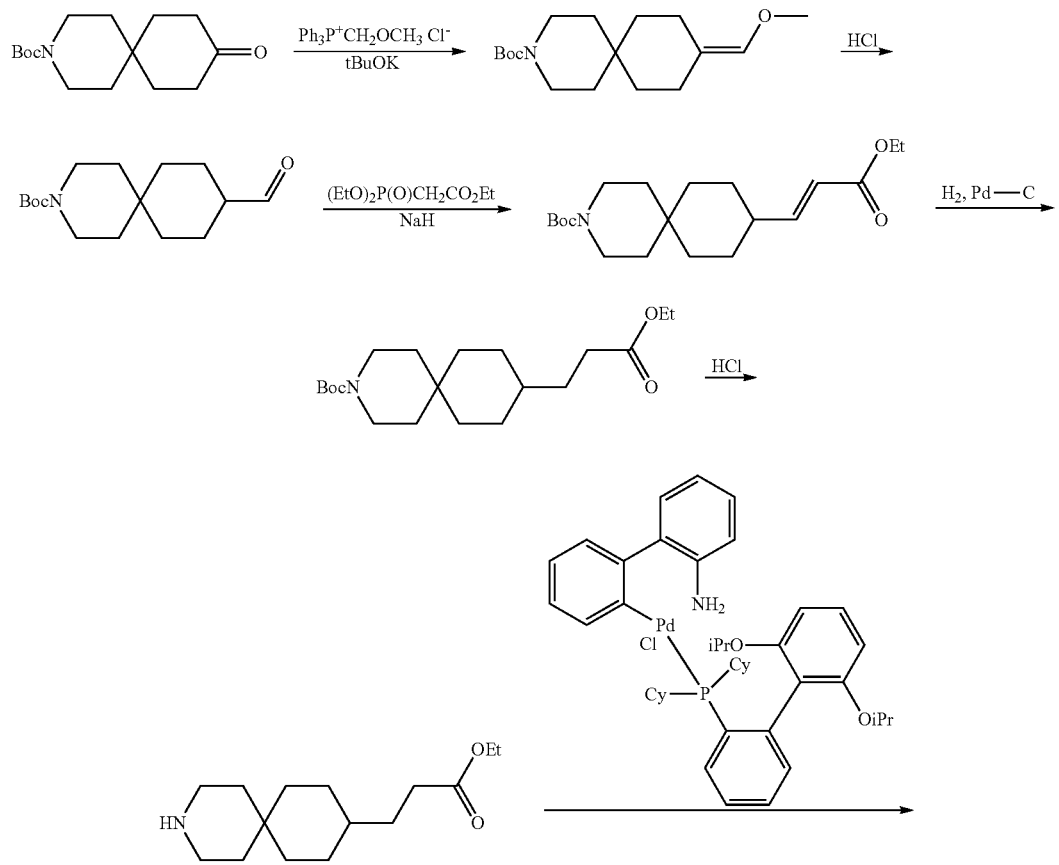

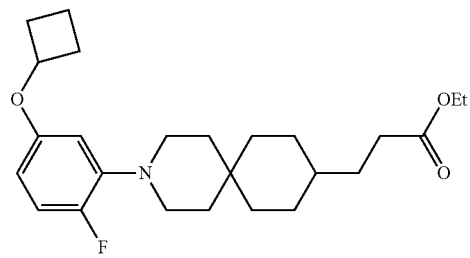 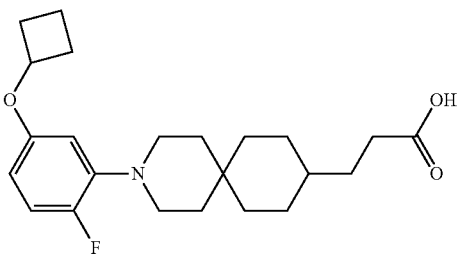 [SMILES: O=C(O)CCC1CCC2(CC1)CCN(c1cc(OC3CCC3)ccc1F)CC2]

82

Step A. tert-Butyl 9-(methoxymethylene)-3-azaspiro[5.5]undecane-3-carboxylate: To a suspension of (methoxymethyl)triphenylphosphonium chloride (5.13 g, 14.96 mmol) in THF (70 ml) at rt was added potassium tert-butoxide (1.679 g, 14.96 mmol) in one portion. The mixture immediately turned into a dark brown color. The mixture was stirred for 1 h at rt then tert-butyl 9-oxo-3-azaspiro[5.5]undecane-3-carboxylate (2 g, 7.48 mmol) was added in one portion as a solid. The mixture was stirred for about 1 h then diluted with aqueous ammonium chloride solution. The slurry was extracted 3 times with ethyl ether and the combined organic layer was washed with brine, dried over MgSO$_4$, filtered and evaporated to dryness. The crude product was purified by chromatography eluting with 0-10%-30% ethyl acetate-hex to give 1.71 g of tert-butyl 9-(methoxymethylene)-3-azaspiro[5.5]undecane-3-carboxylate.

Step B. tert-butyl 9-formyl-3-azaspiro[5.5]undecane-3-carboxylate: To a solution of tert-butyl 9-(methoxymethylene)-3-azaspiro[5.5]undecane-3-carboxylate (1.7 g, 5.75 mmol) in THF (20 ml) at rt was added 1M aquoues solution of HCl (2 ml, 2.00 mmol) and the mixture was stirred at rt. After 30 min. of stirring another 4 ml of 1N HCl was added and the mixture was stirred overnight at rt. The mixture was diluted with aq. sodium bicarbonate solution and extracted 3 times with ethyl acetate. The combined organic layers was washed with brine, dried over MgSO$_4$, filtered and evaporated to dryness to give tert-butyl 9-formyl-3-azaspiro[5.5]undecane-3-carboxylate.

Step C. (E)-tert-Butyl 9-(3-ethoxy-3-oxoprop-1-en-1-yl)-3-azaspiro[5.5]undecane-3-carboxylate: To a suspension of 60% dispersion of sodium hydride (0.438 g, 10.95 mmol) in mineral oil in THF (20 ml) at rt was added triethyl phosphonoacetate (2.172 ml, 10.95 mmol) and the mixture was stirred for about 10 min. The clear solution was cooled in an ice-bath and to this was added a solution of tert-butyl 9-formyl-3-azaspiro[5.5]undecane-3-carboxylate (1.54 g, 5.47 mmol) in THF (10 ml) and the mixture was stirred at 0° C. for 1 h. The reaction mixture was diluted with aqueous ammonium chloride solution and extracted 3 times with ethyl acetate. The combined organic layers was washed with brine, dried over MgSO$_4$, filtered and evaporated to dryness. The crude product was purified by chromatography eluting with 0-10%-50% ethyl acetate-hex to give (E)-tert-butyl 9-(3-ethoxy-3-oxoprop-1-en-1-yl)-3-azaspiro[5.5]undecane-3-carboxylate. LCMS m/z 352.36 [M+H]+

Step D. tert-Butyl 9-(3-ethoxy-3-oxopropyl)-3-azaspiro[5.5]undecane-3-carboxylate: A mixture of (E)-tert-butyl 9-(3-ethoxy-3-oxoprop-1-en-1-yl)-3-azaspiro[5.5]undecane-3-carboxylate (1.7 g, 4.84 mmol) and 10% Pd—C (300 mg, 0.282 mmol) in ethyl acetate (30 ml) was stirred under a hydrogen balloon for 3 h. The suspension was filtered through a CELITE™ diatomaceous earth pad and the filtrate was evaporated to dryness to give of tert-butyl 9-(3-ethoxy-3-oxopropyl)-3-azaspiro[5.5]undecane-3-carboxylate.

Step E. Ethyl 3-(3-azaspiro[5.5]undecan-9-yl)propanoate: A solution of tert-butyl 9-(3-ethoxy-3-oxopropyl)-3-azaspiro[5.5]undecane-3-carboxylate (1.61 g, 4.55 mmol) in 4N HCl (20 ml, 80 mmol) in dioxane was stirred at rt for 3 h. The solvent was evaporated to dryness and the residue was evaporated 2 times from ether to give 1.32 g of white solid. 240 mg of this solid was added to an aqueous solution of potassium carbonate and extracted 3 times with dichloromethane. The combined organic layers was washed with brine, dried over MgSO$_4$, filtered and evaporated to dryness to give thyl 3-(3-azaspiro[5.5]undecan-9-yl)propanoate. This was evaporated with toluene and used as such for the next step. LCMS m/z 254.28 [M+H]+

Step F. Ethyl 3-(3-(5-cyclobutoxy-2-fluorophenyl)-3-azaspiro[5.5]undecan-9-yl)propanoate: A mixture of ethyl 3-(3-azaspiro[5.5]undecan-9-yl)propanoate (100 mg, 0.395 mmol), cesium carbonate (386 mg, 1.184 mmol) and RuPhos biphenyl precatalyst (30.7 mg, 0.039 mmol) in 1,4-dioxane (2 ml) in a microwave reaction vial was bubble with nitrogen and the vial was sealed. The mixture was stirred in an oil-bath kept at 110° C. for 3 days. The mixture was diluted with aqueous ammonium choride solution and extracted 3 times with ethyl acetate. The combined organic layers was washed with brine, dried over MgSO$_4$, filtered and evaporated to dryness. The crude product was purified by chromatography eluting with 0-10%-30% ethyl acetate-hex to give ethyl 3-(3-(5-cyclobutoxy-2-fluorophenyl)-3-azaspiro[5.5]undecan-9-yl)propanoate. LCMS m/z 419.47 [M+H]+

Step G 3-(3-(5-Cyclobutoxy-2-fluorophenyl)-3-azaspiro[5.5]undecan-9-yl)propanoic acid A mixture of ethyl 3-(3-(5-cyclobutoxy-2-fluorophenyl)-3-azaspiro[5.5]undecan-9-yl)propanoate (63 mg, 0.151 mmol) and lithium hydroxide (18.07 mg, 0.754 mmol) in THF (0.75 ml), MeOH (0.750 ml) and water (0.750 ml) was stirred at 60° C. for 1 h. The mixture was cooled to rt, diluted with water, acidified with 1N HCl solution and extracted 3 times with ethyl acetate. The combined organic layers was washed with brine, dried over MgSO$_4$, filtered and evaporated to dryness. The crude product was purified by HPLC to give 82. LCMS m/z 390.44 [M+H]+, Human GPR120 EC$_{50}$: 1255 nM

EXAMPLE 83

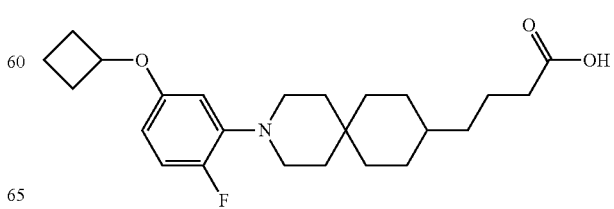

Preparation of 4-(3-(5-Cyclobutoxy-2-fluorophenyl)-3-azaspiro[5.5]undecan-9-yl)butanoic acid

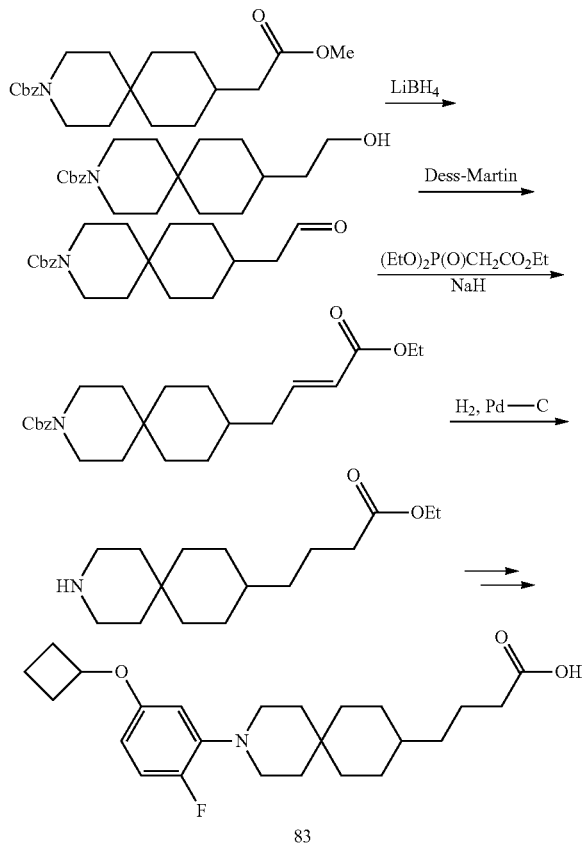

83

Step A. tert-Butyl 9-(2-hydroxyethyl)-3-azaspiro[5.5]undecane-3-carboxylate: To a solution of tert-butyl 9-(2-methoxy-2-oxoethyl)-3-azaspiro[5.5]undecane-3-carboxylate (2 g, 6.15 mmol) in THF (20 ml) at rt was added a 2M THF solution of lithium borohydride (9.22 ml, 18.44 mmol). After 1 h of stirring, another portion of lithium borohydride (9.22 ml, 18.44 mmol) was added and the mixture was stirred overnight at rt. The mixture was diluted with aqueous ammonium chloride and extracted 3 times with ethyl acetate. The combined organic layers was washed with brine, dried over MgSO$_4$, filtered and evaporated to dryness to give tert-butyl 9-(2-hydroxyethyl)-3-azaspiro[5.5]undecane-3-carboxylate.

Step B. tert-Butyl 9-(2-oxoethyl)-3-azaspiro[5.5]undecane-3-carboxylate: A mixture of tert-butyl 9-(2-hydroxyethyl)-3-azaspiro[5.5]undecane-3-carboxylate (1.65 g, 5.55 mmol) and Dess-Martin periodinane (3.53 g, 8.32 mmol) in DCM (30 ml) was stirred at rt for 2 h. The mixture was diluted with ether and stirred vigorously with aqueous sodium sulfate and aqueous sodium bicarbonate solutions. The organic phase was separated and the aqueous phase was extracted 2 times with ether. The combined organic layers was washed with brine, dried over MgSO$_4$, filtered and evaporated to dryness to give tert-butyl 9-(2-oxoethyl)-3-azaspiro[5.5]undecane-3-carboxylatE.

Step C. (E)-tert-Butyl 9-(4-ethoxy-4-oxobut-2-en-1-yl)-3-azaspiro[5.5]undecane-3-carboxylate: To a suspension of 60% sodium hydride (0.43 g, 10.90 mmol) in mineral oil in THF (20 ml) at rt was added triethyl phosphonoacetate (2.16 ml, 10.90 mmol) and the mixture was stirred for 20 min then cooled to 0° C. To this was added a solution of tert-butyl 9-(2-oxoethyl)-3-azaspiro[5.5]undecane-3-carboxylate (1.61 g, 5.45 mmol) in THF (10 ml) and the mixture was stirred for 2 h at 0° C. The solution was diluted with aquoues ammonium chloride solution and extracted 3 times with ethyl acetate. The combined organic layers was washed with brine, dried over MgSO$_4$, filtered and evaporated to dryness. The crude product was purified by chromatography eluting with 0-10%-40% ethyl aceate-hex to give (E)-tert-butyl 9-(4-ethoxy-4-oxobut-2-en-1-yl)-3-azaspiro[5.5]undecane-3-carboxylate. LCMS m/z 310.30 [M+H]+.

Step D. tert-Butyl 9-(4-ethoxy-4-oxobutyl)-3-azaspiro[5.5]undecane-3-carboxylate: A suspension of (E)-tert-butyl 9-(4-ethoxy-4-oxobut-2-en-1-yl)-3-azaspiro[5.5]undecane-3-carboxylate (1.53 g, 4.19 mmol) and 10% Pd—C (300 mg, 0.282 mmol) in ethyl acetate (30 ml) acetate was stirred under a hydrogen balloon for 4 h. The mixture was filtered through a CELITE™ diatomaceous earth pad, rinsed with ethyl acetate and evaporated to dryness. The crude product was purified by chromatography eluting with 0-10%-50% ethyl acetate-hex to give tert-butyl 9-(4-ethoxy-4-oxobutyl)-3-azaspiro[5.5]undecane-3-carboxylate. LCMS m/z 368.44 [M+H]+.

Step E. 4-(3-(5-Cyclobutoxy-2-fluorophenyl)-3-azaspiro[5.5]undecan-9-yl)butanoic acid: The above product was transformed to 83 using a procedure similar to the preparation of example 82. LCMS m/z 404.44 [M+H]+. Human GPR120 EC$_{50}$: 791 nM.

The examples in Table 2 were prepared using the similar chemistry previously described.

TABLE 2

| Ex. # | Structure | LCMS [M + H]+ | GPR120 Human EC$_{50}$ (nM) |
|---|---|---|---|
| 84 | 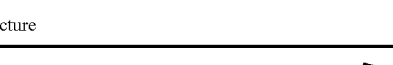 | 406.4 | 1352 |

TABLE 2-continued

| Ex. # | Structure | LCMS [M + H]+ | GPR120 Human EC$_{50}$ (nM) |
|---|---|---|---|
| 85 | 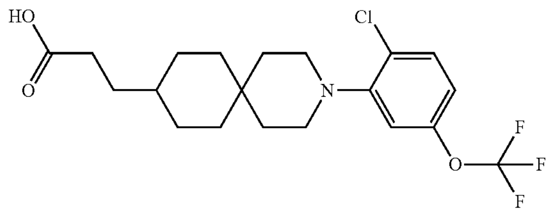 [SMILES: O=C(O)CCC1CCC2(CC1)CCN(c1cc(OC(F)(F)F)ccc1Cl)CC2] | 420.3 | 1788 |
| 86 | 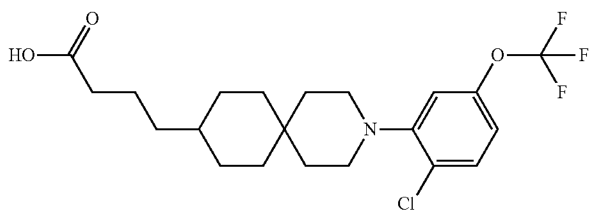 [SMILES: O=C(O)CCCC1CCC2(CC1)CCN(c1cc(OC(F)(F)F)ccc1Cl)CC2] | 434.4 | 2020 |
| 87 | 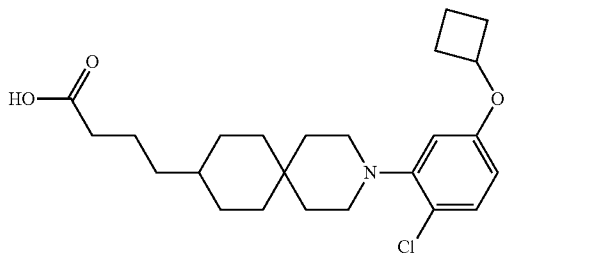 [SMILES: O=C(O)CCCC1CCC2(CC1)CCN(c1cc(OC3CCC3)ccc1Cl)CC2] | 420.4 | 2255 |

Example 88

Preparation of 2-(3-(2-Chloro-5-(trifluoromethoxy)phenyl)-8-methyl-3-azaspiro[5.5]undecan-9-yl)acetic acid (mixture of Isomers)

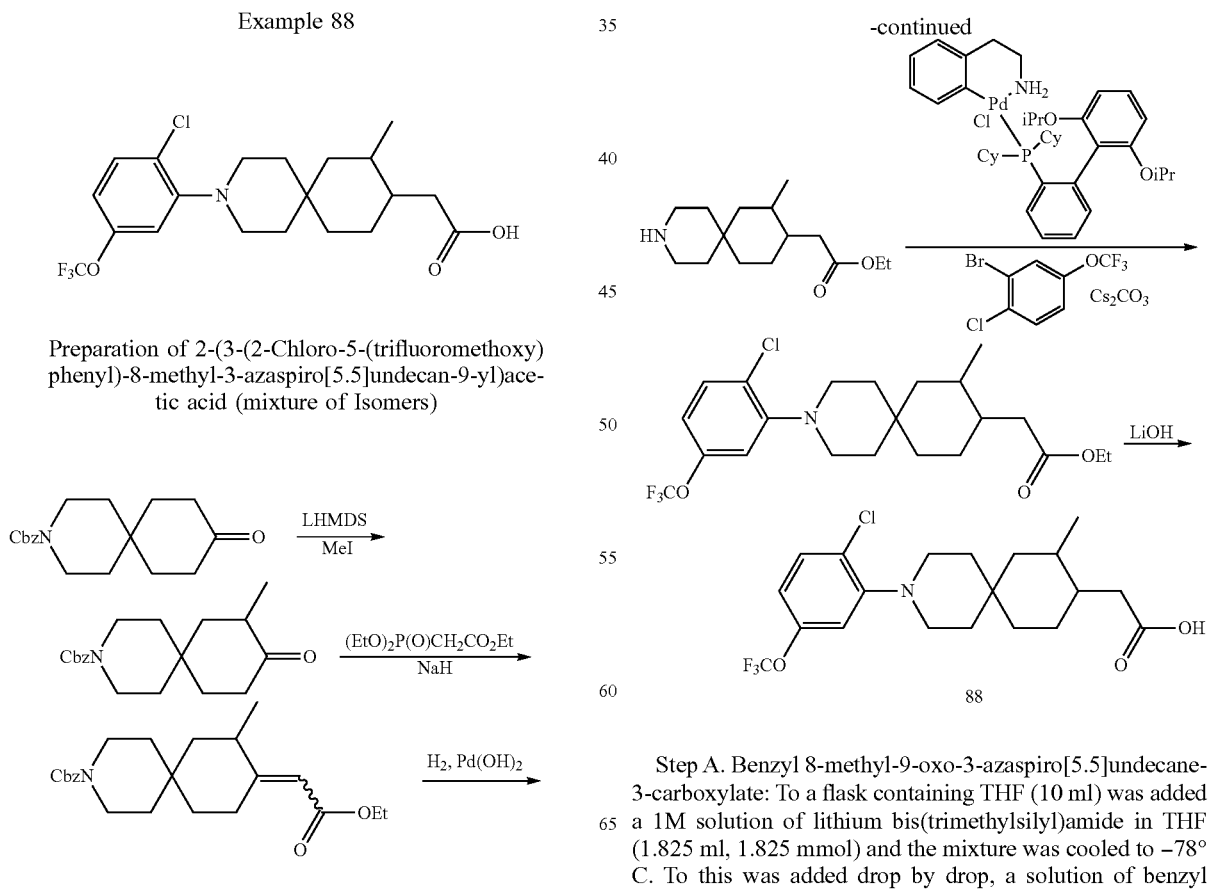

Step A. Benzyl 8-methyl-9-oxo-3-azaspiro[5.5]undecane-3-carboxylate: To a flask containing THF (10 ml) was added a 1M solution of lithium bis(trimethylsilyl)amide in THF (1.825 ml, 1.825 mmol) and the mixture was cooled to −78° C. To this was added drop by drop, a solution of benzyl 9-oxo-3-azaspiro[5.5]undecane-3-carboxylate (500 mg, 1.659 mmol) in THF (5 ml). The mixture was stirred for 30 min at −78° C. and iodomethane (0.207 ml, 3.32 mmol) was added. The reaction mixture was stirred for about 2 h during which time, it was slowly allowed to warm to ~0° C. and stirred for another 30 min at rt. It was diluted with aq.NH₄Cl and extracted 3 times with ethyl acetate. The combined organic layers was washed with brine, dried over MgSO₄, filtered and evaporated to dryness. The crude product was purified by chromatography eluting with 0-30%-50% ethyl acetate-hex to give benzyl 8-methyl-9-oxo-3-azaspiro[5.5]undecane-3-carboxylate. LCMS m/z=316.12 [M+H]+.

Step B. Benzyl 9-(2-ethoxy-2-oxoethylidene)-8-methyl-3-azaspiro[5.5]undecane-3-carboxylate: To a suspension of sodium hydride (148 mg, 3.71 mmol) in THF (8 ml) at rt was added triethyl phosphonoacetate (0.736 ml, 3.71 mmol) and the suspension immediately turned in to a clear solution. The mixture was stirred for 30 min at rt, then a solution of benzyl 8-methyl-9-oxo-3-azaspiro[5.5]undecane-3-carboxylate (390 mg, 1.236 mmol) in THF (4 ml) was added at rt. The mixture was stirred overnight at rt. The reaction mixture was poured into aq. NH₄Cl solution and extracted 3 times with ethyl acetate. The combined organic layer was washed with brine, dried over MgSO₄, filtered and evaporated to dryness. The crude product was purified by chromatography eluting with 0-15%-40% ethyl acetate-hex to give benzyl 9-(2-ethoxy-2-oxoethylidene-8-methyl-3-azaspiro[5.5]undecane-3-carboxylate (mixture of E/Z isomers). LCMS m/z 386.18 [M+H]+.

Step C. Ethyl 2-(8-methyl-3-azaspiro[5.5]undecan-9-yl)acetate: To a solution of benzyl 9-(2-ethoxy-2-oxoethylidene)-8-methyl-3-azaspiro[5.5]undecane-3-carboxylate (435 mg, 1.128 mmol) in ethyl acetate (10 ml) was added 20% palladium hydroxide on carbon (90 mg, 0.128 mmol) and the suspension was stirred overnight under a hydrogen balloon. The suspension was filtered through a CELITE™ diatomaceous earth pad, rinsed with methanol and evaporated to dryness to give ethyl 2-(8-methyl-3-azaspiro[5.5]undecan-9-yl)acetate. LCMS m/z 254.18 [M+H]+.

Step D. Ethyl 2-(3-(2-chloro-5-(trifluoromethoxy)phenyl)-8-methyl-3-azaspiro[5.5]undecan-9-yl)acetate: A suspension of ethyl 2-(3-(2-chloro-5-(trifluoromethoxy)phenyl)-8-methyl-3-azaspiro[5.5]undecan-9-yl)acetate (140 mg, 0.553 mmol), cesium carbonate (540 mg, 1.66 mmol), 2-bromo-1-chloro-4-(trifluoromethoxy)benzene (0.175 ml, 1.105 mmol) and (RuPhos) palladium(II) phenethylamine chloride (40.3 mg, 0.055 mmol) in 1,4-dioxane (3 ml) in a microwave reaction vial was bubbled with nitrogen. The vial was sealed and the mixture was stirred overnight in an oil bath kept at 100° C. The mixture was diluted with aq. NH₄Cl solution and extracted 3 times with ethyl acetate. The combined organic layer was washed with brine, dried over MgSO₄, filtered and evaporated to dryness. The crude product was purified by chromatography eluting with 0-10%-20% ethyl acetate-hex to give lethyl 2-(3-(2-chloro-5-(trifluoromethoxy)phenyl)-8-methyl-3-azaspiro[5.5]undecan-9-yl)acetate. LCMS m/z 448.13 [M+H]+.

Step E. 2-(3-(2-Chloro-5-(trifluoromethoxy)phenyl)-8-methyl-3-azaspiro[5.5]undecan-9-yl)acetic acid: A solution of ethyl 2-(3-(2-chloro-5-(trifluoromethoxy)phenyl)-8-methyl-3-azaspiro[5.5]undecan-9-yl)acetate (120 mg, 0.268 mmol) and lithium hydroxide monohydrate (45 mg, 1.07 mmol) in THF—MeOH—H₂O (1 mL each) was stirred in an oil-bath kept at 60° C. for 1 h. The mixture was cooled to rt, diluted with water and acidified with 1N HCl to ~pH2. The slurry was extracted 3 times with ethyl acetate, the combined organic layer was washed with brine, dried over MgSO₄, filtered and evaporated to dryness to give the title compound as a mixture of enantiomers/diastereomers. LCMS m/z 420.12 [M+H]+

EXAMPLES 88a-d

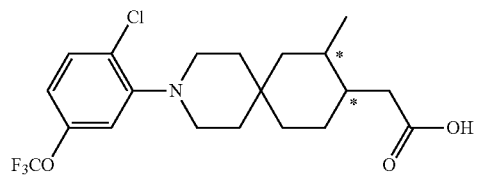 [SMILES: CC1CC2(CCC1CC(=O)O)CCN(c1cc(OC(F)(F)F)ccc1Cl)CC2]

Chiral Resolution of Example 88

2-(3-(2-Chloro-5-(trifluoromethoxy)phenyl)-8-methyl-3-azaspiro[5.5]undecan-9-yl)acetic acid (example 88) was subjected to chiral separation by SFC-HPLC on a Chiralpak AD, 30×250 mm, 18% MeOH+0.2% DEA, 70 ml/min, 10 mg/ml in MeOH to give:

EXAMPLE 88a isomer 1. LCMS m/z 420.23 [M+H]+

EXAMPLE 88b isomer 2. LCMS m/z 420.02 [M+H]+

EXAMPLE 88c isomer 3. LCMS m/z 420.05 [M+H]

EXAMPLE 88d isomer 4. LCMS m/z 420.22 [M+H]+

EXAMPLE 89

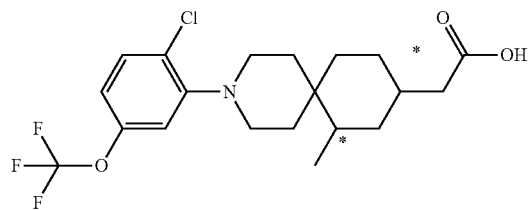 [SMILES: CC1CC(CC(=O)O)CCC12CCN(c1cc(OC(F)(F)F)ccc1Cl)CC2]

Preparation of: 2-(3-(2-Chloro-5-(trifluoromethoxy)phenyl)-7-methyl-3-azaspiro[5.5]undecan-9-yl)acetic acid

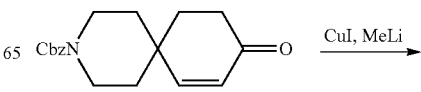

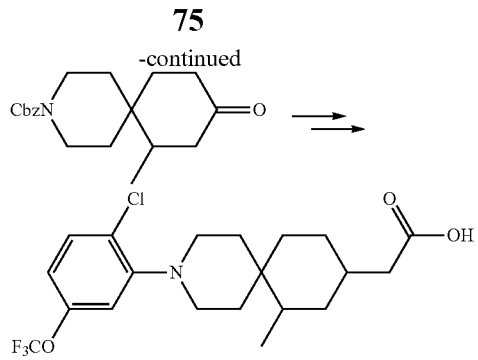

Step A. Benzyl 7-methyl-9-oxo-3-azaspiro[5.5]undecane-3-carboxylate: To s suspension of cuprous iodide (477 mg, 2.505 mmol) in THF (5 ml) at ~−40° C. (bath temp) was added a 1.6M solution of methyllithium in ether (3.13 ml, 5.01 mmol) drop by drop. As the addition progressed, the grey suspension turned into an yellow suspension which became grey again. The mixture was stirred for about 20 min at ~−40° C. then cooled to −78° C. To this was added drop by drop a solution of benzyl 9-oxo-3-azaspiro[5.5]undec-7-ene-3-carboxylate (500 mg, 1.670 mmol) in THF (3 ml+2 ml rinse). The mixture was stirred for 4 h during which time the temperature was allowed to warm from −78° C. to 0° C. It was quenched by the addition of aq. NH$_4$Cl solution and the slurry was extracted 3 times with ethyl acetate. The combined organic layers was washed with brine, dried over MgSO$_4$, filtered and evaporated to dryness. The crude product was purified by chromatography eluting with 0-30%-60% ethyl acetate-hex to give benzyl 7-methyl-9-oxo-3-azaspiro[5.5]undecane-3-carboxylate. LCMS m/z 316.15 [M+H]+.

Step B. 2-(3-(2-Chloro-5-(trifluoromethoxy)phenyl)-7-methyl-3-azaspiro[5.5]undecan-9-yl)acetic acid: The product of step A above was converted to example 89 compound (mixture of enantiomers/diastereomers) using a procedure similar to the preparation of 88. LCMS m/z=420.12 [M+H]+. Human GPR120 EC$_{50}$: 2488 nM.

EXAMPLES 89a-c

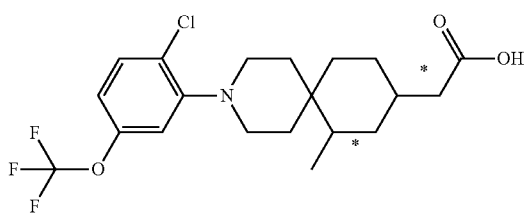 [SMILES: CC1CC(CC(=O)O)CCC12CCN(c1cc(OC(F)(F)F)ccc1Cl)CC2]

Chiral Resolution of Example 90

2-(3-(2-Chloro-5-(trifluoromethoxy)phenyl)-7-methyl-3-azaspiro[5.5]undecan-9-yl)acetic acid (example 19) was subjected to chiral separation by SFC-HPLC on a Chiralpak AD, 30×250 mm, 20% MeOH+0.2% NH$_4$OH, 70 ml/min, 10 mg/ml in MeOH.

EXAMPLE 89a isomer 1. LCMS m/z 420.00 [M+H]+ Human GPR120 EC$_{50}$: 2756 nM

EXAMPLE 89b mixture of isomers 2 and 3. LCMS m/z 420.02 [M+H]+ Human GPR120 EC$_{50}$: 3125 nM EXAMPLE 89c isomer 3. LCMS m/z 420.02 [M+H]+. Human GPR120 EC$_{50}$: 2488 nM

EXAMPLE 90

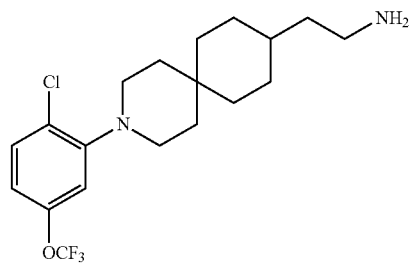 [SMILES: NCCC1CCC2(CC1)CCN(c1cc(OC(F)(F)F)ccc1Cl)CC2]

Preparation of 2-(3-(2-chloro-5-(trifluoromethoxy)phenyl)-3-azaspiro[5.5]undecan-9-yl)ethanamine

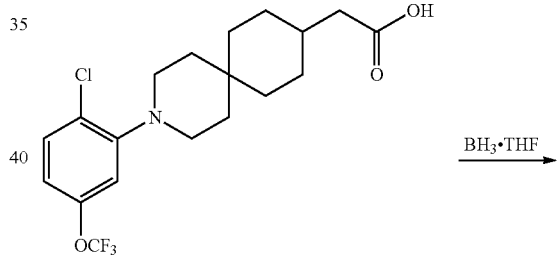

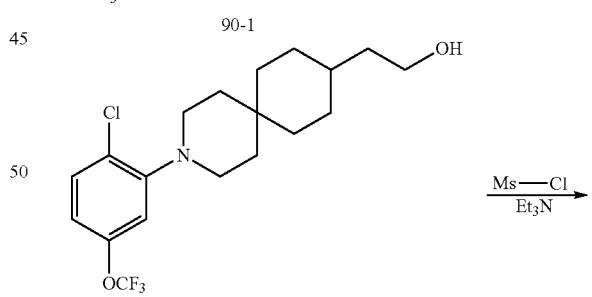

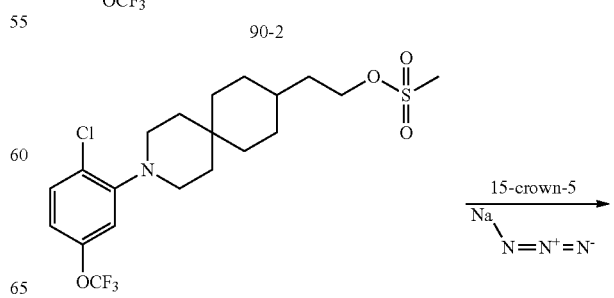

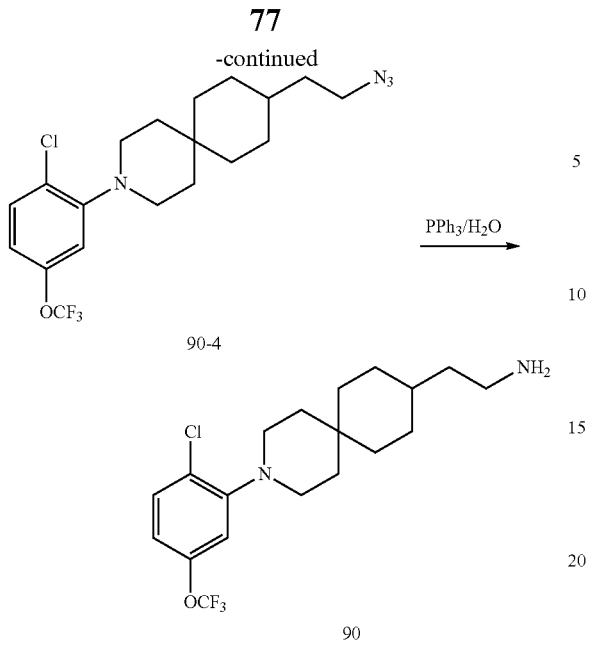

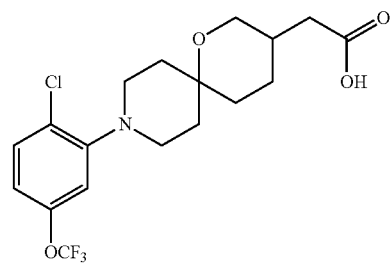 [SMILES: O=C(O)CC1CCC2(CCN(c3cc(OC(F)(F)F)ccc3Cl)CC2)OC1]

Step A: Borane tetrahydrofuran complex (18.48 mL, 18.48 mmol) was added dropwise to a stirred, cooled (0° C.) mixture of 90-1 (5.0 g, 12.32 mmol) in THF (37.000 mL) and the mixture was stirred overnight under nitrogen while slowly warming to room temperature. The reaction mixture was poured onto aqueous sodium hydrogen carbonate and extracted (3×) with ethyl acetate. The combined extracts were washed with brine, dried with MgSO$_4$, filtered and evaporated to dryness to give the crude product. The residue was purified by column chromatography on silica gel (Isco 80 g column), eluting with Hexanes/Ethyl Acetate ((0% to 25%)) to give 90-2. LCMS m/z 394.57 [M+H]+

Step B Triethyl amine (3.12 ml, 22.39 mmol) was added to a stirred, cooled (−10° C.) mixture of 90-2 (3.51 g, 8.96 mmol) in DCM (44.8 ml) followed by methanesulfonyl chloride (1.396 ml, 17.91 mmol) and the mixture was stirred for 1 h. under nitrogen. The reaction mixture was poured onto aqueous sodium hydrogen carbonate and extracted (3×) with dichloromethane. The combined extracts were washed with brine, dried with MgSO$_4$, filtered and evaporated to dryness. The residue was purified by column chromatography on silica gel (Isco 80 g column), eluting with Hexanes/Ethyl Acetate ((0% to 20%)) to give 90-3. LCMS m/z 472.29 [M+H]+

Step C To 90-3 (3.1 g, 6.60 mmol) in DMF (33.0 ml) was added 15-crown-5 (0.145 g, 0.660 mmol) and sodium azide (0.643 g, 9.89 mmol) and the mixture heated to 50° C. while stirring under nitrogen for 2 h. The reaction mixture was poured onto water and extracted (3×) with ethyl acetate. The combined extracts were washed with brine, dried with MgSO$_4$, filtered and evaporated to dryness. The residue was purified by column chromatography on silica gel (Isco 40 g column), eluting with Hexanes/Ethyl Acetate ((0% to 10%)) to give 90-4. LCMS m/z 417.75 [M+H]+

Step D: Triphenylphosphine (2.171 g, 8.28 mmol) (2.76 g of resin bound triphenyl phosphine, 3 mmols/g) was added to 90-4 (1.15 g, 2.76 mmol) in THF (13.79 ml) followed by water (0.149 ml, 8.28 mmol) and the mixture was stirred overnight under nitrogen at room temperature. The reaction mixture was filtered and the resin rinsed with THF. The filtrate was evaporated to dryness and placed on a high vacuum yielding 90. LCMS m/z 391.57 [M+H]+ Human GPR120 EC$_{50}$: 5607 nM

EXAMPLE 91

Preparation of 2-(9-(2-chloro-5-(trifluoromethoxy) phenyl)-1-oxa-9-azaspiro[5.5]undecan-3-yl)acetic acid

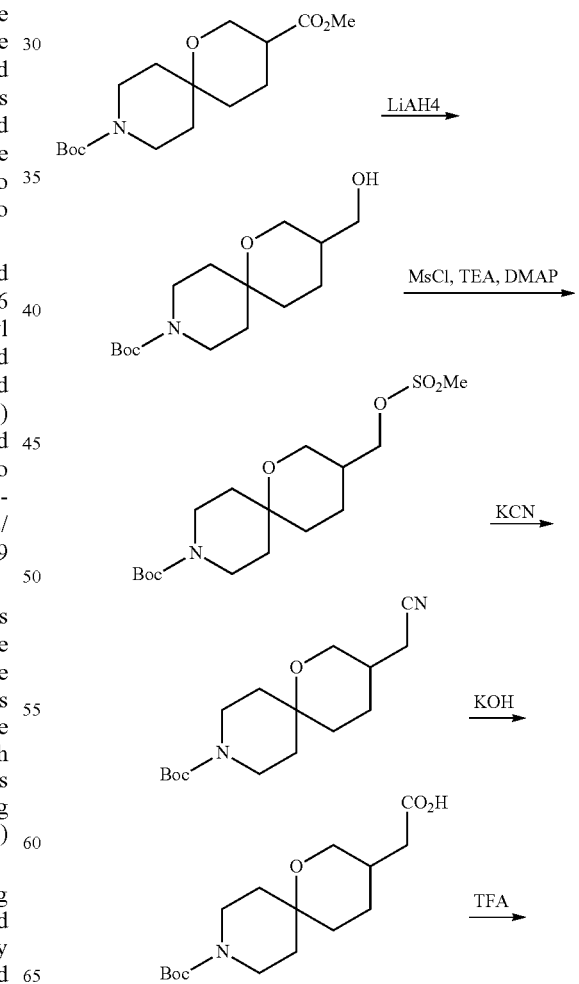

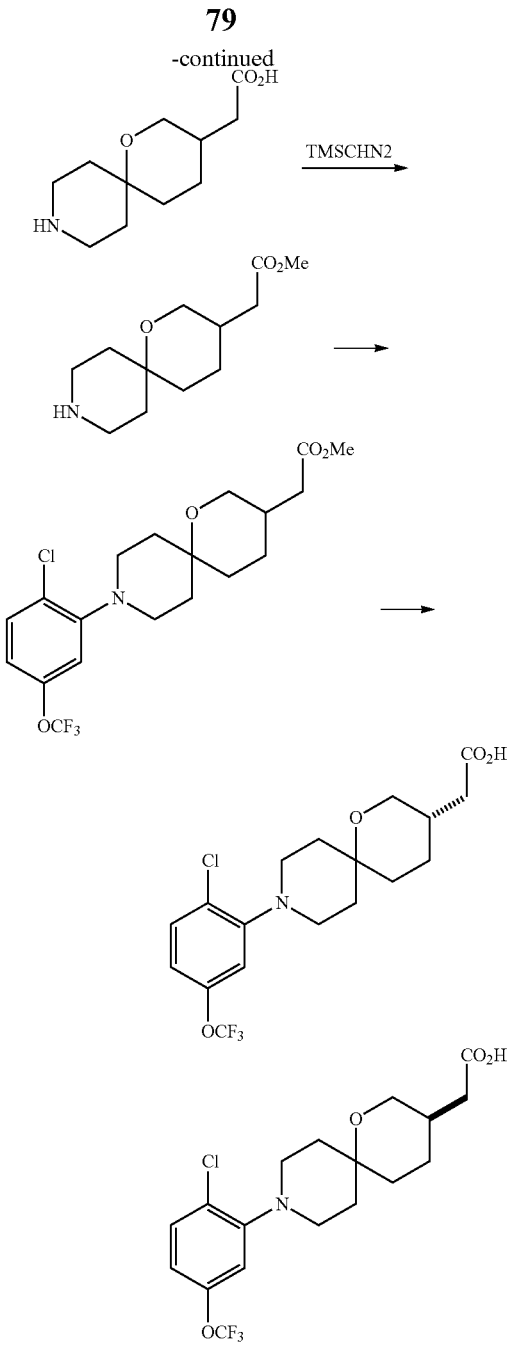

Step A. Racemic tert-butyl 3-(hydroxymethyl)-1-oxa-9-azaspiro[5.5]undecane-9-carboxylate: To a solution of 9-tert-butyl 3-methyl 1-oxa-9-azaspiro[5.5]undecane-3,9-dicarboxylate (23 g, 73.4 mmol) (for synthetic route for this reagent, see: Cernak, T.; Dykstra, K.; Levorse, D.; Verras, A.; Balkovec, J.; Nargund, R.; DeVita, R. Tetrahedron Lett. 2011, 52, 6457-6459.) in THF (50 mL) was added slowly at rt lithium aluminum hydride in THF (55.0 ml, 110 mmol) over 30 min. The resultant was stirred at rt for 0.5 h. The mixture was cooled to 0° C., quenched with 5 ml of water dropwise until the mixture was like frozen solid, then added 5 mL of 5 N NaOH. The mixture was stirred at rt for 40 min, filtered off the solid and washed with EtOAc. The combined organic solution was dried over anhydrous MgSO4, filtered, and concentrated to give the title compound.

Step B. Racemic tert-butyl 3-(((methylsulfonyl)oxy)methyl)-1-oxa-9-azaspiro[5.5]undecane-9-carboxylate: To the solution of the title compound from Example 91 Step A (18.37 g, 64.4 mmol) in dichloromethane (100 mL) was added methanesulfonyl chloride (6.50 ml, 84 mmol) at about −10° C., followed by addition of TEA (13.46 mL, 97 mmol) and portions of DMAP (0.786 g, 6.44 mmol). The mixture was stirred for 5 min. The reaction mixture was diluted with ether (150 ml), quenched with KHSO4 solution. The organic phase was washed with brine, dried over Na2SO4, concentrated to give the title compound.

Step C. Racemic tert-butyl 3-(cyanomethyl)-1-oxa-9-azaspiro[5.5]undecane-9-carboxylate: To the title compound from Example 91 Step B (18.75 g, 51.6 mmol) in DMSO (250 ml) was added potassium cyanide (13.44 g, 206 mmol). The reaction was heated at 90° C. for 1.5 day. The mixture was allowed to cool to rt, poured onto ~150 g ice, then 500 mL of ether was added. The organic phase was isolated, washed with brine, dried over Na2SO4, and concentrated to give the title compound.

Step D. Racemic 2-(9-(tert-butoxycarbonyl)-1-oxa-9-azaspiro[5.5]undecan-3-yl)acetic acid: To the title compound from Example 91 Step C (1 g, 3.40 mmol) in Ethanol (3 ml) was added KOH (3 ml, 30.0 mmol). The mixture was heated at 100° C. for 2 h. The reaction was allowed to cool to ambient temperature and concentrated to remove solvents. Added acetonitrile, and the resultant was cooled with ice bath, acidified with 6 N HCl to pH ~4-5, followed by addition of small amount of water to form two layers. The top layer was separated. The aqueous layer was extracted with acetonitrile twice. The combined organic layers was concentrated in vacuo to give the title compound.

Step E. Racemic 2-(1-oxa-9-azaspiro[5.5]undecan-3-yl)acetic acid: To the product from Example 91 Step D was added 1:1 of DCM/TFA, and stirred for 1 h. The solvent was removed, and the residue was desalted by using Varian ion exchange Resin Cartridge to give the title compound as a white solid.

Step F. Racemic methyl 2-(1-oxa-9-azaspiro[5.5]undecan-3-yl)acetate: To a solution of compound from Example 91 Step E (580 mg, 2.72 mmol) in a mixed solvent of dry MeOH (8 ml) and DCM (8.00 ml) was added (trimethylsilyl)diazomethane (2.72 ml, 5.44 mmol). The mixture was stirred for 1 h. AcOH (1 ml) was added to quench the reaction. The volatiles were removed in vacuo. The resulted residue was dissolved in DCM and purified by column chromatography on silica gel (DCM/MeOH/NH3 (aq.)), then EtOAc/MeOH/NH3 (aq.)) to give the title compound as a pale-yellow solid.

Step G. Racemic methyl 2-(9-(2-chloro-5-(trifluoromethoxy)phenyl)-1-oxa-9-azaspiro[5.5]undecan-3-yl)acetate: To a pressure tube was added 2-bromo-1-chloro-4-(trifluoromethoxy)benzene (485 mg, 1.760 mmol), the title compound from Example 91 Step F (200 mg, 0.880 mmol), Pd2(dba)3 (81 mg, 0.088 mmol), 2-docyclohexylphosphino-2',6'-dimethoxybiphenyl (108 mg, 0.264 mmol) and cesium carbonate (860 mg, 2.64 mmol) followed by 1,4-Dioxane (3 mL). The mixture was degassed by N2 for 5 min, then heated at 100° C. for 20 h. The mixture was filtered through CELITE™ diatomaceous earth, and washed with acetonitrile, concentrated. The afforded residue was purified by column chromatography on silica gel (EtOAc/hexane) to give the title compound.

Step H. (S)-2-(9-(2-chloro-5-(trifluoromethoxy)phenyl)-1-oxa-9-azaspiro[5.5]undecan-3-yl)acetic acid or (R)-2-(9-(2-chloro-5-(trifluoromethoxy)phenyl)-1-oxa-9-azaspiro[5.5]undecan-3-yl)acetic acid: To the solution of the title compound from Example 91 Step G (106.4 mg, 0.252 mmol) in 3:2 mixture of THF/MeOH was added lithium hydroxide monohydrate (1.261 mL, 2.52 mmol), and the mixture was stirred at rt overnight. Acidified by adding TFA. Removed the solvent. Dissolved in acetonitrile/H₂O/MeOH, the residue was purified by preparative HPLC Reverse phase (acetonitrile/H₂O+0.1% TFA) to give the racemic product of the title compound. Chiral separation (AD column with 30% MeOH (0.2% DEA)/CO₂, 70 mL/min, 100 bar) gave the 1st enantiomer as product ent A and the 2nd enantiomer as product ent B. Each isomer was repurified with reverse HPLC to give the acid form of product.

Product Enantiomer 91A: LCMS m/z 408.1 [M+H]+. ¹H NMR (600 MHz, CD₃OD) δ 7.41 (d, J=9.0 Hz, 1 H), 6.99 (s, 1 H), 6.91 (d, J=9.0 Hz, 1 H), 3.73 (m, 1 H), 3.39 (m, 1 H), 3.05 (m, 3 H), 2.93 (m, 1 H), 2.22 (m, 3 H), 1.99 (m, 1 H), 1.77 (m, 3 H), 1.65 (m, 2 H), 1.49 (m, 2 H). Human GPR120 EC₅₀: 636 nM Product Enantiomer 91B: LCMS m/z 408.1 [M+H]+. ¹H NMR (600 MHz, CD₃OD) δ 7.41 (d, J=9.0 Hz, 1 H), 6.99 (s, 1 H), 6.90 (d, J=9.0 Hz, 1 H), 3.73 (m, 1 H), 3.39 (m, 1 H), 3.05 (m, 3 H), 2.92 (m, 1 H), 2.22 (m, 3 H), 1.99 (m, 1 H), 1.77 (m, 3 H), 1.65 (m, 2 H), 1.49 (m, 2 H). Human GPR120 EC₅₀:1020 nM

EXAMPLE 92

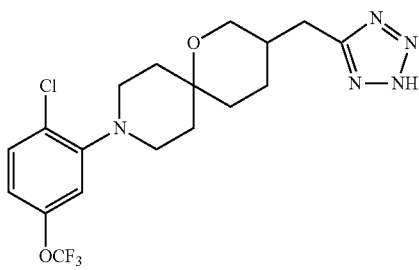 [SMILES: FC(F)(F)Oc1ccc(Cl)c(N2CCC3(CCC(Cc4nn[nH]n4)CO3)CC2)c1]

Preparation of Racemic 3-((2H-tetrazol-5-yl)methyl)-9-(2-chloro-5-(trifluoromethoxy)phenyl)-1-oxa-9-azaspiro[5.5]undecane

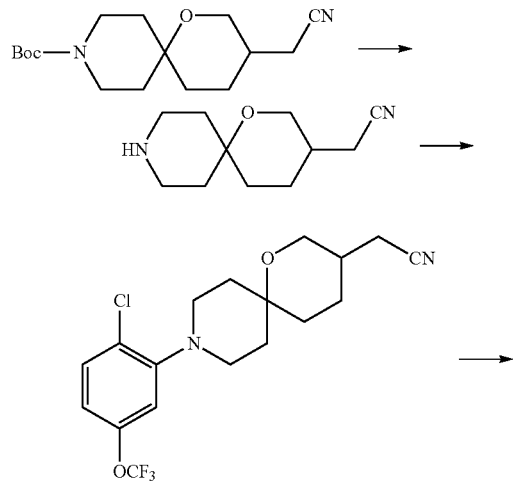

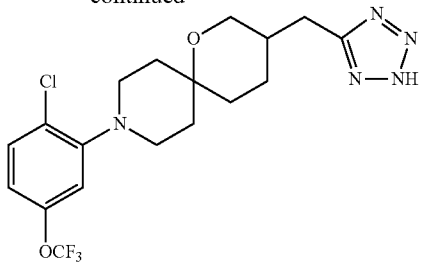

Step A. Racemic 2-(1-oxa-9-azaspiro[5.5]undecan-3-yl)acetonitrile: The title compound from Example 91 Step C (1 g, 3.4 mmol) was dissolved in a mixed solvent of 1:1 of TFA/DCM and stirred for 30 min. The solution was concentrated in vacuo, and the resulted residue was desalted by using Varian ion exchange resin cartridge to give the title compound as free base form.

Step B. Racemic 2-(9-(2-chloro-5-(trifluoromethoxy)phenyl)-1-oxa-9-azaspiro[5.5]undecan-3-yl)acetonitrile: To a pressure tube was added 2-bromo-1-chloro-4-(trifluoromethoxy)benzene (567 mg, 2.059 mmol), the title compound from Example 92 Step A (200 mg, 1.029 mmol), Pd₂(dba)₃ (94 mg, 0.103 mmol), 2-dicyclohexylphosphino-2',6'-dimethoxybiphenyl (127 mg, 0.309 mmol) and cesium carbonate (1006 mg, 3.09 mmol) followed by 1,4-Dioxane (3 ml). Degassed by N₂ for 5 min, then heated at 100° C. for 2 days. The mixture was filtered through CELITE™ diatomaceous earth, and washed with DCM. The residue was purified by flash chromatography on silica gel (EtOAc/hexane) to give the title compound.

Step C. Racemic 3-((2H-tetrazol-5-yl)methyl)-9-(2-chloro-5-(trifluoromethoxy)phenyl)-1-oxa-9-azaspiro[5.5]undecane: To a mixture of the title compound from Example 92 Step B (54 mg, 0.139 mmol) in NMP (1.4 mL), Acetic Acid (0.400 mL) and H₂O (0.200 ml) was added sodium azide (181 mg, 2.78 mmol) and trimethylamine hydrochloride (66.4 mg, 0.694 mmol). The afforded mixture was microwave irradiated at 220° C. for 9 min. Then the resultant mixture was acidified by adding conc. HCl. The mixture was concentrated, and the resulted residue was purified by flash chromatography on silica gel (DCM/MeOH/NH₃ (aq.)) to give the title compound. LCMS m/z 432.1 [M+H]+. ¹H NMR (500 MHz, CD₃OD) δ 7.42 (d, J=10.2 Hz, 1 H), 6.98 (s, 1 H), 6.90 (d, J=10.2 Hz, 1 H), 3.71 (m, 1 H), 3.47 (m, 1 H), 3.04 (m, 3 H), 2.90 (m, 3 H), 2.26 (m, 1 H), 2.05 (m, 1 H), 1.79 (m, 2 H), 1.67 (m, 3 H), 1.50 (m, 2 H). Human GPR120 EC₅₀:2630 nM EXAMPLE 93a and 93b

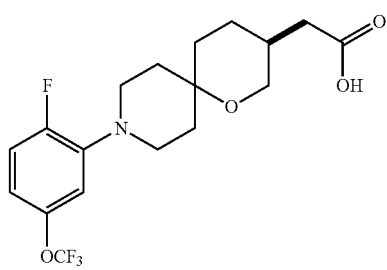

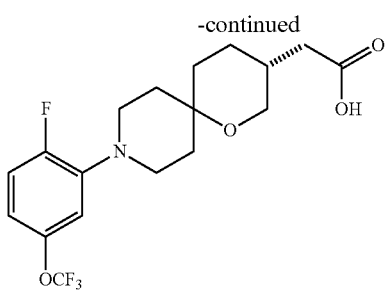

Preparation of (R) or (S) 2-(9-(2-fluoro-5-(trifluoromethoxy)phenyl)-1-oxa-9-azaspiro[5.5]undecan-3-yl)acetic acid

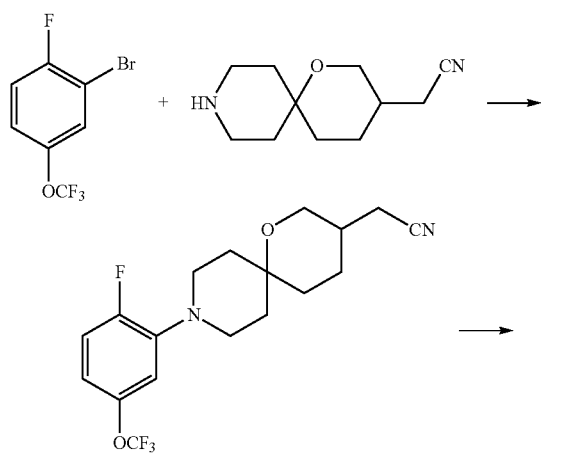

Step A. Racemic 2-(9-(2-fluoro-5-(trifluoromethoxy)phenyl)-1-oxa-9-azaspiro[5.5]undecan-3-yl)acetonitrile: To a pressure tube was added 2-bromo-1-fluoro-4-(trifluoromethoxy)benzene (0.327 mL, 2.059 mmol), the title compound from Example 92 Step A (200 mg, 1.029 mmol), Pd$_2$(dba)$_3$ (94 mg, 0.103 mmol), 2-dicyclohexylphosphino-2',6'-dimethoxybiphenyl (127 mg, 0.309 mmol) and cesium carbonate (1006 mg, 3.09 mmol) followed by 1,4-Dioxane (3 ml). Degassed by N$_2$ for 5 min, then heated at 100° C. for 2 days. The mixture was filtered through CELITE™ diatomaceous earth, and washed with DCM. The residue was purified by flash chromatography on silica gel (EtOAc/hexane) to give the title compound.

Step B. (S)-2-(9-(2-fluoro-5-(trifluoromethoxy)phenyl)-1-oxa-9-azaspiro[5.5]undecan-3-yl)acetic acid or (R)-2-(9-(2-fluoro-5-(trifluoromethoxy)phenyl)-1-oxa-9-azaspiro[5.5]undecan-3-yl)acetic acid: To the title compound from Example 93 Step A (43 mg, 0.115 mmol) in EtOH (1 mL) was added potassium hydroxide (1 mL, 10.00 mmol), heated at 100° C. for 4.5 h. The mixture was allowed to cool to ambient temperature, diluted with acetonitrile, acidified with con. HCl to pH ~2. Then small amount of water was added to form two layers. The top layer was separated. The aqueous layer was extracted with acetonitrile twice. The organic layers were combined, and the volume reduced in vacuo. The solution was purified by preparative HPLC (acetonitrile/Water+0.1% TFA) to give the racemic product as a brown oil. The racemic product was subjected to chiral separation (AD column with 25% MeOH (0.2% DEA)/CO$_2$, 70 ml/min, 100 bar) to give the 1st enantiomer as ent A, and the 2nd enantiomer as ent B.

Product Enantiomer 93a: LCMS m/z 392.1 [M+H]+. $^1$H NMR (600 MHz, CD$_3$OD) δ 7.13 (dd, J=12.0, 8.4 Hz, 1 H), 6.99 (d, J=6.6 Hz, 1 H), 6.90 (d, J=8.4 Hz, 1 H), 3.73 (m, 1 H), 3.37 (m, 1 H), 3.18 (m, 3 H), 3.04 (m, 1 H), 2.22 (m, 3 H), 1.99 (m, 1 H), 1.78 (m, 3 H), 1.62 (m, 2 H), 1.48 (m, 2 H). Human GPR120 EC$_{50}$:1300 nM Product Enantiomer 93b: LCMS m/z 392.1 [M+H]+. $^1$H NMR (600 MHz, CD$_3$OD) δ 7.13 (dd, J=12.0, 8.4 Hz, 1 H), 6.99 (d, J=6.6 Hz, 1 H), 6.90 (d, J=8.4 Hz, 1 H), 3.73 (m, 1 H), 3.37 (dd, 10.2, 10.2 Hz, 1 H), 3.17 (m, 3 H), 3.04 (m, 1 H), 2.23 (m, 3 H), 1.99 (m, 1 H), 1.78 (m, 3 H), 1.62 (m, 2 H), 1.48 (m, 2 H). Human GPR120 EC$_{50}$:750 nM

EXAMPLE 94

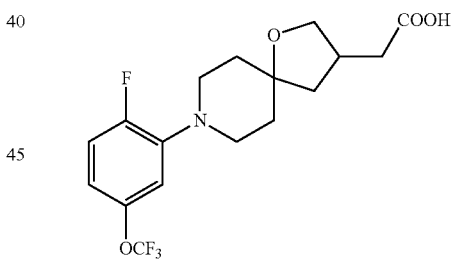

Preparation of racemic 2-(8-(2-fluoro-5-(trifluoromethoxy)phenyl)-1-oxa-8-azaspiro[4.5]decan-3-yl (acetic acid

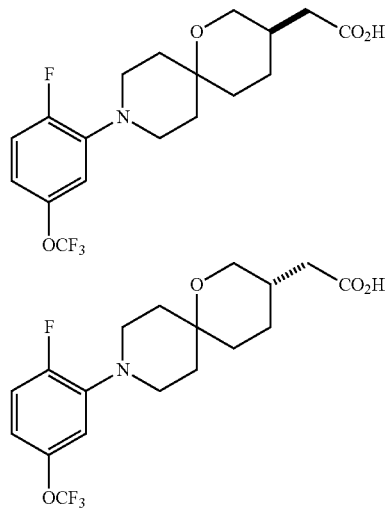

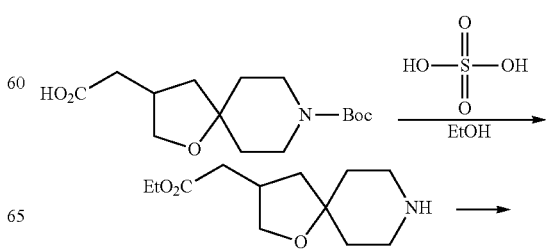

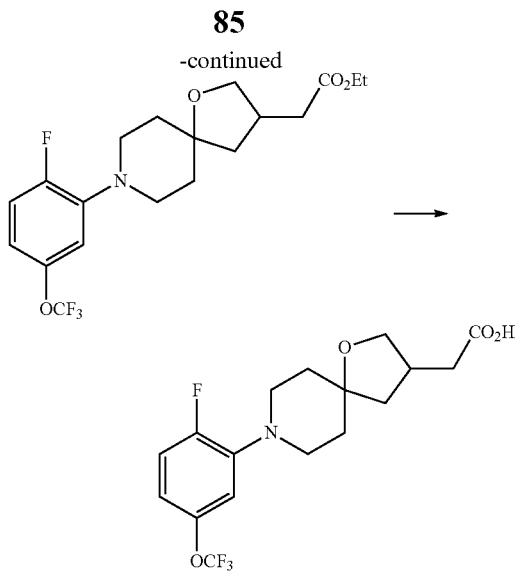

Step A. Racemic ethyl 2-(1-oxa-8-azaspiro[4.5]decan-3-yl)acetate: To a solution of 2-(8-(tert-butoxycarbonyl)-1-oxa-8-azaspiro[4.5]decan-3-yl)acetic acid (500 mg, 1.670 mmol) in EtOH (8 ml) was added sulfuric acid (0.098 mL, 1.837 mmol). The afforded solution was heated at 85° C. for 70 min. The mixture was concentrated in vacuo, then desalted by using Varian ion exchange Resin Cartridge to give the title compound in free base form.

Step B. Racemic ethyl 2-(8-(2-fluoro-5-(trifluoromethoxy)phenyl)-1-oxa-8-azaspiro[4.5]decan-3-yl)acetate: To a pressure tube was added 2-bromo-1-fluoro-4-(trifluoromethoxy)benzene (228 mg, 0.880 mmol), the title compound from Example 94 Step A (100 mg, 0.440 mmol), $Pd_2(dba)_3$ (40.3 mg, 0.044 mmol) and 2-dicyclohexylphosphino-2',6'-dimethoxybiphenyl (54.2 mg, 0.132 mmol) and cesium carbonate (430 mg, 1.320 mmol) followed by 1,4-Dioxane (3 mL). Degassed by $N_2$ for 5 min, then heated at 100° C. overnight. The mixture was allowed to cool to ambient temperature, filtered through CELITE™ diatomaceous earth, and washed with DCM. The residue was purified by flash chromatography on silica gel (EtOAc/hexane) to give the title compound.

Step C. Racemic 2-(8-(2-fluoro-5-(trifluoromethoxy)phenyl)-1-oxa-8-azaspiro[4.5]decan-3-yl)acetic acid: To a solution of the title compound from Example 94 Step B (63.4 mg, 0.156 mmol) in 3:2 mixture of THF/MeOH was added LiOH (1.564 ml, 1.564 mmol), stirred at rt for 2 days. The solution was acidified by adding TFA. The solvents were removed in vacuo, and the resulted residue dissolved in acetonitrile/$H_2O$/MeOH. The afforded solution was purified by preparative HPLC Reverse phase (acetonitrile/$H_2O$+ 0.1% TFA) to give the title compound. LCMS m/z 378.2 [M+H]+. $^1$H NMR (600 MHz, $CD_3OD$) δ 7.10 (dd, J=12.0, 8.4 Hz, 1 H), 6.99 (d, J=7.8 Hz, 1 H), 6.85 (d, J=8.4 Hz, 1 H), 4.05 (m, 1 H), 3.48 (dd, 8.4, 8.4 Hz, 1 H), 3.16 (m, 2 H), 3.09 (m, 2 H), 2.70 (m, 1 H), 2.41 (m, 2 H), 2.13 (m, 1 H), 1.82 (m, 4 H), 1.45 (m, 1 H). Human GPR120 $EC_{50}$: 1477 nM.

The examples in Table 3 were prepared using the chemistry previously described.

TABLE 3

| EX. # | Structure | LCMS [M + H]+ | GPR120 Human $EC_{50}$ (nM) |
|---|---|---|---|
| 95 | 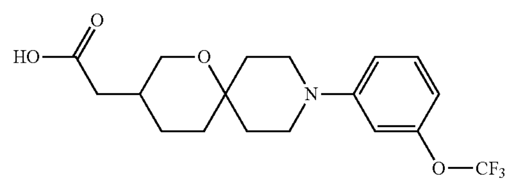 | 374.1 | 1895 |
| 96 | 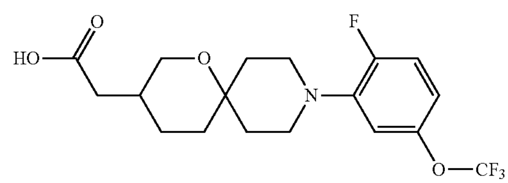 | 391.4 | 1209 |
| 97 | 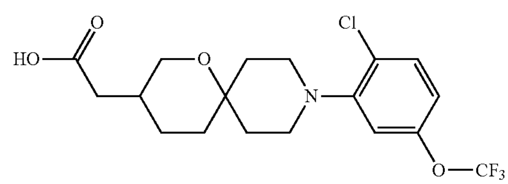 [SMILES: O=C(O)CC1CCC2(CCN(c3cc(OC(F)(F)F)ccc3F)CC2)OC1] | 407.8 | 1294 |
| 98 | 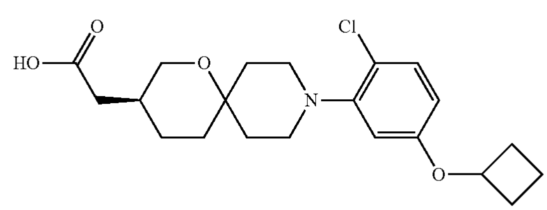 [SMILES: O=C(O)C[C@@H]1CCC2(CCN(c3cc(OC4CCC4)ccc3Cl)CC2)OC1] | 394.6 | 1533 |

TABLE 3-continued
| EX. # | Structure | LCMS [M + H]+ | GPR120 Human EC$_{50}$ (nM) |
|---|---|---|---|
| 99 | 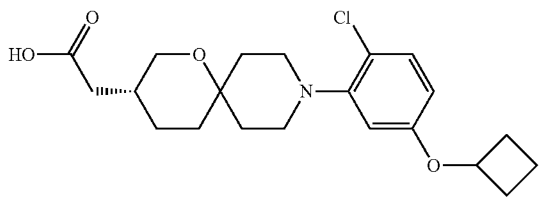 [SMILES: O=C(O)C[C@H]1CCC2(CCN(c3cc(OC4CCC4)ccc3Cl)CC2)OC1] | 395.6 | 1645 |
| 100 | 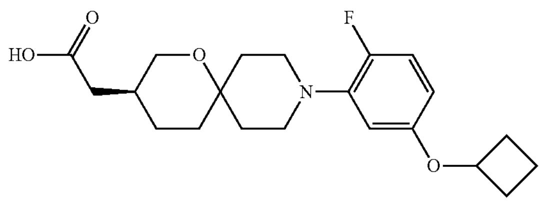 [SMILES: O=C(O)C[C@@H]1CCC2(CCN(c3cc(OC4CCC4)ccc3F)CC2)OC1] | 378.3 | 4281 |
| 101 | 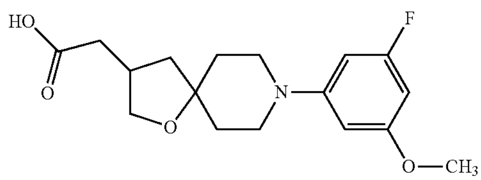 [SMILES: COc1cc(F)cc(N2CCC3(CC2)CC(CC(=O)O)CO3)c1] | 323.4 | 2378 |
| 102 | 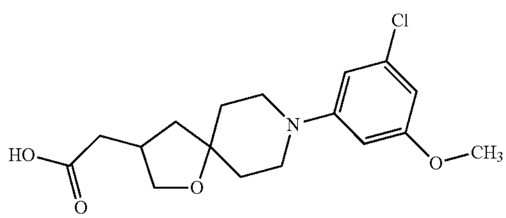 [SMILES: COc1cc(Cl)cc(N2CCC3(CC2)CC(CC(=O)O)CO3)c1] | 339.8 | 8096 |
| 103 | 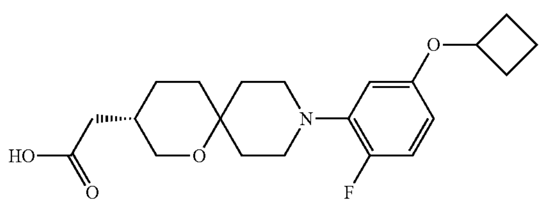 [SMILES: O=C(O)C[C@@H]1CCC2(CCN(c3cc(OC4CCC4)ccc3F)CC2)OC1] | 378.8 | 3245 |
EXAMPLE 104
Preparation of 4-(8-(2-chloro-5-(trifluoromethoxy)phenyl)spiro[4.5]decan-2-yl)butanoic acid
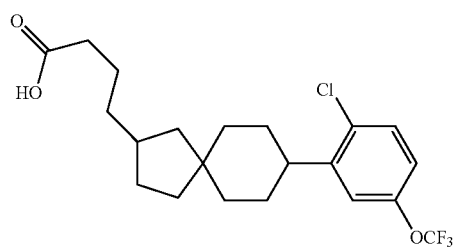 [SMILES: O=C(O)CCCC1CCC2(CCC(c3cc(OC(F)(F)F)ccc3Cl)CC2)C1]
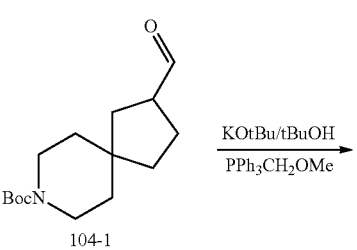
104-1
KOtBu/tBuOH
PPh$_3$CH$_2$OMe

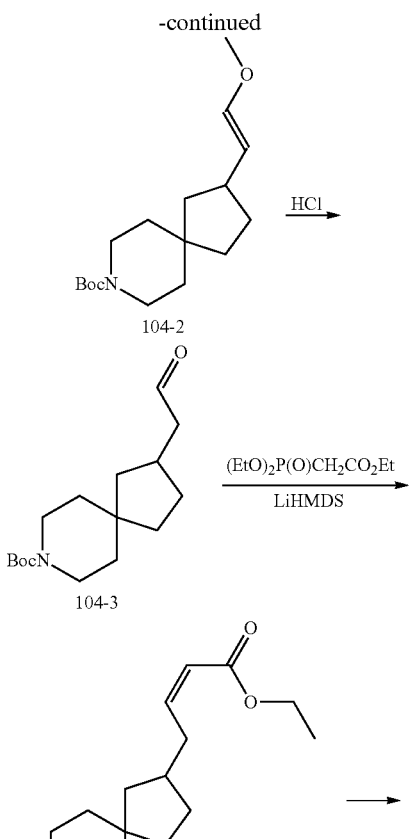

cooled (−78° C.) mixture of potassium tert-butoxide (1122 μl, 1.122 mmol) and 'BuOH (107 μl, 1.122 mmol) in THF (1870 μl) and the mixture was stirred for 10 min. under nitrogen. The mixture was then warmed to −10° C. and stirred for 30 min. The mixture was cooled to −78° C. and 104-1 (100 mg, 0.374 mmol) (as a solution in 0.5 mL of THF) was added dropwise and, after 10 minutes, the mixture was warmed to −10° C. and stirred for 2 h. The reaction mixture was poured onto water and extracted (3×) with ethyl acetate. The combined extracts were washed with brine, dried with MgSO$_4$, filtered and evaporated to dryness. The residue was purified by column chromatography on silica gel (Isco 12 g column), eluting with Hexanes/Acetone ((0% to 15%)) to give 104-2. LCMS m/z 296.51 [M+H]+

Step B: aq conc HCl (284 μl, 0.284 mmol) was added to a stirred, cooled (−10° C.) mixture of 104-2 (42 mg, 0.142 mmol) in THF (711 μl) and the mixture was, while warming to room temperature, stirred for overnight under nitrogen. The reaction mixture was poured onto aqueous sodium hydrogen carbonate and extracted (3×) with dichloromethane. The combined extracts were washed with brine, dried with MgSO$_4$, filtered and evaporated to dryness yielding 104-3. LCMS m/z 282.47 [M+H]+

Step C: LiHMDS (160 μl, 0.160 mmol) was added to a stirred, cooled (−10° C.) mixture of triethyl phosphonoacetate (38.1 μl, 0.192 mmol) in tetrahydrofuran (500 uL) and the mixture was stirred for 15 min. under nitrogen. 104-3 (36 mg, 0.128 mmol) was then added as a solution in tetrahydrofuran (500 uL) and the mixture continued to stir overnight while slowly warming to room temperature. The reaction mixture was poured onto aqueous ammonium chloride and extracted (3×) with ethyl acetate. The combined extracts were washed with brine, dried with MgSO$_4$, filtered and evaporated to dryness. The crude product was purified by preparative TLC, eluting with hexanes/ethyl acetate (4:1) yielding 104-4. LCMS m/z 352.59 [M+H]+

Step D: Pd/C (5 mg, 4.70 μmol) was added to 104-4 (15 mg, 0.043 mmol) in MeOH (2 ml) and the mixture was stirred for 1 h. under a balloon of hydrogen at room temperature. The reaction mixture was filtered through celite and evaporated to dryness yielding 104-5. LCMS m/z 354.60 [M+H]+

Step E: Compound 104-5 was converted to example 104 using conditions described in example 1 using steps D through step F. LCMS m/z 354.60 [M+H]+

EXAMPLE 105

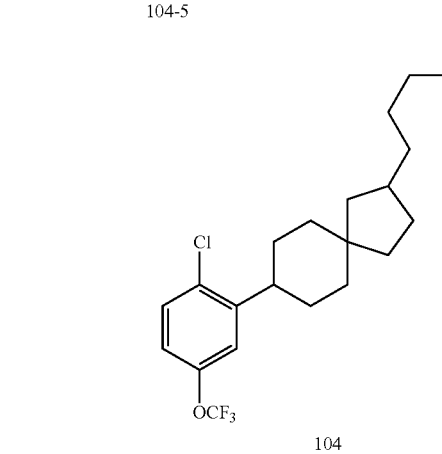

104

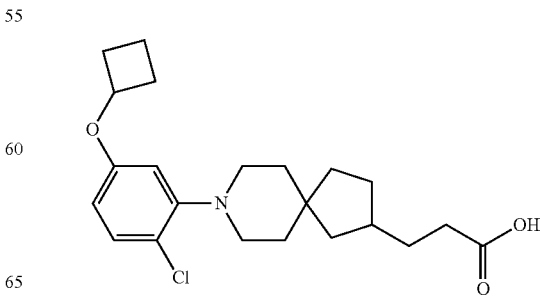

Step A: (Methoxymethyl)triphenylphosphonium chloride (385 mg, 1.122 mmol) was added in portions to a stirred,

Preparation of 3-(8-(2-chloro-5-cyclobutoxyphenyl)-8-azaspiro[4.5]decan-2-yl)propanoic acid

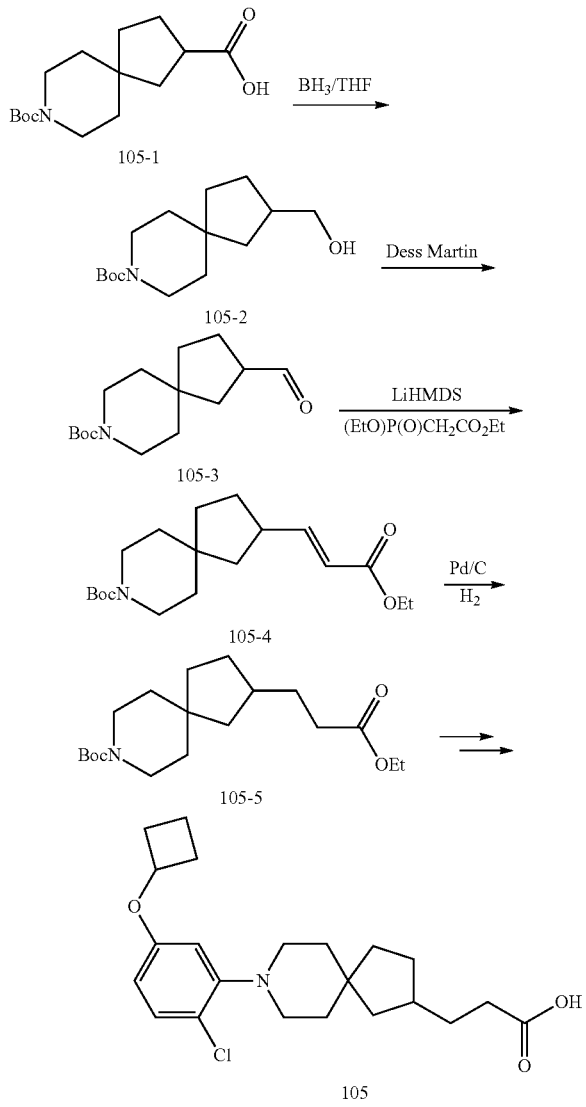

Step A. tert-Butyl 2-(hydroxymethyl)-8-azaspiro[4.5]decane-8-carboxylate: Borane-tetrahydrofuran complex (7.06 mL of 1M solution in THF, 7.06 mmol) was added to a stirred, cooled (−10° C.) mixture of 8-(tert-butoxycarbonyl)-8-azaspiro[4.5]decane-2-carboxylic acid (2.0 g, 7.06 mmol) in THF (35 mL) and the mixture was stirred overnight under nitrogen while warming to room temperature. The reaction mixture was poured onto aqueous sodium hydrogen carbonate and extracted (3×) with ethyl acetate. The combined extracts were washed with brine, dried with MgSO$_4$, filtered and evaporated to dryness yielding 105-2. LCMS m/z 270.53 [M+H]+

Step B. tert-Butyl 2-formyl-8-azaspiro[4.5]decane-8-carboxylate: Dess-Martin Periodinane (3.8 g, 8.91 mmol) was added to a stirred, cooled (−10° C.) mixture of 105-2 (2.0 g, 7.42 mmol) in DCM (37 mL) and the mixture was stirred for 5 min. under nitrogen then warmed to room temperature and stirred for another 2 hours. The reaction mixture was diluted with diethyl ether then aqueous sodium hydrogen carbonate and aqueous sodium thiosulfate were added and the mixture was stirred rapidly for 10 minutes. The mixture was then extracted (3×) with diethyl ether. The combined extracts were washed with brine, dried with MgSO$_4$, filtered and evaporated to dryness yielding 105-3. LCMS m/z 268.49 [M+H]+

Step C. (E)-tert-Butyl 2-(3-ethoxy-3-oxoprop-1-en-1-yl)-8-azaspiro[4.5]decane-8-carboxylate: LiHMDS (3.74 mL of a 1M solution in THF, 3.74 mmol) was added to a stirred, cooled (−10° C.) mixture of triethyl phosphonoacetate (1006 mg, 4.49 mmol) in THF (15.000 mL) and the mixture was stirred for 15 min. under nitrogen. A solution of 3 (800 mg, 2.99 mmol) in THF (3 mL) was added and the mixture was warmed to room temperature and stirred for a further 1 hr. The reaction mixture was poured onto aqueous ammonium chloride and extracted (3×) with ethyl acetate. The combined extracts were washed with brine, dried with MgSO$_4$, filtered and evaporated to dryness. The residue was purified by column chromatography on silica gel (Isco 24 g column), eluting with Hexanes/Acetone (0% to 10%) to give 105-4. LCMS m/z 360.63 [M+Na]+

Step D. tert-Butyl 2-(3-ethoxy-3-oxopropyl)-8-azaspiro[4.5]decane-8-carboxylate: Pd/C (120 mg, 0.056 mmol) (10% Pd on Carbon, 50% water) was added to 105-4 (620 mg, 1.837 mmol) in MeOH (15 ml) and the mixture was stirred for 45 min. under a balloon of hydrogen at room temperature. The mixture was then filtered and evaporated to dryness yielding 105-5. LCMS m/z 262.66 [M+Na]+

Step E. 3-(8-(2-Chloro-5-cyclobutoxyphenyl)-8-azaspiro[4.5]decan-2-yl)propanoic acid: Compound 5 was converted to example 105 following procedures described in example 1 using steps D through F. LCMS m/z 392.6 [M+H]+. hGPR120 EC$_{50}$=44.8 nM (IP1 Assay)

The examples in Table 4 were prepared using the chemistry previously described.

TABLE 4

| EX. # | Structure | LCMS [M + H]+ | GPR120 Human EC$_{50}$(nM) (IP1 Assay) |
|---|---|---|---|
| 106 | HOOC—[structure]—NC, O—CF$_3$ | 397.5 | 220 |

TABLE 4-continued

| EX. # | Structure | LCMS [M + H]+ | GPR120 Human EC$_{50}$(nM) (IP1 Assay) |
|---|---|---|---|
| 107 | 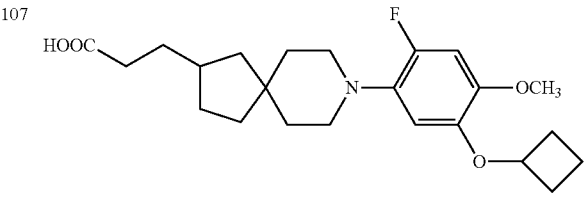 | 406.6 | 202 |

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size 0 hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound according to the formula:

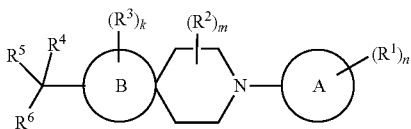

or a pharmaceutically acceptable salt thereof, wherein:
ring A is phenyl;
ring B is a cyclohexyl ring, wherein the cyclohexyl ring forms a spiro ring system with the adjoining piperidinyl ring;
each $R^1$ is
  (1) halo,
  (2) $(C_{1-6})$alkyl,
  (3) halo$(C_{1-6})$alkyl,
  (4) hydroxy$(C_{1-6})$alkyl,
  (5) $(C_{1-6})$alkoxy,
  (6) halo$(C_{1-6})$alkoxy,
  (7) $(C_{1-2})$alkoxy-$(C_{1-6})$alkoxy,
  (8) $(C_{1-6})$alkyl-S—,
  (9) halo$(C_{1-6})$alkyl-S—,
  (10) nitro,
  (11) $(C_{3-7})$cycloalkyl-O—,
  (12) cyano,
  (13) hydroxy,
  (14) $(C_{1-6})$alkylC(O)—,
  (15) $((C_{1-6})$alkyl$)_2$N—,
  (16) phenyl, or
  (17) 5- or 6-membered heteroaryloxy ring, containing 1-3 O, N, and S ring atoms,
wherein the phenyl and heteroaryloxy, groups are optionally substituted by 1-3 $(C_{1-6})$alkyl, halo$(C_{1-6})$alkyl, or halo groups; or alternatively two $R^1$ groups are linked together with the carbon to which they are both attached to form

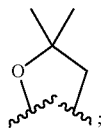;

each $R^2$ and $R^3$ are independently
  (1) $(C_{1-6})$alkyl,
  (2) halo$(C_{1-6})$alkyl,
  (3) $(C_{1-6})$alkoxy,
  (4) halo$(C_{1-6})$alkoxy,
  (5) hydroxyl, or
  (6) halo;
$R^4$ and $R^5$ are independently
  (1) hydrogen,
  (2) $(C_{1-6})$alkyl,
  (3) halo$(C_{1-6})$alkyl, or
  (4) halo;
$R^6$ is
  (1) COOH,
  (2) tetrazolyl,
  (3) —$(C_{1-3})$alkylCOOH,
  (4) $(C_{1-4}$alkylNH$_2$, or
  (5) $(C_{1-4})$alkylOH;

q is 0, 1, or 2;
k is 0, 1, 2, or 3;
m is 0, 1, 2, or 3; and
n is 1, 2, or 3.

2. The compound of claim 1, or a pharmaceutically acceptable salt thereof, wherein each $R^1$ is chloro, fluoro, methyl, ethyl, isopropyl, t-butyl, trifluoromethyl, difluoromethyl, cyano, methoxy, methyl-S—, difluoromethoxy, trifluoromethoxy, trifluoromethyl-S—, methyl-O-ethoxy-, hydroxymethyl, isoproproxy, cyclobutoxy, cyclopropxy, cyclopentyloxy, ethylC(O)—, dimethylamine, hydroxy, nitro, 3-methyl-pyridinyl-O—, 6-methyl-pyridinyl-O—, 5-methyl-pyridinyl-O—,or phenyl, or two $R^1$ groups are linked together with the carbon to which they are both attached to form

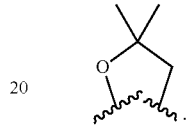.

3. The compound of claim 2, or a pharmaceutically acceptable salt thereof, wherein $R^4$ is hydrogen.

4. A compound according to the formula:

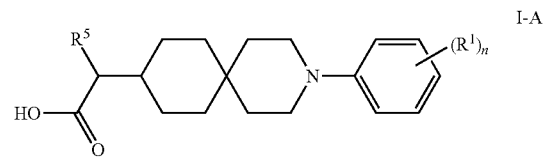

or a pharmaceutically acceptable salt thereof, wherein:
each $R^1$ is
  (1) halo,
  (2) $(C_{1-6})$alkyl,
  (3) halo$(C_{1-6})$alkyl,
  (4) hydroxy$(C_{1-6})$alkyl,
  (5) $(C_{1-6})$alkoxy,
  (6) halo$(C_{1-6})$alkoxy,
  (7) $(C_{1-2})$alkoxy-$(C_{1-6})$alkoxy,
  (8) $(C_{1-6})$alkyl-S—,
  (9) halo$(C_{1-6})$alkyl-S—,
  (10) nitro,
  (11) $(C_{3-7})$cycloalkyl-O—,
  (12) cyano,
  (13) hydroxy,
  (14) $(C_{1-6})$alkylC(O)—,
  (15) $((C_{1-6})$alkyl$)_2$N—,
  (16) phenyl, or
  (17) 5- or 6-membered heteroaryloxy ring, containing 1-3 O, N, and S ring atoms, wherein the phenyl and heteroaryloxy, groups are optionally substituted by 1-3 $(C_{1-6})$alkyl, halo$(C_{1-6})$alkyl, or halo groups; or alternatively two $R^1$ groups are linked together with the carbon to which they are both attached to form

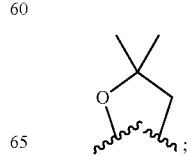;

$R^5$ is hydrogen or $(C_{1-6})$alkyl; and
n is 1, 2, or 3.
5. A compound selected from the group consisting of:
1
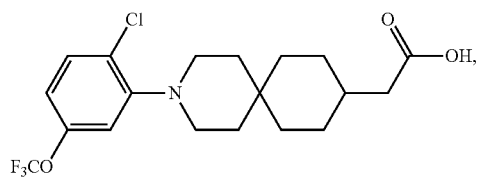
2
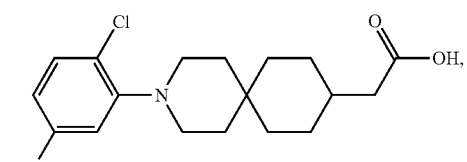
3
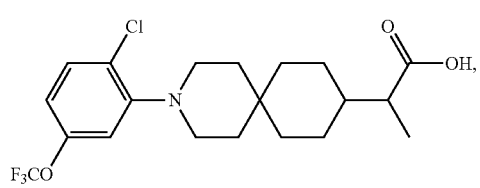
4
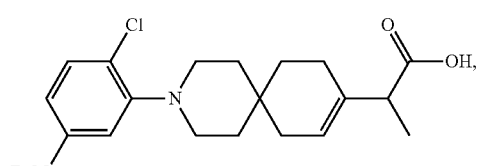
5
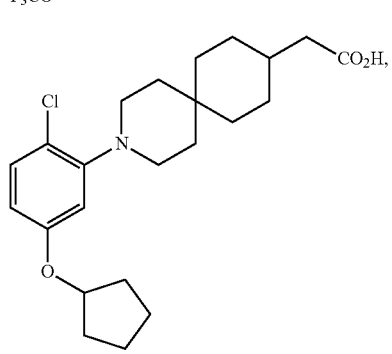
6
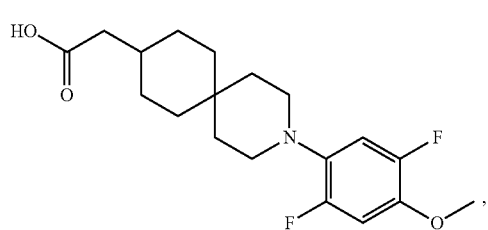
7
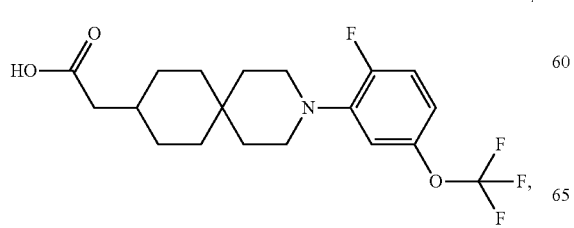
8
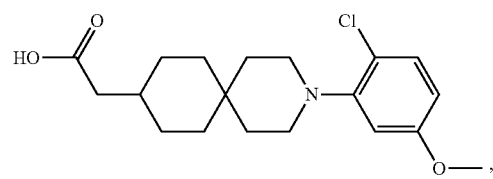
9
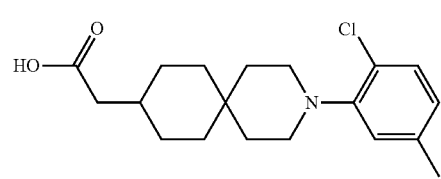
10
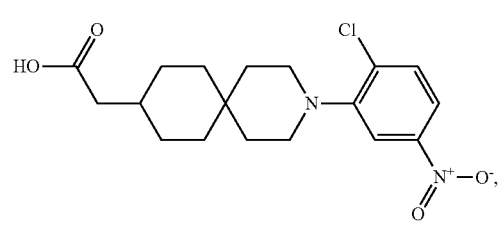
11
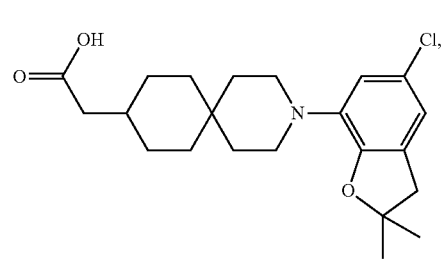
12
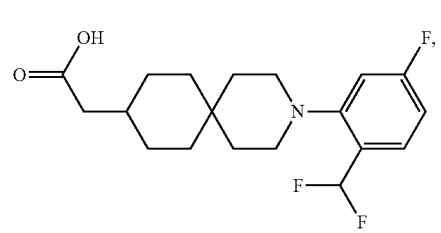
13
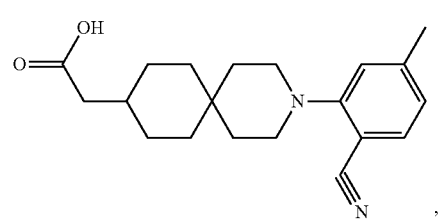
14
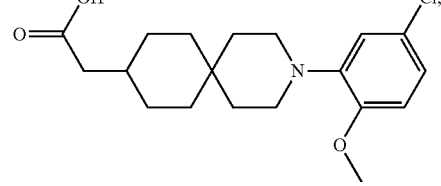

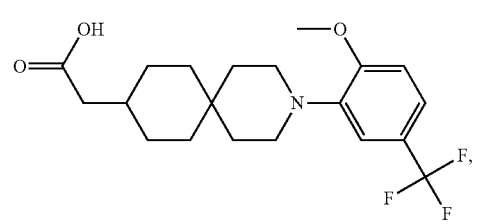
15
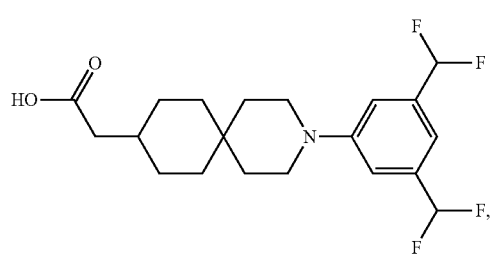
22
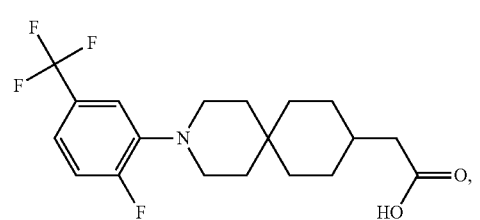
16
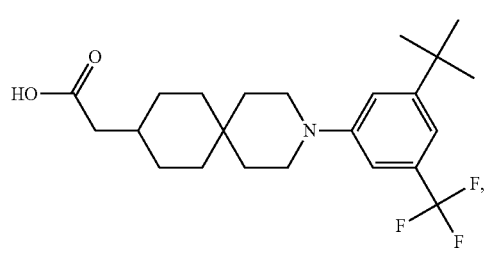
23
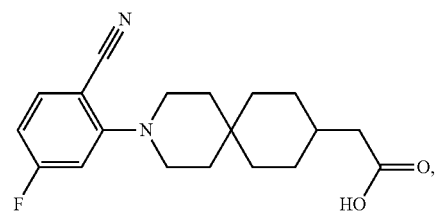
17
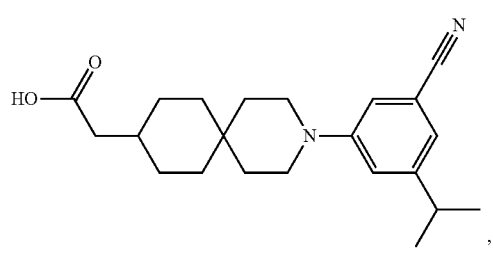
24
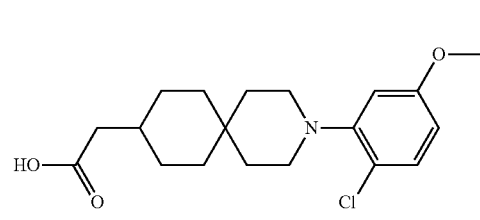
18
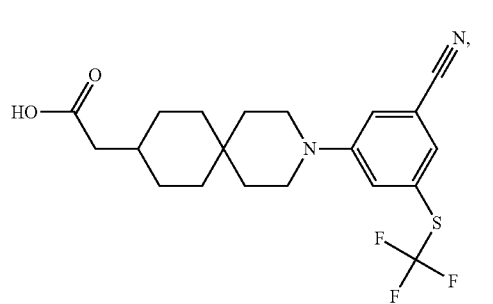
25
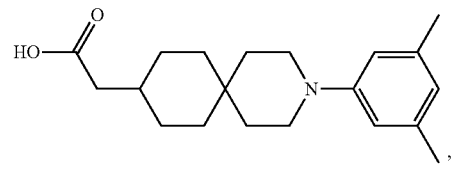
19
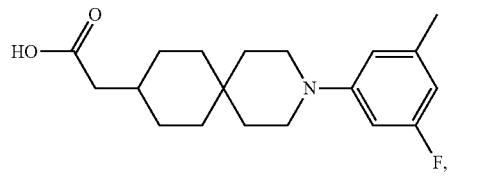
28
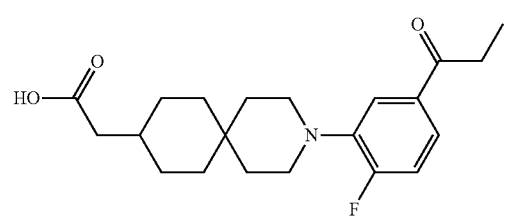
20
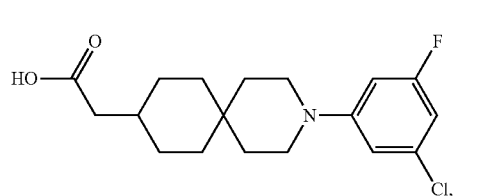
29
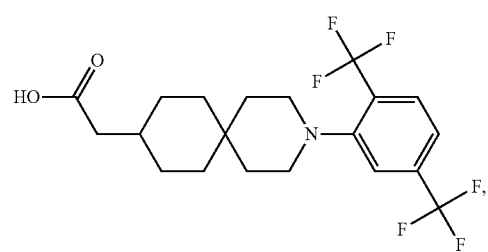
21
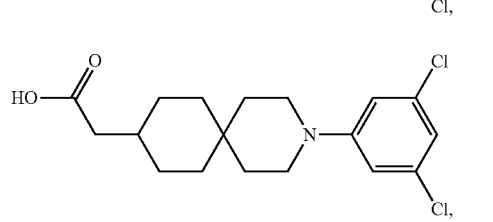
30

-continued
31
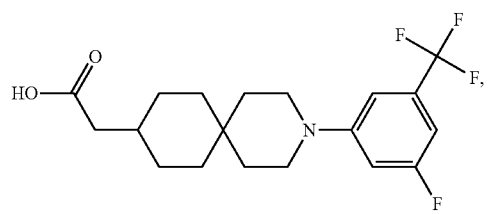
32
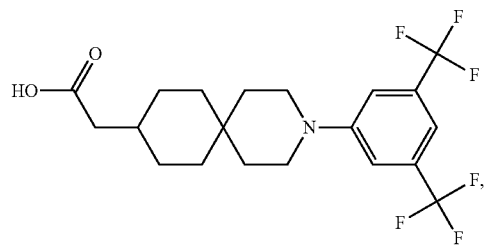
34
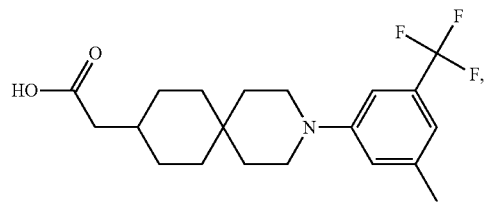
35
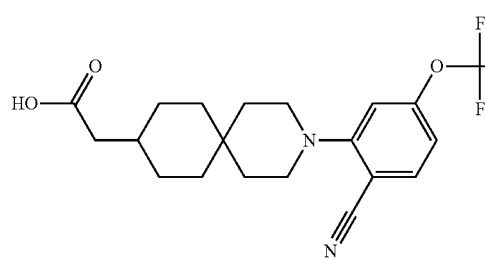
36
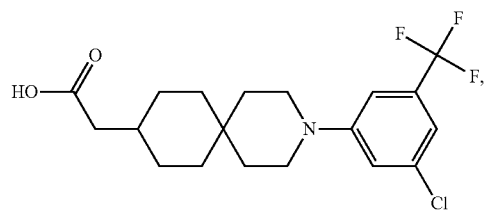
37
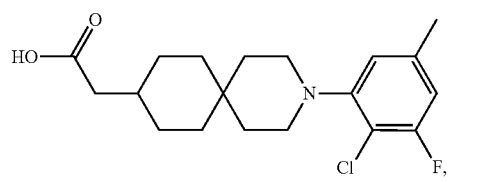
38
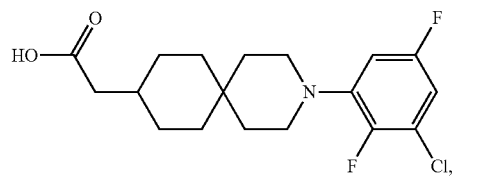
-continued
39
40
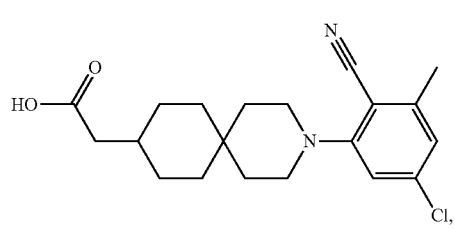
41
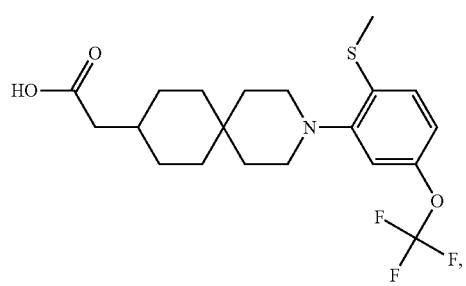
42
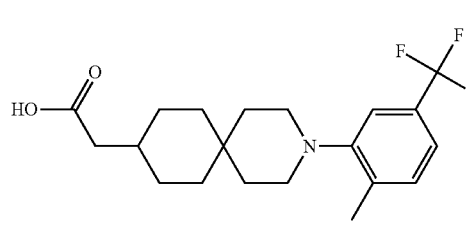
43
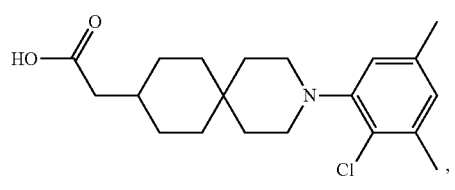
44
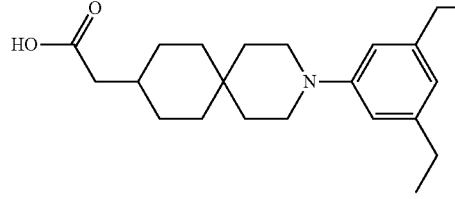
45

46 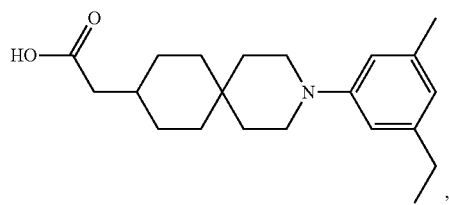
47 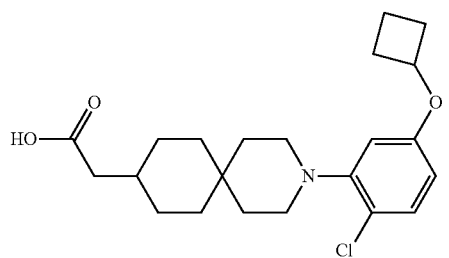
48 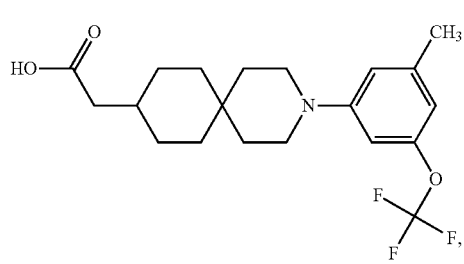
49 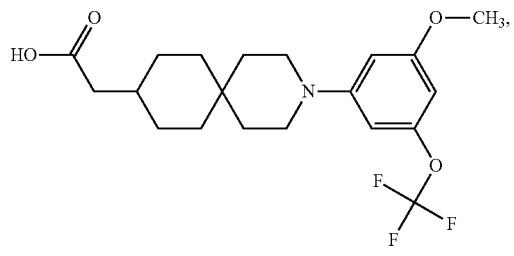
50 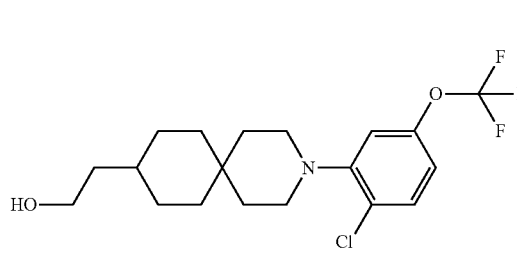
51 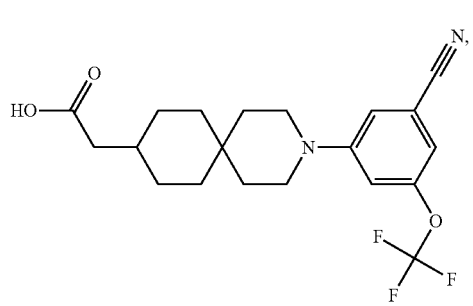
52 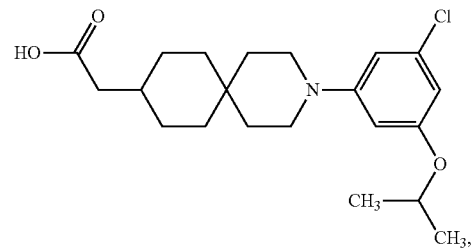
53 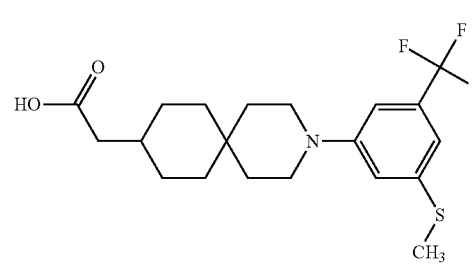
54 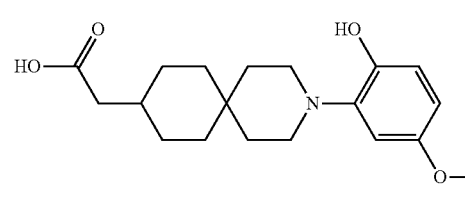
55 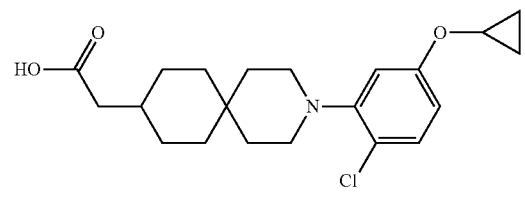
56 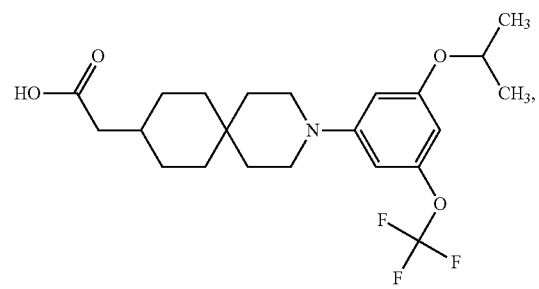
57 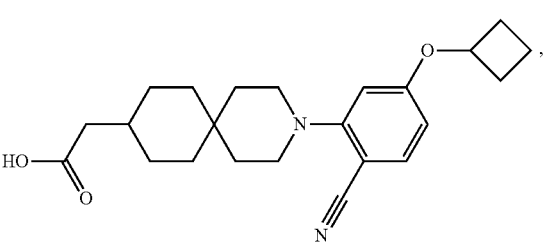

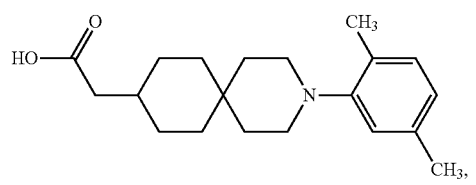
58
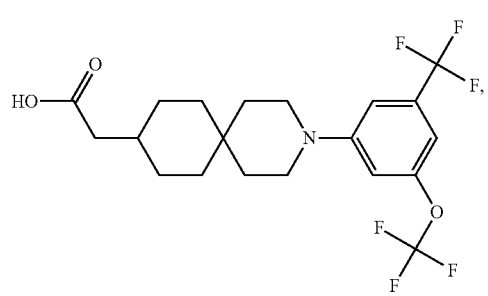
59
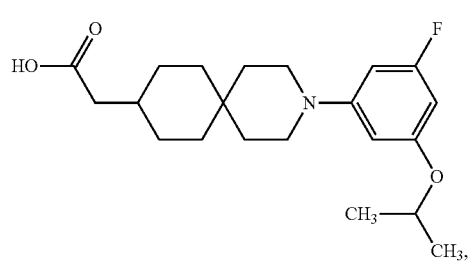
60
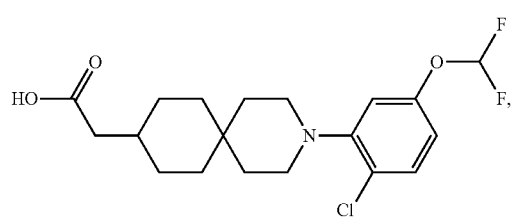
61
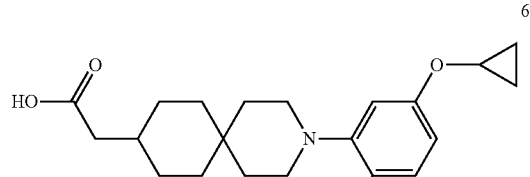
62
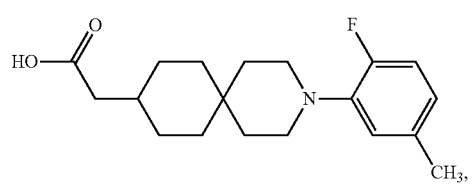
63
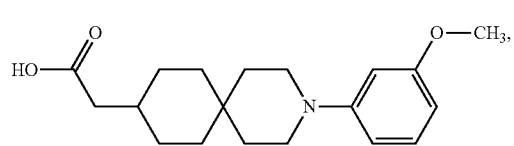
64
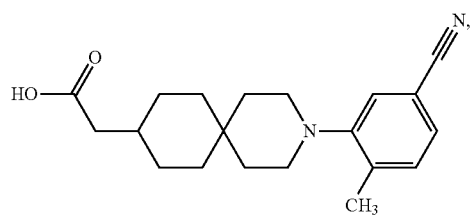
65
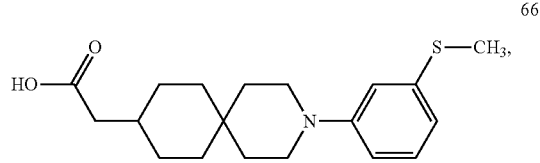
66
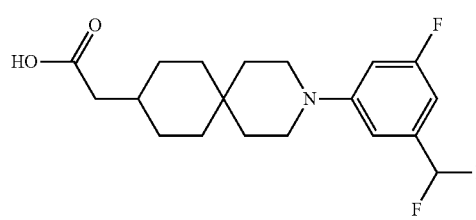
67
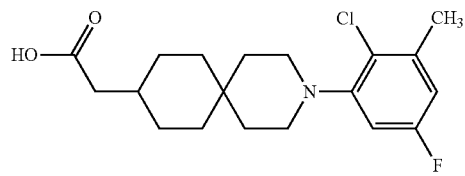
68
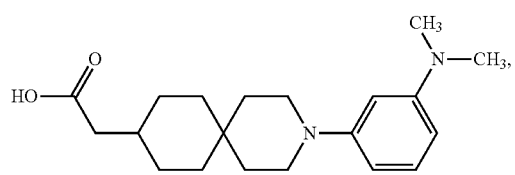
69
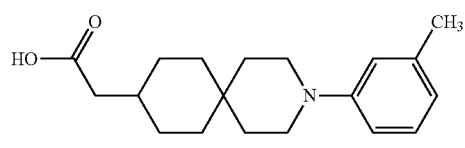
70
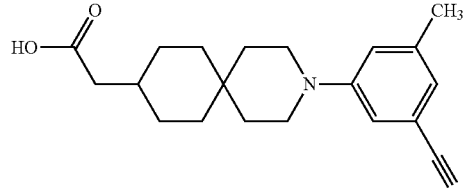
71
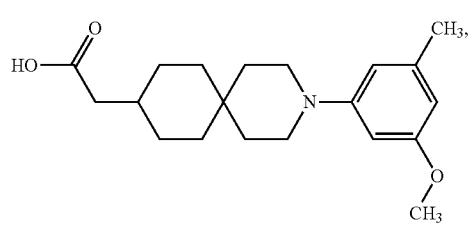
72

73 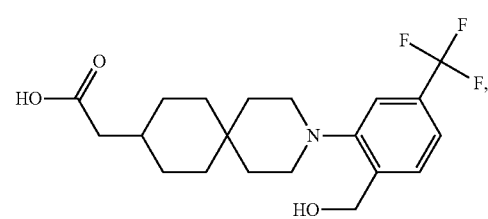
75 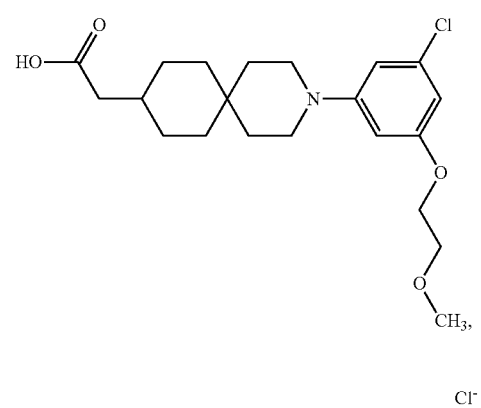
76 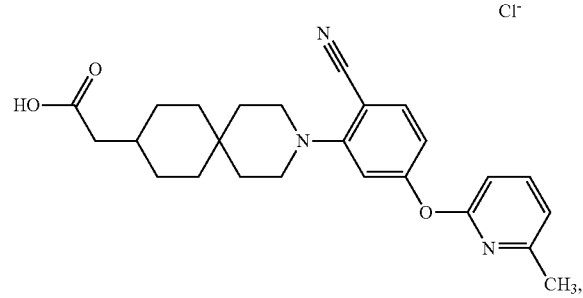
77 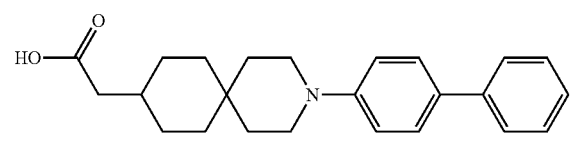
78 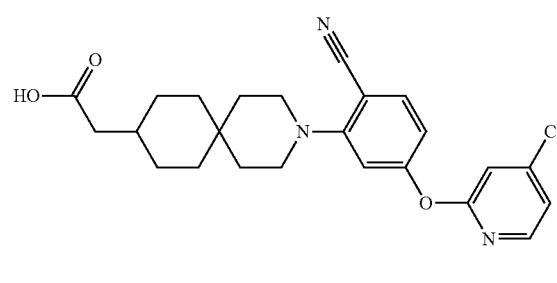
79 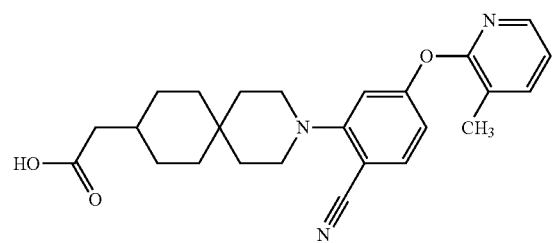
80 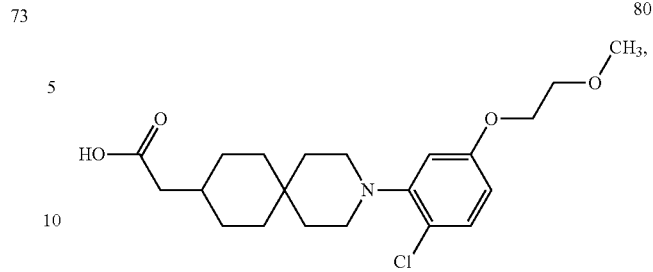
81 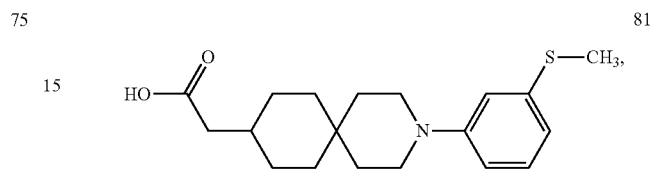
82 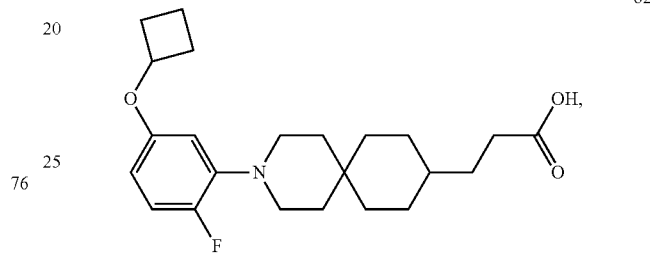
83 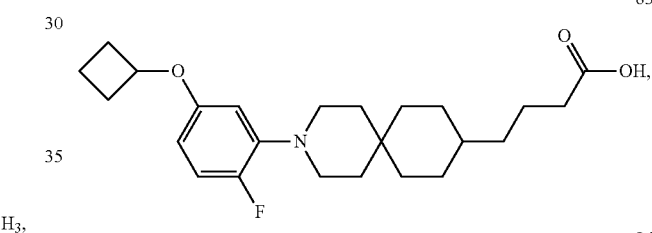
84 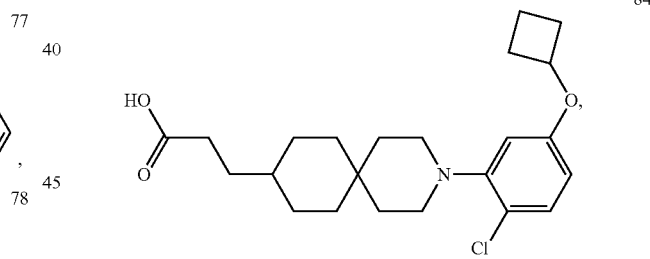
85 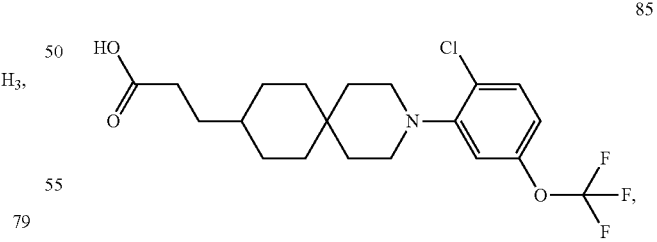
86 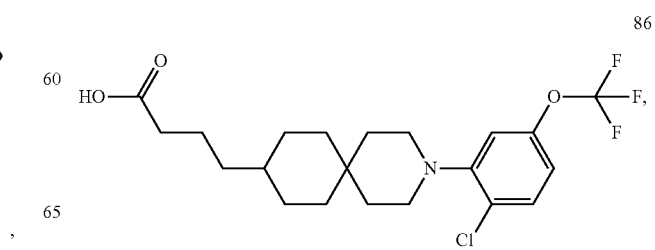

-continued
87
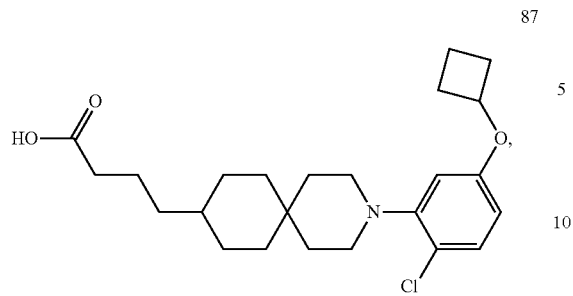
88
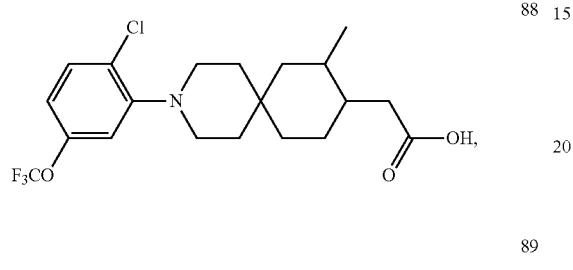
89
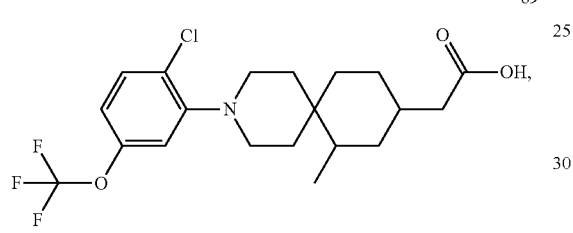
90
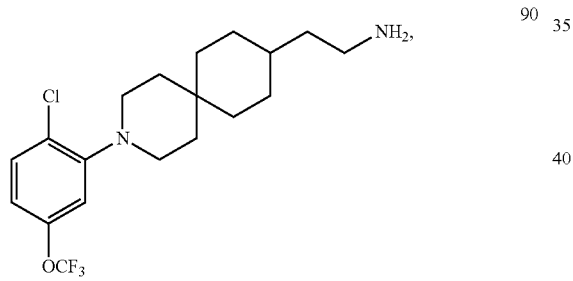
91
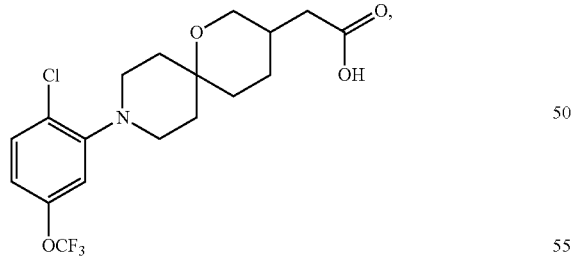
92
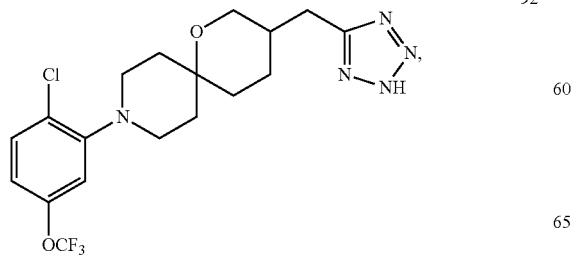
-continued
93a
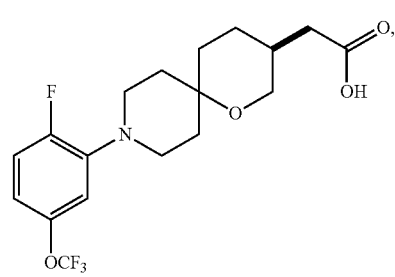
93b
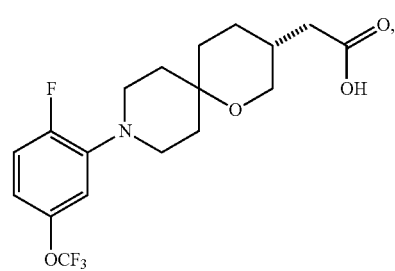
94
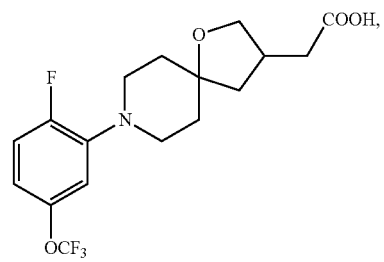
95
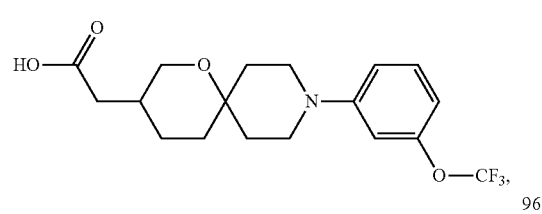
96
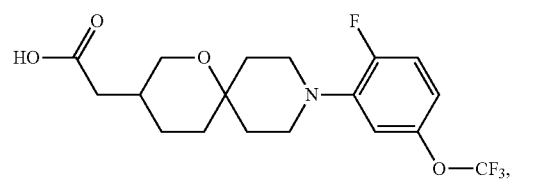
97
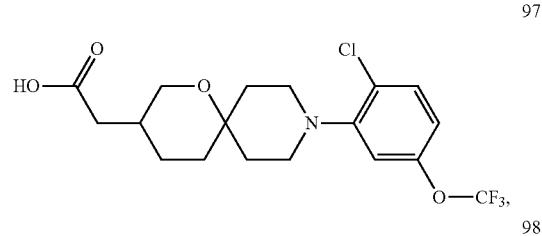
98

-continued

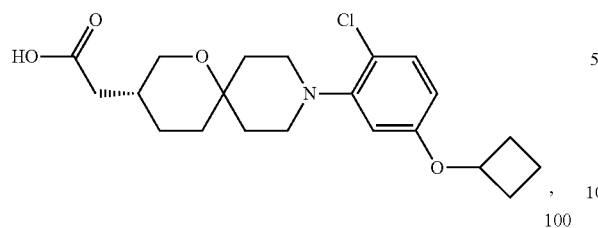
99

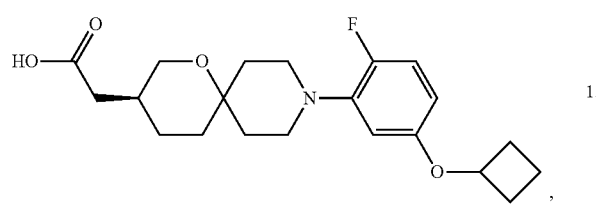
100

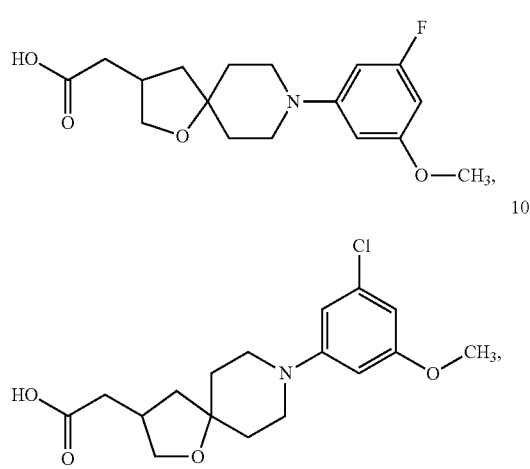
101

102

103

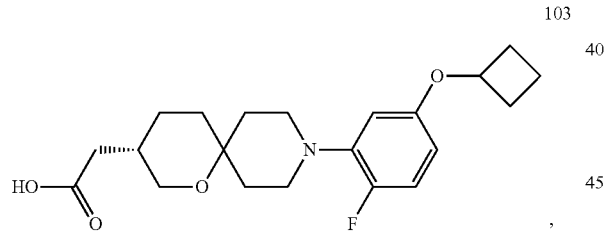
104

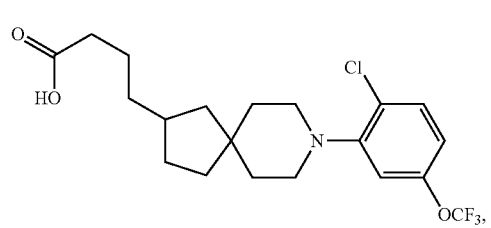
105

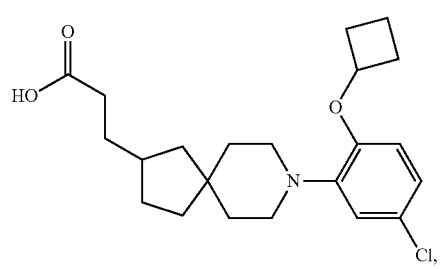

-continued

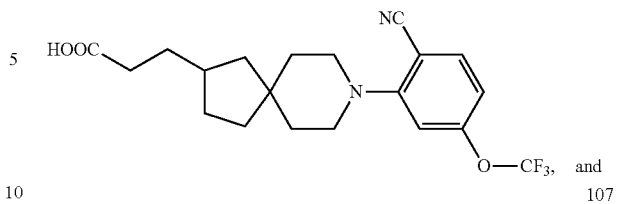
106

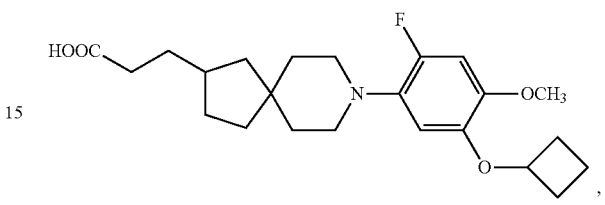
107 or a pharmaceutically acceptable salt thereof.

6. A pharmaceutical composition comprising a compound of claim 1 in combination with a pharmaceutically acceptable carrier.

7. The compound of claim 1, or a pharmaceutically acceptable salt thereof, wherein each $R^1$ is chloro, fluoro, methyl, ethyl, isopropyl, t-butyl, trifluoromethyl, difluoromethyl, cyano, methoxy, methyl-S—, difluoromethoxy, trifluoromethoxy, trifluoromethyl-S—, methyl-O-ethoxy-, hydroxymethyl, isoproproxy, cyclobutoxy, cyclopropxy, cyclopentyloxy, ethylC(O)—, dimethylamine, hydroxy, nitro, 3-methyl-pyridinyl-O—, 6-methyl-pyridinyl-O—, 5-methyl-pyridinyl-O—,or phenyl, or two $R^1$ groups are linked together with the carbon to which they are both attached to form

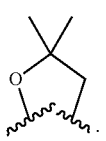

8. The compound of claim 7, or a pharmaceutically acceptable salt thereof, wherein $R^4$ is hydrogen.

9. The compound of claim 1, or a pharmaceutically acceptable salt thereof, wherein each $R^1$ is chloro, fluoro, methyl, ethyl, isopropyl, t-butyl, trifluoromethyl, difluoromethyl, cyano, methoxy, methyl-S—, difluoromethoxy, trifluoromethoxy, trifluoromethyl-S—, methyl-O-ethoxy-, hydroxymethyl, isoproproxy, cyclobutoxy, cyclopropxy, cyclopentyloxy, ethylC(O)—, dimethylamine, hydroxy, nitro, 3-methyl-pyridinyl-O—, 6-methyl-pyridinyl-O—, 5-methyl-pyridinyl-O—,or phenyl, or two $R^1$ groups are linked together with the carbon to which they are both attached to form

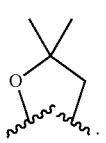

10. The compound of claim 4, or a pharmaceutically acceptable salt thereof, wherein each $R^1$ is chloro, fluoro, methyl, ethyl, isopropyl, t-butyl, trifluoromethyl, difluoromethyl, cyano, methoxy, methyl-S—, difluoromethoxy, trifluoromethoxy, trifluoromethyl-S—, methyl-O-ethoxy-, hydroxymethyl, isoproproxy, cyclobutoxy, cyclopropxy, cyclopentyloxy, ethylC(O)—, dimethylamine, hydroxy, nitro, 3-methyl-pyridinyl-O—, 6-methyl-pyridinyl-O—, 5-methyl-pyridinyl-O—,or phenyl, or two $R^1$ groups are linked together with the carbon to which they are both attached to form

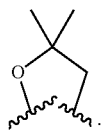

* * * * *

```
                        SEQUENCE LISTING

<160> NUMBER OF SEQ ID NOS: 4

<210> SEQ ID NO 1
<211> LENGTH: 38
<212> TYPE: DNA
<213> ORGANISM: Homo sapiens

<400> SEQUENCE: 1
aggatccgcc gccatgtccc ctgaatgcgc gcgggcag                       38

<210> SEQ ID NO 2
<211> LENGTH: 36
<212> TYPE: DNA
<213> ORGANISM: Homo sapiens

<400> SEQUENCE: 2
cgaattctta gccagaaata atcgacaagt catttc                         36

<210> SEQ ID NO 3
<211> LENGTH: 39
<212> TYPE: DNA
<213> ORGANISM: Homo sapiens

<400> SEQUENCE: 3
aggatccgcc gccatgtccc ctgagtgtgc acagacgac                      39

<210> SEQ ID NO 4
<211> LENGTH: 36
<212> TYPE: DNA
<213> ORGANISM: Homo sapiens

<400> SEQUENCE: 4
cgaattctta gctggaaata acagacaagt catttc                         36
```